US008003106B2

(12) United States Patent
Mikayama et al.

(10) Patent No.: US 8,003,106 B2
(45) Date of Patent: Aug. 23, 2011

(54) HUMAN MONOCLONAL ANTIBODIES TO INFLUENZA M2 PROTEIN AND METHODS OF MAKING AND USING SAME

(75) Inventors: Toshifumi Mikayama, Nagareyama (JP); Rongfang Wang, Shanghai (CN); Shinichiro Kato, Chiba (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 157 days.

(21) Appl. No.: 12/039,632

(22) Filed: Feb. 28, 2008

(65) Prior Publication Data

US 2009/0162366 A1 Jun. 25, 2009

Related U.S. Application Data

(63) Continuation-in-part of application No. 10/909,851, filed on Aug. 2, 2004, now abandoned, which is a continuation-in-part of application No. 10/389,221, filed on Mar. 13, 2003, now abandoned, and a continuation-in-part of application No. PCT/US03/08147, filed on Mar. 13, 2003.

(60) Provisional application No. 60/364,997, filed on Mar. 13, 2002.

(51) Int. Cl.
*A61K 39/42* (2006.01)
*A61K 39/145* (2006.01)

(52) U.S. Cl. ............... 424/159.1; 424/185.1; 424/206.1; 536/23.72; 435/5

(58) Field of Classification Search ........................ None
See application file for complete search history.

(56) References Cited

U.S. PATENT DOCUMENTS 6,350,861 B1 * 2/2002 Co et al. .................. 530/388.85

OTHER PUBLICATIONS

Zebedee et al. Journal of Virology, 1988, 62(8):2762-2772.*
Treanor et al. Journal of Virology, 1990, 64(3):1375-1377.*
Lin et al., PNAS USA, 2000, 97(17):9654-9658.*
Genbank accession No. AJ278647 (2000), 3 pages.*
Buckler-White et al., Journal of Virology, 1986, 57(2):697-700.*
Guan et al., PNAS USA, 1999, 96(16):9363-9367.*
Genbank accession No. AF 156464 (1999), 2 pages.*
Genbank accession No. AF 156468 (1999), 2 pages.*
Suarez et al., Journal of Virology, 1999, 73(5):3567-3573.*
Genbank accession No. AF 073194 (1999), 2 pages.*
Sugrue et al., Virology, 1990, 179:51-56.*

* cited by examiner

*Primary Examiner* — Stacy B. Chen
(74) *Attorney, Agent, or Firm* — Pillsbury Winthrop Shaw Pittman LLP

(57) ABSTRACT

Human, humanized and chimeric monoclonal antibodies that bind to influenza M2 protein. The antibodies are useful for, among other things, treatment, diagnostics, purifying and isolating M2 or influenza virus, and identifying the presence of M2 or influenza virus in a sample or a subject.

58 Claims, 8 Drawing Sheets

Fig. 1

C40Lv (fragment A was obtained after BglII+BsiW1 digestion)

```
               BglII
  1  AGAGAGAGAGATCTCTCACCATGAGGGTCCTCGCTCAGCTCCTGGGGCTC
     TCTCTCTCTCTAGAGAGTGGTACTCCCAGGAGCGAGTCGAGGACCCCGAG
                           1▶ M  R  V  L  A  Q  L  L  G  L
 51  CTGCTGCTCTGTTTCCCAGGTGCCAGATGTGACATCCAGATGACCCAGTC
     GACGACGAGACAAAGGGTCCACGGTCTACACTGTAGGTCTACTGGGTCAG
 11▶ L  L  L  C  F  P  G  A  R  C  D  I  Q  M  T  Q  S
101  TCCATCCTCACTGTCTGCATCTGTAGGAGACAGAGTCACCATCACTTGTC
     AGGTAGGAGTGACAGACGTAGACATCCTCTGTCTCAGTGGTAGTGAACAG
 27▶  P  S  S  L  S  A  S  V  G  D  R  V  T  I  T  C
151  GGGCGAGTCAGGGTATTAGCAGCTGGTTAGCCTGGTATCAGCAGAAACCA
     CCCGCTCAGTCCCATAATCGTCGACCAATCGGACCATAGTCGTCTTTGGT
 44▶R  A  S  Q  G  I  S  S  W  L  A  W  Y  Q  Q  K  P
201  GAGAAAGTCCCTAAGTCCCTGATCTATGCTGCATCCAGTTTGCAAAGTGG
     CTCTTTCAGGGATTCAGGGACTAGATACGACGTAGGTCAAACGTTTCACC
 61▶ E  K  V  P  K  S  L  I  Y  A  A  S  S  L  Q  S  G
251  GGTCCCATCAAGGTTCAGCGGCAGTGGATCTGGGACAGATTTCACTCTCA
     CCAGGGTAGTTCCAAGTCGCCGTCACCTAGACCCTGTCTAAAGTGAGAGT
 77▶  V  P  S  R  F  S  G  S  G  S  G  T  D  F  T  L
301  CCATCAGCAGCCTGCAGCCTGAAGATTTTGCAACTTATTACTGCCAACAG
     GGTAGTCGTCGGACGTCGGACTTCTAAAACGTTGAATAATGACGGTTGTC
 94▶T  I  S  S  L  Q  P  E  D  F  A  T  Y  Y  C  Q  Q
351  TATAATTATTACCCGCTCACTTTCGGCGGAGGGACCAAGGTGGAGATCAA
     ATATTAATAATGGGCGAGTGAAAGCCGCCTCCCTGGTTCCACCTCTAGTT
111▶ Y  N  Y  Y  P  L  T  F  G  G  G  T  K  V  E  I  K
       BsiWI
401  ACGTACGAGAGAGAG
     TGCATGCTCTCTCTC
127▶  R  T  R  E
```

C40Hv (fragment D was obtained after SalI+NheI digestion)

```
               SalI
  1  AGAGAGAGGTCGACACCATGAAGCACCTGTGGTTCTTCCTCCTGCTGGTGGCG
     TCTCTCTCCAGCTGTGGTACTTCGTGGACACCAAGAAGGAGGACGACCACCGC
                      1▶ M  K  H  L  W  F  F  L  L  L  V  A
 54  GCTCCCAGATGGGTCCTGTCCCAGCTGCAGCTGCAGGAGTCGGGCCCAGGACT
     CGAGGGTCTACCCAGGACAGGGTCGACGTCGACGTCCTCAGCCCGGGTCCTGA
 13▶ A  P  R  W  V  L  S  Q  L  Q  L  Q  E  S  G  P  G  L
107  GGTGAAGCCTTCGGAGACCCTGTCCCTCACCTGCACTGTCTCTGGTGGTTCCA
     CCACTTCGGAAGCCTCTGGGACAGGGAGTGGACGTGACAGAGACCACCAAGGT
 30▶  V  K  P  S  E  T  L  S  L  T  C  T  V  S  G  G  S
                                      BamHI
160  TCAGCAGTAGTTTTTACTACTGTGGCTGGATCCGCCAGCCCCCAGGGAAGGGG
     AGTCGTCATCAAAAATGATGACACCGACCTAGGCGGTCGGGGGTCCCTTCCCC
 48▶I  S  S  S  F  Y  Y  C  G  W  I  R  Q  P  P  G  K  G
213  CTGGAGTGGATTGGGAGTATCTATTATCGTGGGAGCACCTACTACAACCCGTC
     GACCTCACCTAACCCTCATAGATAATAGCACCCTCGTGGATGATGTTGGGCAG
 66▶ L  E  W  I  G  S  I  Y  Y  R  G  S  T  Y  Y  N  P  S
266  CCTCAAGAGTCGAGTCACCATATCCGTAGACACGTCCAAGAACCAGTTCTCCC
     GGAGTTCTCAGCTCAGTGGTATAGGCATCTGTGCAGGTTCTTGGTCAAGAGGG
 83▶  L  K  S  R  V  T  I  S  V  D  T  S  K  N  Q  F  S
319  TGAAGCTGAGCTCTGTGACCGCCGCAGACACGGCTGTGTATTACTGTGCGAGA
     ACTTCGACTCGAGACACTGGCGGCGTCTGTGCCGACACATAATGACACGCTCT
101▶L  K  L  S  S  V  T  A  A  D  T  A  V  Y  Y  C  A  R
372  CGGGTTACTATGGTTCGGGGAGTTAAGGGGGACTACTTTGACTACTGGGGCCA
     GCCCAATGATACCAAGCCCCTCAATTCCCCCTGATGAAACTGATGACCCCGGT
119▶ R  V  T  M  V  R  G  V  K  G  D  Y  F  D  Y  W  G  Q
                                 NheI
425  GGGAACCCTGGTCACCGTCTCCTCAGCTAGCCTCTCTCT
     CCCTTGGGACCAGTGGCAGAGGAGTCGATCGGAGAGAGA
136▶  G  T  L  V  T  V  S  S  A  S
```

HUMAN MONOCLONAL ANTIBODIES TO INFLUENZA M2 PROTEIN AND METHODS OF MAKING AND USING SAME

PRIORITY APPLICATION INFORMATION

This application is a continuation-in-part of and claims priority to U.S. application Ser. No. 10/909,851, filed Aug. 2, 2004, now abandoned which is a continuation-in-part of U.S. application Ser. No. 10/389,221, filed Mar. 13, 2003, now abandoned, PCT/US03/08147, filed Mar. 13, 2003, and U.S. Provisional Application Ser. No. 60/364,997, filed Mar. 13, 2002.

TECHNICAL FIELD

The invention relates to antibodies, more particularly to human, humanized and chimeric antibodies that specifically bind to influenza virus M2 protein.

INTRODUCTION

Influenza types A or B viruses cause epidemics of disease almost every winter in all countries and are a leading cause of death in the developed world. In the United States, these winter influenza epidemics can cause illness in 10% to 20% of people and are associated with an average of 20,000 deaths and 114,000 hospitalizations per year. The present strategy for control of influenza is yearly vaccination with inactivated whole-virus or sub-unit vaccines. The major neutralizing antigen of the influenza virus is hemagglutinin (HA) (Frace et al., *Vaccine* 17:2237 (1999)). However, due to frequent and unpredictable antigenic variation of HA, the vaccine frequently fails to provide optimal protective immunity against divergent viral strains. Moreover, for immuno-compromised individuals such as elderly patients, cancer patients and other patients who are immuno-incompetent due to ongoing treatment and/or disease, vaccination may not provide effective protection.

Hemagglutinin (HA) and neuraminidase (NA) are the two major antigens for the stimulation of antibody production. Due to frequent antigenic variation of these two proteins, they do not represent optimal targets for development of therapeutic drugs. A third transmembrane protein of type A influenza viruses, matrix protein 2 (M2), is abundantly expressed by virus-infected cells, where it is postulated to provide an obligatory transmembrane proton flux for viral replication (Ciampor et al., *Virus Research* 22:247 (1992), Grambas and Hay, *Virology* 190:11 (1992); Sugrue et al., *EMBO Journal* 9:3469 (1990)). Unlike HA and NA, M2 is conserved and may represent a target for the development of antibody-based passive immunotherapies for influenza patients (Ito et al., *J. Virology* 65:5491 (1991); Slepushkin et al., *Vaccine* 13:1399 (1995); Neirynck et al., *Nature Med.* 5:1157 (1999)).

Vaccination of mice with baculovirus-expressed M2 protein has been reported to enhance clearance of virus from mouse lungs and protect mice from a lethal challenge with both homologous and heterologous influenza A viruses (Slepushkin et al., *Vaccine* 13:1399 (1995)). A more recent report has shown that the fusion of the extracellular domain of M2 to the hepatitis B virus core (HBc) protein to create a fusion gene coding for M2HBc, when used as a vaccine could provide 90-100% protection against a lethal virus challenge in mice (Neirynck et al., *Nature Med.* 5:1157 (1999)). This protection could be passively transferred to unvaccinated mice using serum from M2HBc vaccinated mice. Zebedee et. al. demonstrated that an anti-M2 mouse monoclonal antibody had a moderate effect on the growth of influenza virus in a plaque assay. The size of the plaques, but not the number of plaques, for the A/Udorn/72 virus was smaller when the antibody was present during incubation. No effect was observed on the size or number of plaques for the A/WSN/33 strain indicating that this particular monoclonal antibody is not broadly effective against different influenza strains (Zebedee and Lamb, *J. Virol* 62:2762 (1988)). When this antibody was passively transferred to mice one day before viral challenge, the level of virus replication in the lungs 3 to 4 days after infection was approximately 100-fold less than that in animals receiving an irrelevant antibody (Treanor et al., *J. Virol* 64:1375). However, when this antibody was administered to SCID mice one day before virus infection, lung virus titers were no different from control mice (Palladino et al., *J. Virol.* 69:2075 (1995)). Mozdzanowska et. al. (*Virology* 254:138 (1999) using the same murine anti-M2 monoclonal antibody, 14C2, was able to demonstrate, in agreement with Zebeedee et. al, that an anti-M2 monoclonal antibody can reduce virus titers in a viral plaque assay but was unable to reduce viral titer of influenza strain A/PR/8/34 indicating that 14C2 does not broadly protect against influenza.

SUMMARY

Fully human, humanized and chimeric (e.g., human/mouse chimera) anti-M2 monoclonal antibodies disclosed herein can recognize the A/PR/8/34 and A/HK/8/68 strains indicating broad reactivity against influenza A. Furthermore, human, humanized and chimeric anti-M2 monoclonal antibody disclosed herein can protect mice from a lethal challenge of the A/PR/8/34 influenza A strain when the antibody is administered after the animals have been infected with influenza A.

The invention therefore provides human, humanized and chimeric antibodies that bind to influenza virus protein M2, compositions such as pharmaceutical compositions including human, humanized and chimeric antibody, and kits containing the antibody. The human, humanized and chimeric antibodies of the invention are useful for treating influenza in a subject having or at risk of having influenza, including before infection (prophylaxis) or following infection (therapeutic); influenza diagnostics, including measuring virus titre; purification/isolation including purifying or isolating whole virus or M2 protein; and other assay systems. The invention therefore also provides methods of using the antibodies in therapy (e.g., treatment of influenza infection), diagnostics (detecting amounts of influenza or M2 protein in a sample) and purification (purifying or isolating influenza virus or M2 protein).

In one embodiment, a human antibody that specifically binds to at least a part of the M2 extracellular domain is provided. In particular aspects, a sequence includes or consists of SLLTEVETPIRNEWGCRCNDSSD (M2, SEQ ID NO:1), a subsequence thereof or an amino acid variant thereof (e.g., an amino acid substitution, insertion, deletion or addition). In another aspect, a sequence includes or consists of an amino acid sequence selected from:

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

-continued

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
and

SLLPEVETHTRNGWGCRCSDSSD. (M2PHTGS; SEQ ID NO: 22)

In various aspects, antibody is produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA).

Antibodies of the invention further include human, humanized and chimeric antibodies that bind to two or more M2 proteins having different amino acid sequences (e.g., having different extracellular domain sequences), which may optionally be present on different influenza viruses (e.g., strains or isolates). In one embodiment, the antibody binds to at least a part of an M2 extracellular domain sequence. In particular aspects, a sequence includes or consists of SLLTEVETPIRNEWGCRCNDSSD (SEQ ID NO:1), a subsequence thereof or an amino acid variant thereof (e.g., an amino acid substitution, insertion, deletion or addition), such as SLLTEVETPIRNEWECRCNGSSD (M2EG, SEQ ID NO:2). In other particular aspects, a sequence includes or consists of:

SLLTEVETPIRNEWGCKCNDSSD; (MEK, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

-continued

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
and

SLLPEVETHTRNGWGCRCSDSSD. (M2PHTGS; SEQ ID NO: 22)

In additional embodiments, an antibody binds to an influenza virus M2 sequence under certain assay conditions. In one embodiment, an antibody specifically binds to one or more of M2TGEKS (SEQ ID NO:10), M2TDGEKS (SEQ ID NO:15), M2LTGEKS (SEQ ID NO:9) or M2TGE (SEQ ID NO:19), as determined by a peptide based ELISA assay wherein the antibody is at a concentration of 10 μg/ml. In another embodiment, an antibody specifically binds to an influenza protein M2 extracellular domain, wherein the antibody has a binding activity (EC50) of less than $10^{-8}$ M for M2LTGEKS (SEQ ID NO:9) or M2TGEK (SEQ ID NO:13), as determined by an ELISA assay of binding between the antibody and an M2LTGEKS-BSA or M2TGEK-BSA conjugate. In an additional embodiment, an antibody specifically binds to an influenza protein M2 extracellular domain, wherein the antibody has a binding activity (EC50) of less than $10^{-9}$ M for M2LTGEKS (SEQ ID NO:9) or M2TGEK (SEQ ID NO:13), as determined by an ELISA assay of binding between the antibody and an M2LTGEKS-BSA or M2TGEK-BSA conjugate. In a further embodiment, an antibody specifically binds to an influenza protein M2 extracellular domain, wherein the antibody has a binding activity (EC50) of less than $10^{-8}$ M for M2LTGEKS (SEQ ID NO:9) or M2TGEK (SEQ ID NO:13), wherein the antibody has a binding activity (EC50) of greater than $10^{-8}$ M for one or more of M2TGS (SEQ ID NO:12) or M2TGE (SEQ ID NO:19), and wherein binding activity is determined by an ELISA assay of binding between the antibody and a M2LTGEKS-BSA, M2TGEK-BSA, M2TGS-BSA or M2TGE-BSA conjugate. In still another embodiment, an antibody specifically binds to an influenza protein M2 extracellular domain, wherein the antibody has a binding activity (EC50) of less than $10^{-9}$ M for M2LTGEKS (SEQ ID NO:9) or M2TGEK (SEQ ID NO:13), wherein the antibody has a binding activity (EC50) of greater than $10^{-8}$ M for one or more of M2TGS (SEQ ID NO:12) or M2TGE (SEQ ID NO:19), and wherein binding activity is determined by an ELISA assay of binding between the antibody and a M2LTGEKS-BSA, M2TGEK-BSA, M2TGS-BSA or M2TGE-BSA conjugate.

Antibodies of the invention further include antibodies (e.g., human, humanized and chimeric) that bind to a minimal binding sequence of an M2 protein. In various embodiments, an antibody binds to a minimal binding sequence that is LLTEVETPIRNEWGC (SEQ ID NO:25); SLLTEVETPIRNEWGC (SEQ ID NO:23); or TPIRNE (SEQ ID NO:24). In additional embodiments, a minimal binding sequence for antibody binding is LLTEVETPIRNEWGC (SEQ ID NO:25); SLLTEVETPIRNEWGC (SEQ ID NO:23); or TPIRNE (SEQ ID NO:24). In further embodiments, an antibody specifically binds to a sequence that is the same or substantially the same as LLTEVETPIRNEWGC (SEQ ID NO:25); SLLTEVETPIRNEWGC (SEQ ID NO:23); or TPIRNE (SEQ ID NO:24). In still further embodiments, the antibody binds to a minimal binding sequence that is the same or substantially the same as the minimal binding sequence to which antibody produced by the hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA,), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA) binds.

Antibodies of the invention optionally have a minimal binding sequence distinct from antibody 14C2 minimal binding sequence LTEVETPIRNEW (SEQ ID NO:71), or distinct from an antibody that has an apparent minimal binding sequence EVETPIRN (SEQ ID NO:72). Antibodies that do not specicially bind to a minimal binding sequence LTEVETPIRNEW (SEQ ID NO:71) and/or EVETPIRN (SEQ ID NO:72) are included. Thus, antibodies that bind to minimal binding sequence LTEVETPIRNEW (SEQ ID NO:71) and/or EVETPIRN (SEQ ID NO:72) may be excluded.

Antibodies of the invention include polyclonal and monoclonal antibodies and mixtures thereof, which can be any of IgG, IgA, IgM, IgE, IgD, and any isotype thereof, for example, $IgG_1$, $IgG_2$, $IgG_3$ or $IgG_4$. In the case of monoclonal antibodies, an exemplary class of antibody is IgG. Subclasses of IgG include, for example, $IgG_1$, $IgG_2$, $IgG_3$ and $IgG_4$.

Antibodies include intact human, humanized and chimeric immunoglobulin molecules with two full-length heavy chains and two full-length light chains (e.g., mature portion heavy and light chain variable region sequences) as well as subsequences of heavy or light chain which retain at least a part of a function (M2 binding specificity, M2 binding affinity or anti-influenza virus activity) of parental intact human, humanized and chimeric antibody that specifically binds M2. Subsequences can have the binding specificity or the same or substantially the same binding affinity as parental intact human, humanized and chimeric antibody. Exemplary subsequences include Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody ($(V_L\text{-}V_H)_2$ or $(V_H\text{-}V_L)_2$), triabody (trivalent), tetrabody (tetravalent), minibody ($(scFv\text{-}C_H3)_2$), bispecific single-chain Fv (Bis-scFv), IgGdeltaCH2, scFv-Fc or $(scFv)_2$-Fc, or other M2 protein binding fragment of an intact human or humanized immunoglobulin. Antibodies of the invention therefore include heavy-chain variable region sequence and light-chain variable region sequence of the antibody produced by the hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA,), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA).

Antibodies further include human, humanized and chimeric antibodies having the binding specificity (e.g., compete for binding), and antibodies having the same or substantially the same binding affinity, of an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA). In various aspects, the binding affinity is within about 5 to 100 fold of the reference antibody, or within about 5 to 5000 fold of the reference antibody. In another embodiment, an antibody binds to the same epitope as an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA). In yet another embodiment, an antibody binds to an epitope to which the antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA) binds. Exemplary epitopes (amino acid sequences) include all or a portion of SLLTEVETPIRNEWGC (SEQ ID NO:23); TPIRNE (SEQ ID NO:24); and LLTEVETPFRNEWGC (SEQ ID NO:25).

Antibodies of the invention therefore include antibodies that compete for binding to one or more of

```
SLLTEVETPRINEWGCRCNDSSD; (SEQ ID NO: 1)

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)
```

-continued

```
SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
or

SLLPEVETHTRNGWGCRCSDSSD, (M2PHTGS; SEQ ID NO: 22)
or a sequence that includes or consists of all or a
portion of a sequence set forth as
SLLTEVETPRINEWGC;        (SEQ ID NO: 23)

TPIRNE;                  (SEQ ID NO: 24)
or

LLTEVETPIRNEWGC.         (SEQ ID NO: 25)
```

Antibodies of the invention additionally include human, humanized and chimeric antibodies having the ability to inhibit virus infection in vitro or in vivo or that inhibit M2 binding of a cell in vitro or in vivo (e.g., MDCK cell), as the exemplified antibodies produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA). In various embodiments, an antibody has an $EC_{50}$ less than 2.0 to 3.0, 1.0 to 2.0, 0.5 to 1.0, 0.1 to 0.5 or less than 0.1 μg/ml (e.g., 0.05 to 0.1 μg/ml) for inhibiting influenza virus infection of MDCK cells, as determined by a cell based-ELISA assay. In additional embodiments, and antibody has an $EC_{50}$ less than 2.0 to 3.0, 1.0 to 2.0, 0.5 to 1.0, 0.1 to 0.5 or less than 0.1 μg/ml (e.g., 0.05 to 0.1 μg/ml) for inhibiting M2 binding to MDCK cells, as determined by a cell based-ELISA assay. In various aspects, the influenza virus is influenza A virus, such as A/PR/8/34 or A/HK/8/68, or another strain, such as H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 or H5N3.

Antibodies of the invention include those that have been modified to form oligomers, e.g., through the attachment of as oligomerization domain (e.g., leucine zipper motif) or via a cross-linking agent (e.g., chemical cross linker). Thus, antibodies of the invention include multimeric forms, for example, dimers, trimers, tetramers or higher order human, humanized and chimeric antibody oligomers. Such antibody multimers typically exhibit increased avidity for M2 in comparison to monomeric antibody.

Antibodies of the invention further include one or more heterologous domains that impart a distinct function or activity on a human or humanized antibody that binds M2. Antibodies that include an amino acid heterologous domain when one or more amino acids are distinct from the antibody (i.e., they are not a part of the native antibody). In one embodiment, a heterologous domain comprises a binding protein (e.g., receptor or ligand binding), an enzyme activity, a drug, an antiviral, a toxin, an immune-modulator, a detectable moiety or a tag. In one aspect, the binding protein comprises an antibody having a different binding specificity or affinity than human, humanized or chimeric antibody that specifically binds to influenza protein M2. Thus, the invention further provides multi-specific and multi-functional antibodies (e.g., bispecific and bifunctional antibodies, such as antibodies that bind to two or more antigens or that have two or more functions or activities, respectively).

Antibodies of the invention can bind to influenza protein M2, optionally present on one or more influenza strains or isolates. Thus, the antibodies have one or more effects on M2 or influenza virus infectivity, replication, proliferation, titre, severity or duration of one or more symptoms or complications associated with influenza, or susceptibility of influenza virus infection, i.e., anti-influenza virus activity. In one embodiment, a human, humanized or chimeric antibody inhibits infection of a cell in vitro or in vivo, or inhibits influenza binding of a cell in vitro or in vivo, by one or more influenza strains or isolates. In another embodiment, a human, humanized or chimeric antibody reduces influenza virus titer or an amount of an influenza viral protein of one or more influenza strains or isolates. In yet another embodiment, a human, humanized or chimeric antibody inhibits or prevents increases in influenza virus titer or an amount of an influenza viral protein of one or more influenza strains or isolates. In still another embodiment, a human, humanized or chimeric antibody protects a subject from infection or decreases susceptibility of the subject to infection by one or more influenza strains or isolates. In a further embodiment, a human, humanized or chimeric antibody decreases one or more symptoms or complications associated with infection by one or more influenza strains or isolates (e.g., chills, fever, cough, sore throat, nasal congestion, sinus congestion, nasal infection, sinus infection, body ache, head ache, fatigue, pneumonia, bronchitis, ear infection, ear ache or death). In various aspects, human, humanized or chimeric antibody is administered systemically (e.g., intravenous injection, subcutaneous injection, intravenous infusion, intramuscular injection), or locally to mucosal tissue (e.g., nasal passages, sinuses, throat, larynx, esophagus, ear or ear canal) or lung of a subject. In various aspects, the influenza is influenza A, and an influenza A strain is selected from A/PR/8/34 or A/HK/8/68, or selected from H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3.

Host cells that express invention human, humanized and chimeric antibodies are also provided. Cells include but are not limited to bacteria, yeast, plant, animal (e.g., mammalian cells such as hybridoma cell lines and CHO cell lines) as well as whole organisms such as non-human animals and plants that express invention human, humanized or chimeric antibodies.

Nucleic acids encoding antibodies of the invention, including subsequences and variants thereof, are further provided.

In particular embodiments, a nucleic acid encodes an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No.; American Type Culture Collection, Manassas, Va., USA). In additional particular embodiments, a nucleic acid encodes a heavy-chain variable sequence or a light-chain variable sequence as set forth in SEQ ID NO:26 and SEQ ID NO:27, SEQ ID NO:28 and SEQ ID NO:29, SEQ ID NO:30 and SEQ ID NO:31. Nucleic acids include vectors for cloning or other genetic manipulation of the nucleic acid or for expression in solution, in a cell, or in any organism.

Combination compositions including antibodies of the invention are also provided. In one embodiment, a composition includes human, humanized or chimeric antibody that binds influenza M2 protein and an antiviral agent. In another embodiment, a composition includes a human, humanized or chimeric antibody that binds influenza M2 protein and an agent that inhibits one or more symptoms or complications associated with influenza infection (e.g., chills, fever, cough, sore throat, nasal congestion, body ache, head ache, fatigue, pneumonia, bronchitis, sinus infection or ear infection).

Pharmaceutical compositions including antibodies of the invention and a pharmaceutically acceptable carrier or excipient are provided. In one embodiment, a carrier is suitable for administration to mucosal tissue (e.g., nasal passages, sinuses, throat, larynx, esophagus) or lung of a subject.

Kits that include one or more antibodies of the invention are also provided. In one embodiment, a kit includes instructions for treating (prophylaxis or therapeutic), inhibiting, preventing, decreasing susceptibility to, or reducing one or more symptoms or complications associated with influenza virus infection of a subject by one or more influenza strains or isolates. In another embodiment, a kit includes an article of manufacture, such as for delivery of antibody to mucosal tissue, such as an aerosol, spray or squeeze bottle, suitable for inhalation or nasal administration to a subject. In yet another embodiment, the kit or article of manufacture includes an antiviral agent (e.g., an antibody or a drug) or an agent that inhibits one or more symptoms or complications associated with influenza infection.

Methods for treating influenza infection of a subject are provided. In one embodiment, a method includes administering to the subject an amount of a human, humanized or chimeric antibody that specifically binds influenza M2 effective to treat influenza infection of the subject. In various aspects, the antibody is administered prior to, or substantially contemporaneously with or following infection of the subject, i.e., therapeutic treatment. In another aspect, the antibody provides a therapeutic benefit. In various aspects, a therapeutic benefit includes reducing or decreasing one or more symptoms or complications of influenza infection, virus titer, virus replication or an amount of a viral protein of one or more influenza strains. Symptoms or complications of influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death. In still another aspect, a therapeutic benefit includes hastening a subject's recovery from influenza infection.

Methods for inhibiting infection of a subject by one or more influenza strains or isolates are also provided. In one embodiment, a method includes administering to the subject an amount of a human, humanized or chimeric antibody that specifically binds influenza M2 effective to inhibit infection of the subject or reduce susceptibility of the subject to influenza infection by one or more influenza strains or isolates. In various aspects, the antibody is administered prior to (prophylaxis), substantially contemporaneously with or following infection of the subject. In another aspect, the antibody provides a therapeutic benefit. In various aspects, a therapeutic benefit includes reducing or decreasing onset or severity of one or more symptoms or complications of influenza infection (e.g., chills, fever, cough, sore throat, nasal congestion, sinus congestion, nasal infection, sinus infection, body ache, head ache, fatigue, pneumonia, bronchitis, ear infection or ear ache), virus titer or an amount of a viral protein of one or more influenza strains or isolates, susceptibility of a subject to infection by one or more influenza strains or isolates or hastening recovery of the subject from influenza virus infection or a symptom or complication thereof.

Methods for preventing an increase in influenza virus titer, virus replication, virus proliferation or an amount of an influenza viral protein in a subject are further provided. In one embodiment, a method includes administering to the subject an amount of a human, humanized or chimeric antibody that specifically binds influenza M2 effective to prevent an increase in influenza virus titer, virus replication or an amount of an influenza viral protein of one or more influenza strains or isolates in the subject.

Methods for protecting a subject from infection or decreasing susceptibility of a subject to infection by one or more influenza strains or isolates, i.e., prophylactic methods, are additionally provided. In one embodiment, a method includes administering to the subject an amount of a human, humanized or chimeric antibody that specifically binds influenza M2 effective to protect the subject from infection, or effective to decrease susceptibility of the subject to infection, by one or more influenza strains or isolates. In one aspect, the protection includes reducing or decreasing influenza infection or one or more symptoms or complications associated with influenza infection (e.g., chills, fever, cough, sore throat, nasal congestion, sinus congestion, nasal infection, sinus infection, body ache, head ache, fatigue, pneumonia, bronchitis, ear infection or ear ache).

Methods of the invention can be practiced with antibody as set forth herein, such as antibody that specifically binds to a sequence (or two or more sequences) that includes or consists of SLLTEVETPIRNEWGCRCNDSSD (M2, SEQ ID NO:1), a subsequence thereof or an amino acid variant thereof (e.g., an amino acid substitution, insertion, deletion or addition), such as

```
SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)
```

-continued

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
and

SLLPEVETHTRNGWGCRCSDSSD; (M2PHTGS; SEQ ID NO: 22)

antibodies having the binding specificity or binding affinity of an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA); antibodies produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA); antibodies that specifically bind to one or more of M2TGEKS (SEQ ID NO:10), M2TDGEKS (SEQ ID NO:15), M2LTGEKS (SEQ ID NO:9) or M2TGE (SEQ ID NO:19), as determined under certain assay conditions; antibodies that bind to a minimal binding sequence, such as a sequence that is the same or substantially the same as LLTEVETPIRNEWGC (SEQ ID NO:25); SLLTEVETPIRNEWGC (SEQ ID NO:23); or TPIRNE (SEQ ID NO:24), or the same or substantially the same as the minimal binding sequence to which antibody produced by the hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA,), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA) binds; and antibodies that do not specicially bind to a sequence LTEVETPIRNEW (SEQ ID NO:71) and/or EVETPIRN (SEQ ID NO:72).

Methods of the invention, including therapeutic, diagnostic and purification/isolation are applicable to any influenza strain/isolate or combination of strains/isolates. In various embodiments, the influenza is influenza A, and an influenza A strain is selected from A/PR/8/34 or A/HK/8/68, or selected from H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3.

Methods for producing human M2 antibodies are provided. In one embodiment, a method includes, administering M2 or an immunogenic fragment thereof to an animal (e.g., a non-human animal) capable of expressing human immunoglobulin; screening the animal for expression of human M2 antibody; selecting an animal that produces a human M2 antibody; isolating an antibody from the animal producing human M2 antibody; and determining whether the human M2 antibody binds to M2. In another embodiment, a method includes, administering M2 or an immunogenic fragment thereof to an animal (e.g., a non-human animal) capable of expressing human immunoglobulin; screening the animal for expression of human M2 antibody; selecting an animal producing an human M2 antibody; isolating spleen cells from the animal that produces human M2 antibody; fusing the spleen cells with a myeloma cell to produce a hybridoma; and screening the hybridoma for expression of a human M2 antibody. In various aspects, the M2 or immunogenic fragment thereof includes or consists of an M2 extracellular domain. In particular aspects, an M2 extracellular domain includes or consists of any of SLLTEVETPIRNEWGCRCNDSSD (SEQ ID NO:1), a subsequence thereof or an amino acid variant thereof (e.g., an amino acid substitution, insertion, deletion or addition), such as

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

-continued

```
SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
or

SLLPEVETHTRNGWGCRCSDSSD, (M2PHTGS; SEQ ID NO: 22)
or a sequence that is the same or substantially
the same as

LLTEVETPIRNEWGC;         (SEQ ID NO: 25)

SLLTEVETPIRNEWGC;        (SEQ ID NO: 23)
or

TPIRNE                   (SEQ ID NO: 24)
minimal binding sequences.
```

In yet another embodiment, a method includes, providing an animal (e.g., non-human animal) or cell that produces a human M2 antibody; and isolating an antibody from the animal or cell. In still another embodiment, a method includes, providing an animal (e.g., non-human animal) that produces a human M2 antibody; isolating spleen cells from the animal that produces human M2 antibody; fusing the spleen cells with a myeloma cell to produce a hybridoma; and screening the hybridoma for expression of a human M2 antibody. In various aspects, the animal or cell expresses an antibody having the binding specificity or the same or substantially the same binding affinity of the antibody produced by a hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), and L17 (ATCC Deposit No.; American Type Culture Collection, Manassas, Va., USA).

DESCRIPTION OF DRAWINGS

FIG. 1 illustrates nucleotide and amino acid sequences of variable region of immunoglobulin light chain of C40 antibody (C40Lv (SEQ ID NO:33 and 27)) and of heavy chain (C40Hv (SEQ ID NO:32 and 26)).

DETAILED DESCRIPTION

Figure 2:
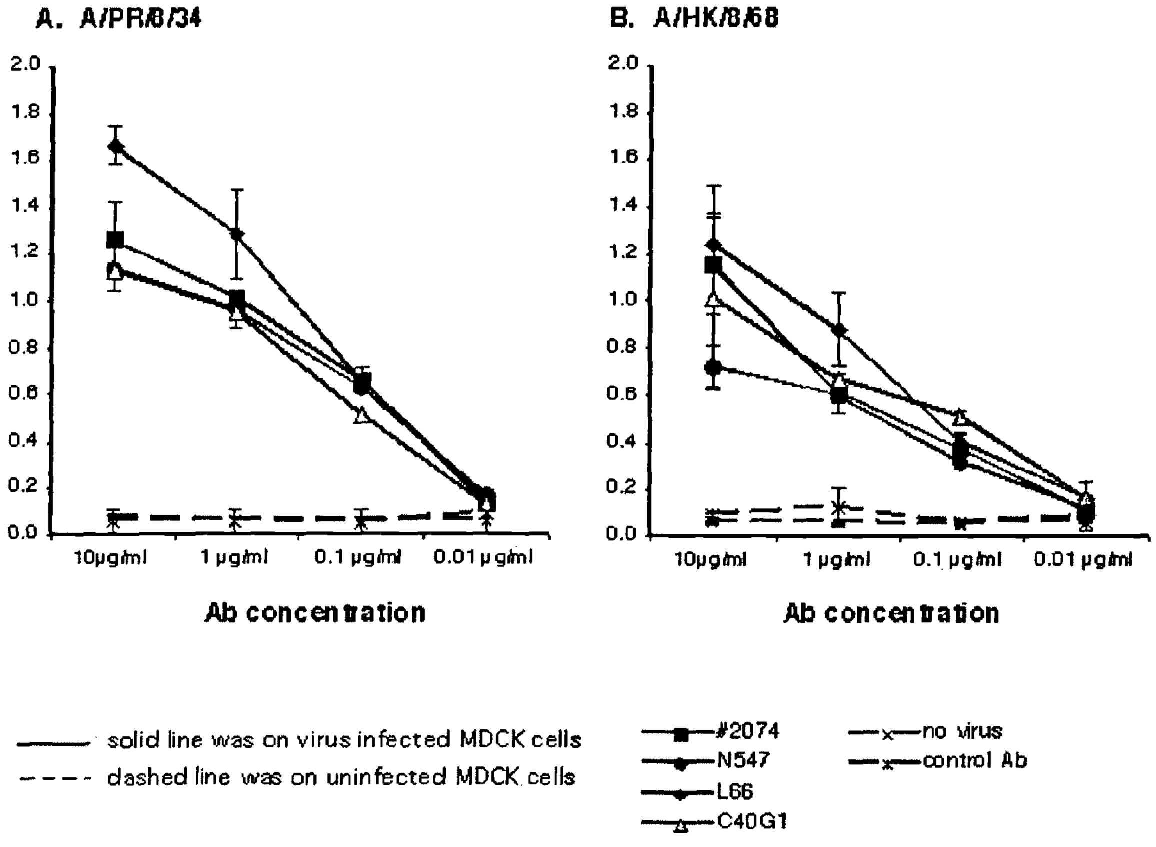
FIG. 2 shows that antibody nos. 2074, *N*547, L66 and C40G1 bind to M2 on A) A/PR/8/34 and B) A/HK/8/68 virus infected MDCK cells.

The invention is based at least in part on human, humanized and chimeric anti-M2 monoclonal antibodies. Several of the invention antibodies have broad reactivity against various M2 extracellular domain sequences based upon divergent influenza A virus strains. Passive transfer of an invention human anti-M2 monoclonal antibody protected animals from a lethal dose challenge of influenza A/PR/8/34, in both prophylactic (prior to virus infection) and therapeutic (following virus infection) mouse influenza models. Antibodies of the invention are therefore useful for treating a broad array of influenza strains or isolates. In addition, invention human antibodies are less likely to induce hypersensitivity from repeated administration and are more likely to remain in a subjects' (e.g., a human) body for a longer period of time.

Thus, in accordance with the invention, there are provided antibodies that specifically bind to influenza M2 protein, such as human, humanized and chimeric antibodies. In one embodiment, a human, humanized or chimeric antibody that specifically binds to influenza protein M2 extracellular domain is provided. In a particular aspect, an extracellular domain comprises the amino acid sequence SLLTEVETPIRNEWGCRCNDSSD (SEQ ID NO:1), a portion thereof or an amino acid variant thereof (e.g., an amino acid substitution, insertion, deletion or addition), such as

```
SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
or
```

-continued

SLLPEVETHTRNGWGCRCSDSSD. (M2PHTGS; SEQ ID NO: 22)

Additional antibodies of the invention include antibodies that bind to two or more (e.g., three, four, five, etc.) M2 proteins having different amino acid sequences, which may optionally be present on different influenza virus strains or isolates. Exemplary M2 sequences to which such antibodies can bind include wild-type M2, SLLTEVETPIRNEWGCRCNDSSD (SEQ ID NO: 1), and a subsequence thereof or an amino acid variant thereof, such as

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
or

SLLPEVETHTRNGWGCRCSDSSD. (M2PHTGS; SEQ ID NO: 22)

Antibodies of the invention include antibodies that bind to an influenza virus M2 sequence under certain assay conditions. In one embodiment, an antibody specifically binds to one or more of M2TGEKS (SEQ ID NO:10), M2TDGEKS (SEQ ID NO:15), M2LTGEKS (SEQ ID NO:9) or M2TGE (SEQ ID NO:19), as determined by a peptide based ELISA assay wherein the antibody is at a concentration of 10 μg/ml. In another embodiment, an antibody specifically binds to an influenza protein M2 extracellular domain, wherein the antibody has a binding activity (EC50) of less than $10^{-8}$ M for M2LTGEKS (SEQ ID NO:9) or M2TGEK (SEQ ID NO: 13), as determined by an ELISA assay of binding between the antibody and an M2LTGEKS-BSA or M2TGEK-BSA conjugate. In an additional embodiment, an antibody specifically binds to an influenza protein M2 extracellular domain, wherein the antibody has a binding activity (EC50) of less than $10^{-9}$M for M2LTGEKS (SEQ ID NO:9) or M2TGEK (SEQ ID NO:13), as determined by an ELISA assay of binding between the antibody and an M2LTGEKS-BSA or M2TGEK-BSA conjugate. In a further embodiment, an antibody specifically binds to an influenza protein M2 extracellular domain, wherein the antibody has a binding activity (EC50) of less than $10^{-8}$ M for M2LTGEKS (SEQ ID NO:9) or M2TGEK (SEQ ID NO:13), wherein the antibody has a binding activity (EC50) of greater than $10^{-8}$ M for one or more of M2TGS (SEQ ID NO:12) or M2TGE (SEQ ID NO:19), and wherein binding activity is determined by an ELISA assay of binding between the antibody and a M2LTGEKS-BSA, M2TGEK-BSA, M2TGS-BSA or M2TGE-BSA conjugate. In still another embodiment, an antibody specifically binds to an influenza protein M2 extracellular domain, wherein the antibody has a binding activity (EC50) of less than $10^{-9}$ M for M2LTGEKS (SEQ ID NO:9) or M2TGEK (SEQ ID NO: 13), wherein the antibody has a binding activity (EC50) of greater than $10^{-8}$ M for one or more of M2TGS (SEQ ID NO:12) or M2TGE (SEQ ID NO:19), and wherein binding activity is determined by an ELISA assay of binding between the antibody and a M2LTGEKS-BSA, M2TGEK-BSA, M2TGS-BSA or M2TGE-BSA conjugate. Such assay conditions are not the exclusive assay conditions under which antibodies of the invention may or may not bind to an M2 sequence as set forth herein or known to the skilled artisan.

The term "antibody" refers to a protein that binds to other molecules (antigens) via heavy and light chain variable domains, $V_H$ and $V_L$, respectively. "Antibody" refers to any immunoglobulin molecule, such as IgM, IgG, IgA, IgE, IgD, and any subclass thereof, such as $IgG_1$, $IgG_2$, $IgG_3$, $IgG_4$, etc. The term "antibody" also means a functional fragment or subsequence of immunoglobulin molecules, such as Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody ($(V_L\text{-}V_H)_2$ or $(V_H\text{-}V_L)_2$), triabody (trivalent), tetrabody (tetravalent), minibody ($(scFv\text{-}C_H3)_2$), bispecific single-chain Fv (Bis-scFv), IgGdeltaCH2, scFv-Fc or $(scFv)_2$-Fc, unless otherwise expressly stated.

The terms "M2 antibody" or "anti-M2 antibody" means an antibody that specifically binds to influenza M2 protein. Specific binding is that which is selective for an epitope present in M2 protein. That is, binding to proteins other than M2 is such that the binding does not significantly interfere with detection of M2, unless such other proteins have a similar or the same epitope present in M2 protein so as to be recognized by M2 antibody. Selective binding can be distinguished from non-selective binding using assays known in the art which include, for example, competition binding assays.

The term "isolated," when used as a modifier of an invention composition (e.g., antibodies, modified forms, subsequences, nucleic acids encoding same, etc.), means that the compositions are made by the hand of man or are separated from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms, such as polypeptide multimers, post-translational modifications (e.g., phosphorylation, glycosylation) or derivatized forms.

An "isolated" antibody can also be "substantially pure" when free of most or all of the materials with which it typically associates with in nature. Thus, an isolated molecule that also is substantially pure does not include polypeptides or polynucleotides present among millions of other sequences, such as antibodies of an antibody library or nucleic acids in a genomic or cDNA library, for example. A "substantially pure" molecule can be combined with one or more other molecules, Thus, "substantially pure" does not exclude combination compositions.

Exemplary antibodies of the invention are denoted as no. 2074 (produced by mouse B cell hybridomas ATCC Deposit No. PTA-4025; American Type Culture Collection, Manassas, Va., USA), deposited Jan. 31, 2002), 161 (produced by mouse B cell hybridomas ATCC Deposit No. PTA-4026; American Type Culture Collection, Manassas, Va., USA, deposited Jan. 31, 2002), N547 (produced by mouse B cell hybridomas ATCC Deposit No. PTA-5049; American Type Culture Collection, Manassas, Va., USA, deposited Mar. 11, 2003), L66 (produced by mouse B cell hybridomas ATCC Deposit No. PTA-5048; American Type Culture Collection, Manassas, Va., USA, deposited Mar. 11, 2003), C40G1 produced by Chinese Hamster Ovary cells ATCC Deposit No. PTA-5050; American Type Culture Collection, Manassas, Va., USA, deposited Mar. 11, 2003), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA).

Exemplary heavy-chain variable sequence and light-chain variable sequence is an amino acid sequence set forth in SEQ ID NO:26 and SEQ ID NO:27, SEQ ID NO:28 and SEQ ID NO:29; and SEQ ID NO:30 and SEQ ID NO:31, respectively.

As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced. As used herein, a specific name, numeral or other designation given to a hybridoma or other cell line, such as no. 2074, 161, N547, L66 and C40G1, also is used to refer to the name of antibody.

The term "human" when used in reference to an antibody, means that the amino acid sequence of the antibody is fully human. A "human M2 antibody" or "human anti-M2 antibody" therefore refers to an antibody having human immunoglobulin amino acid sequences, i.e., human heavy and light chain variable and constant regions that specifically bind to M2. That is, all of the antibody amino acids are human or exist in a human antibody. Thus, for example, an antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest,* $4^{th}$ Ed. US Department of Health and Human Services. Public Health Service (1987); and Chothia and Lesk *J. Mol. Biol.* 186:651 (1987)). A consensus sequence of human $V_H$ subgroup III, based on a survey of 22 known human $V_H$ III sequences, and a consensus sequence of human $V_L$ kappa-chain subgroup I, based on a survey of 30 known human kappa I sequences is described in Padlan *Mol. Immunol.* 31:169 (1994); and Padlan *Mol. Immunol.* 28:489 (1991)).

The term "humanized" when used in reference to an antibody, means that the amino acid sequence of the antibody has non-human amino acid residues (e.g., mouse, rat, goat, rabbit, etc.) of one or more determining regions (CDRs) that specifically bind to the desired antigen (e.g., M2) in an acceptor human immunoglobulin molecule, and one or more human amino acid residues in the Fv framework region (FR), which are amino acid residues that flank the CDRs. Human framework region residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. In addition, a humanized antibody may include residues, which are found neither in the human antibody nor in the donor CDR or framework sequences. For example, a framework substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332:323 (1988)). Antibodies referred to as "primatized" in the art are within the meaning of "humanized" as used herein, except that the acceptor human immunoglobulin molecule and framework region amino acid residues may be any primate residue, in addition to any human residue.

As used herein, the term "chimeric" and grammatical variations thereof, when used in reference to an antibody, means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine variable region). Thus, a chimeric antibody is a molecule in which different portions of the antibody are of different species origins. Unlike a humanized antibody, a chimeric antibody can have the different species sequences in any region of the antibody. An example of a chimeric antibody is antibody no. 2074, which has mouse lambda light chain and human gamma heavy chain.

As used herein, the terms "M2," "M2 protein," "M2 sequence" and "M2 domain" refer to all or a portion of an M2 protein sequence (e.g., a subsequence such as the extracellular domain) isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences.

The term "M2 peptide" refers to the extracellular amino acid sequence of full length M2 protein. An exemplary M2 peptide consists of the sequence SLLTEVETPIRNEWGCRCNDSSD (SEQ ID NO:1). Additional exemplary M2 peptide sequences consist of:

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

-continued

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
and

SLLPEVETHTRNGWGCRCSDSSD. (M2PHTGS; SEQ ID NO: 22)

M2 antibodies of the invention include antibodies having kappa or lambda light chain sequences, either full length as in naturally occurring antibodies, mixtures thereof (i.e, fusions of kappa and lambda chain sequences), and subsequences thereof, as described herein. Naturally occurring antibody molecules contain two kappa and two lambda light chains. The primary difference between kappa and lambda light chains is in the sequences of the constant region.

M2 antibodies of the invention can belong to any antibody class or subclass. Exemplary subclasses for IgG are $IgG_1$, $IgG_2$, $IgG_3$ and $IgG_4$. Invention antibodies include antibodies having either or both of antibody-dependent cell-mediated cytotoxicity (ADCC) and complement-mediated cytotoxicity (CDC) activities, which are expected for effective treatment of influenza A (i.e., killing influenza A infected cells or influenza A virus). IgG subclass IgG, is known to exhibit both ADCC and CDC activities.

Invention M2 antibodies include antibodies having the binding specificity of the M2 antibodies exemplified herein, e.g., having the binding specificity of an antibody produced by a hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA). In one embodiment, an antibody binds to the same epitope as an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) and L17 (ATCC Deposit No. American Type Culture Collection, Manassas, Va., USA). In particular aspects, an antibody binds to the same epitope, or the same or substantially the same minimal binding sequence, as an antibody produced by a hybridoma or CHO cell line denoted as any of nos. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA). In additional particular aspects, an antibody binds to the same epitope, or the same or substantially the same minimal binding sequence, as an antibody that includes a heavy (H) or light (L) chain sequence, or a subsequence thereof, produced by a hybridoma or CHO cell line denoted as any of nos. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA). In further particular aspects, an antibody binds to the same epitope, or the same or substantially the same minimal binding sequence, as an antibody that includes a heavy-chain variable sequence or a light-chain variable sequence as set forth in SEQ ID NO:26 and SEQ ID NO:27, SEQ ID NO:28 and SEQ ID NO:29, SEQ ID NO:30 and SEQ ID NO:31. Exemplary epitopes (amino acid sequences) include all or a portion of a minimal binding sequence SLLTEVETPIRNEWGC (SEQ ID NO:23); TPIRNE (SEQ ID NO:24); and LLTEVETPIRNEWGC (SEQ ID NO:25).

The term "binding specificity," when used in reference to an antibody, means that the antibody specifically binds to all or a part of the same antigenic epitope as the reference antibody. Thus, an M2 antibody having the binding specificity of the antibody denoted as no. 2074 specifically binds to all or a part of the same epitope as the M2 antibody denoted as no. 2074; an M2 antibody having the binding specificity of the antibody denoted as 161 specifically binds to all or a part of the same epitope as the M2 antibody denoted as 161; an M2 antibody having the binding specificity of the antibody denoted as N547 specifically binds to all or a part of the same epitope as the M2 antibody denoted as N547; an M2 antibody having the binding specificity of the antibody denoted as L66 specifically binds to all or a part of the same epitope as the M2 antibody denoted as L66; an M2 antibody having the binding specificity of the antibody denoted as C40G1 specifically binds to all or a part of the same epitope as the M2 antibody denoted as C40G1; and so on and so forth.

A part of an antigenic epitope means a subsequence or a portion of the epitope. For example, if an epitope includes 8 contiguous amino acids, a subsequence and, therefore, a part of an epitope may be 7 or fewer amino acids within this 8 amino acid sequence epitope. In addition, if an epitope includes non-contiguous amino acid sequences, such as a 5 amino acid sequence and an 8 amino acid sequence which are not contiguous with each other, but form an epitope due to protein folding, a subsequence and, therefore, a part of an epitope may be either the 5 amino acid sequence or the 8 amino acid sequence alone.

Antibodies having the binding specificity of the M2 antibodies exemplified herein compete with the binding of no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA). Antibodies of the invention therefore include antibodies that compete for binding to one or more of

```
SLLTEVETPRINEWGCRCNDSSD; (SEQ ID NO: 1)

SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)

SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
or

SLLPEVETHTRNGWGCRCSDSSD, (M2PHTGS; SEQ ID NO: 22)
or a sequence that includes or consists of all or a
portion of a sequence set forth as
SLLTEVETPRINEWGC;         (SEQ ID NO: 23)

TPIRNE;                   (SEQ ID NO: 24)
or

LLTEVETPIRNEWGC.          (SEQ ID NO: 25)
```

An antibody of the invention having binding specificity of the M2 antibodies exemplified herein may be characterized by any method known in the art for determining competitive binding, for example, the immunoassays disclosed herein. Because the binding affinity may differ from the exemplified antibodies (i.e., have greater or less affinity), the antibodies will vary in their ability to compete for binding to M2. In particular embodiments, the antibody competitively inhibits binding by at least 95%, at least 90%, at least 85%, at least 80%, at least 75%, at least 70%, at least 65%, at least 60%, at least 55%, at least 50%, at least 45%, at least 40%, at least 35%, or at least 30%, or less.

Epitopes typically are short amino acid sequences, e.g. about five to 15 amino acids in length. Epitopes may be identified, as set forth in Example 3. Systematic techniques for identifying epitopes are also known in the art and are described, for example, in U.S. Pat. No. 4,708,871. Briefly, a set of overlapping oligopeptides derived from an M2 antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-M2 monoclonal antibody. Alternatively, phage display peptide library kits (New England BioLabs) are currently commercially available for epitope mapping. Using these methods, binding affinity for every possible subset of consecutive amino acids may be determined in order to identify the epitope that a particular antibody binds. Epitopes may also be identified by inference when epitope length peptide sequences are used to immunize animals from which antibodies that bind to the peptide sequence are obtained.

Exemplary epitopes (amino acid sequences) of M2 extracellular domain for N547, are within a minimal binding sequence LLTEVETPIRNEWGC (SEQ ID NO:25); for L66, within a minimal binding sequence SLLTEVETPIRNEWGC (SEQ ID NO:23); and for C40G1, within a minimal binding sequence TPIRNE (SEQ ID NO:24).

As used herein, the term “minimal binding sequence,” when used in reference to an M2 peptide, means a contiguous amino acid sequence of M2 peptide (e.g., SEQ ID NO:1) that is minimally required for binding of the anti-M2 antibody. A minimal binding sequence is determined by creating various peptides consisting of N-terminal truncated M2 peptide, and C-terminal truncated M2 peptide, and measuring antibody binding to these peptides based on the method described in Example 3. Thus, a minimal binding sequence represents the N-terminal and C-terminal borders of a sequence within M2 peptide that is minimally required for antibody binding to the peptide.

A minimal binding sequence (MBS) contains all or a part of an epitope to which the M2 antibody paratope binds, sufficient to mediate anti-M2 antibody binding. An epitope contains 3-4 or more amino acid sequences, contiguous or non-contiguous, within a minimal binding sequence, that mediates antibody binding. As disclosed in Example 3, exemplary minimal binding sequences include for N547, LLTEVETPIRNEWGC (SEQ ID NO:25), for L66, SLLTEVETPIRNEWGC (SEQ ID NO:23), and for C40G1, TPIRNE (SEQ ID NO:24).

The term “the same minimal binding sequence” means that the minimal binding sequence of an antibody is identical to that of a reference antibody. The term “substantially same minimal binding sequence,” and grammatical variations thereof, means a minimal binding sequence of an antibody having a single amino acid addition or deletion at N-terminus and/or C-terminus as compared to the minimal binding sequence of the reference antibody.

As a non-limiting illustration of antibodies that bind to the same or substantially the same minimal binding sequence, the minimal binding sequence for N547 is LLTEVETPIRNEWGC (SEQ ID NO:25). Thus, an antibody having the same minimal binding sequence as N547 will have the LLTEVETPIRNEWGC (SEQ ID NO:25) minimal binding sequence. A substantially the same minimal binding sequence of LLTEVETPIRNEWGC (SEQ ID NO:25) could be, for example, LTEVETPIRNEWGC, LLTEVETPIRNEWG, SLLTEVETPIRNEWGC, LLTEVETPIRNEWGCR, LTEVETPIRNEG, etc. Thus, an antibody that binds to substantially the same minimal binding sequence as N547 could therefore bind to, for example, LTEVETPIRNEWGC, LLTEVETPIRNEWG, SLLTEVETPIRNEWGC, LLTEVETPIRNEWGCR, LTEVETPIRNEWG, etc.

The invention therefore provides antibodies having the same or substantially the same minimal binding sequence as anti-M2 antibodies exemplified herein, for example, N547, L66 and C40G1. Accordingly, antibodies of the invention therefore include antibodies (e.g., human, humanized and chimeric) that bind to a sequence that is the same or substantially the same as LLTEVETPIRNEWGC (SEQ ID NO:25); SLLTEVETPIRNEWGC (SEQ ID NO:23); or TPIRNE (SEQ ID NO:24), as well as antibodies that specifically bind to a minimal binding sequence that is the same or substantially the same as the minimal binding sequence to which antibody produced by the hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA,), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA) binds.

Antibodies of the invention optionally have exemplary minimal binding sequences distinct from antibody 14C2 minimal binding sequence LTEVETPIRNEW (SEQ ID NO:71), or distinct from an antibody that has an apparent minimal binding sequence EVETPIRN (SEQ ID NO:72). Thus, antibodies that bind to minimal binding sequence LTEVETPIRNEW (SEQ ID NO:71) or EVETPIRN (SEQ ID NO:72) may be excluded.

To obtain anti-M2 antibodies that bind to a sequence that is the same or substantially same as a minimal binding sequence, or an eptiope of another anti-M2 antibody, antibodies that compete for the binding of the antibody to M2 peptide (e.g., any of SEQ ID NOs:1-22), or a minimal binding sequence or an eptiope, are screened using a conventional competition binding assay. Screened antibodies are selected that have the same or substantially same minimal binding sequence as a reference antibody, as described in Example 3. As a non-limiting example, for N547, at the first step, antibodies that compete with N547 in the binding to M2 peptide (e.g., any of SEQ ID NOs:1-22) are screened among anti-M2 antibodies using a competition binding assay. In the second step, antibodies that compete for N547 binding to M2 are selected for the ability to bind to the same or substantially same minimal binding sequence as N547.

Invention M2 antibodies also include human, humanized and chimeric antibodies having the same binding affinity and having substantially the same binding affinity as the M2 antibodies exemplified herein. For example, an M2 antibody of the invention may have an affinity greater or less than 2-5, 5-10, 10-100, 100-100 or 1000-10,000 fold affinity as the reference antibody for binding to any of SEQ ID NOs:1-22, or a minimal binding sequence or an eptiope. Thus, in additional embodiments the invention provides M2 antibodies having the same binding affinity and having substantially the same binding affinity as the antibodies denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection. Manassas, Va., USA), and C40, L30, L40, S212, S80, S900 (ATCC Deposit Nos., respectively; American Type Culture Collection, Manassas, Va., USA). In various aspects, the binding affinity is within about 5 to 100 fold of the reference antibody, or within about 5 to 5000 fold of the reference antibody.

As used herein, the term "the same," when used in reference to antibody binding affinity, means that the dissociation constant ($K_D$) is within about 5 to 100 fold of the reference antibody (5-100 fold greater affinity or less affinity than the reference antibody). The term "substantially the same" when used in reference to antibody binding affinity, means that the dissociation constant ($K_D$) is within about 5 to 5000 fold of the reference antibody (5-5000 fold greater affinity or less affinity than the reference antibody).

Additional antibodies included in the invention have a binding specificity of the antibodies denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA), and binding affinity for M2 with a dissociation constant (Kd) less than $5\times10^{-2}$ M, $10^{-2}$ M, $5\times10^{-3}$ M, $10^{-3}$ M $5\times10^{-4}$ M, $10^{-4}$M $5\times10^{-5}$ M, $10^{-5}$ M $5\times10^{-6}$ M, $10^{-6}$ M $5\times10^{-7}$ M, $10^{-7}$ M $5\times10^{-8}$ M, $10^{-8}$ M$5\times10^{-9}$ M, $10^{-9}$ M $5\times10^{-10}$ M, $10^{-10}$ M $5\times10^{-11}$ M, $10^{-11}$ M $5\times10^{-12}$ M, $10^{-12}$ M $5\times10^{-13}$ M, $10^{-13}$ M$5\times10^{-14}$ M, $10^{-14}$ M $5\times10^{-15}$ M, and $10^{-15}$ M. Antibodies further included in the invention bind to an epitope to which the antibodies denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA) bind. Yet additional antibodies have an $EC_{50}$ less than 2.0 to 3.0, 1.0 to 2.0, 0.5 to 1.0, 0.1 to 0.5 or less than 0.1 μg/ml (e.g., 0.05 to 0.1 μg/ml) for inhibiting influenza A virus infection of MDCK cells, as determined by a cell based-ELISA assay.

Invention M2 antibodies include antibodies having at least a part of one or more anti-influenza activities of the M2 antibodies exemplified herein (e.g., inhibit influenza virus infection of a cell in vitro or in vivo, inhibit influenza virus proliferation or replication, decrease one or more symptoms or complications associated with influenza virus infection, decrease susceptibility to influenza virus infection, etc.). Thus, in additional embodiments the invention provides M2 antibodies having at least a part of one or more anti-influenza activities of an antibody denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), or C40, L30, L40, S212, S80, S900 (ATCC Deposit Nos., respectively; American Type Culture Collection, Manassas, Va., USA).

The term "activity," when used in comparing an antibody to a reference antibody, means that the antibody has at least a part of an activity as the reference antibody, for example, binding affinity, binding specificity or anti-influenza activity. Thus, an antibody having an activity of the M2 antibody denoted as N547 has at least a part of one or more activities of the M2 antibody denoted as N547; an antibody having an activity of the M2 antibody denoted as L66 has at least a part of one or more activities of the M2 antibody denoted as L66; an antibody having an activity of the M2 antibody denoted as C40G1 has at least a part of one or more activities of the M2 antibody denoted as C40G1; and so on and so forth. The term "at least a part" means that the antibody may have lesser or greater activity but the antibody retains at least some of the activity of the reference M2 antibody, e.g., at least partial binding affinity for M2, at least partial anti-influenza activity, etc.

Antibodies having an activity of exemplified human M2 antibodies can be identified using binding assay with plate-bound M2 peptide as a coating antigen (ELISA), binding assay to M2 protein on viral infected MDCK cells (cell based ELISA), and specific inhibition of antibody binding to M2 on the viral infected MDCK cells with M2 peptide (M2 extracellular portion). Additional assays include in vitro cell infectivity assays with influenza virus (Zebedee et al. *J. Virology* 62:2762 (1988)) as well as in vivo animal assays as set forth in Examples 1, 3 and 4.

Methods of producing human antibodies are disclosed herein and known in the art. For example, as disclosed herein M2 protein conjugated to KLH or BSA was used to immunize human transchromosomic KM Mice™ (WO 02/43478) or HAC mice (WO 02/092812). KM Mice™ or HAC mice express human immunoglobulin genes. Using conventional hybridoma technology, splenocytes from immunized mice that were high responders to M2 antigen were isolated and fused with myeloma cells. Twelve monoclonal antibodies were obtained, denoted no. 2074, C40, L17, L30, L40, L66, N547, S212, S80, S900, F1, and F2, that reacted to M2 peptide and/or M2-BSA conjugates, but did not bind to the BSA or KLH carriers. An overview of the technology for producing human antibodies is described in Lonberg and Huszar, *Int. Rev. Immunol.* 13:65 (1995). Transgenic animals with one or more human immunoglobulin genes (kappa or lambda) that do not express endogenous immunoglobulins are described, for example in, U.S. Pat. No. 5,939,598. Additional methods for producing human antibodies and human monoclonal antibodies are described (see, e.g., WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

M2 Monoclonal antibodies can also be readily generated using other techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Suitable techniques that additionally may be employed in the method including M2 affinity purification, non-denaturing gel purification, HPLC or RP-HPLC, purification on protein A column, or any combination of these techniques. The antibody isotype can be determined using an ELISA assay, for example, a human Ig can be identified using mouse Ig-absorbed anti-human Ig.

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Molecular Immunol.* 28:489 (1991); Studnicka et al., *Protein Engineering* 7:805 (1994); Roguska. et al., *Proc. Nat'l. Acad. Sci. USA* 91:969 (1994)), and chain shuffling (U.S. Pat. No. 5,565,332). Human consensus sequences (Padlan *Mol. Immunol.* 31:169 (1994); and Padlan *Mol. Immunol.* 28:489 (1991)) have previously used to humanize antibodies (Carter et al. *Proc. Natl. Acad. Sci. USA* 89:4285 (1992); and Presta et al. *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., (1989) *J. Immunol. Methods* 125:191; and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

M2 protein suitable for generating antibodies can be produced by any of a variety of standard protein purification or recombinant expression techniques known in the art. For example, M2 can be produced by standard peptide synthesis techniques, such as solid-phase synthesis. A portion of the protein may contain an amino acid sequence such as a T7 tag or polyhistidine sequence to facilitate purification of expressed or synthesized M2. M2 may be expressed in a cell and protein produced by the cells may be purified. M2 protein may be expressed as a part of a larger protein by recombinant methods.

Forms of M2 suitable for generating an immune response include peptide subsequences of full length M2 (e.g., typically four to five amino acids or more in length). Additional forms of M2 include M2 containing preparations or extracts, partially purified M2 as well as cells or viruses that express M2 or preparations of such expressing cells or viruses.

Animals which may be immunized include mice, rabbits, rats, sheep, goats, or guinea pigs; such animals may be genetically modified to include human IgG gene loci. Additionally, to increase the immune response, M2 can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of M2 antigen preparation, and may be at regular or irregular intervals.

Thus, in another embodiment, the invention provides methods of producing human M2 antibodies, including antibodies having one or more an anti-influenza activities, such as inhibiting influenza virus infection, replication, proliferation, or titre, or inhibiting increases in virus replication, proliferation or titre, or reducing the severity or duration of one or more symptoms or complications associated with influenza infection, or susceptibility to infection, or having broad reactivity against various influenza virus strains or isolates. In one embodiment, a method includes administering M2 or an immunogenic fragment thereof to an animal (e.g., a mouse) capable of expressing human immunoglobulin; screening the animal for expression of human M2 antibody; selecting an animal that produces a human M2 antibody; isolating an antibody from the animal that produces human M2 antibody; and determining whether the human M2 antibody binds to M2. In another embodiment, a method includes administering M2 or an immunogenic fragment thereof to an animal (e.g., a mouse) capable of expressing human immunoglobulin; isolating spleen cells from the mouse that produces human M2 antibody; fusing the spleen cells with a myeloma cell to produce a hybridoma; and screening the hybridoma for expression of a human M2 antibody that has an anti-influenza activity.

The invention further provides M2 antibodies that have been modified. Examples of modifications include one or more amino acid substitutions, additions or deletions of the antibody, provided that the modified antibody has all or at least part of an activity of unmodified M2 antibody, e.g., an anti-influenza activity.

A particular example of a modification is where an antibody of the invention is altered to have a different isotype or subclass by, for example, substitution of the heavy chain constant region (see, for example, Example 2). An alteration of the Ig subclass of an M2 antibody C40 from IgG4 to IgG1 results in an improvement in an anti-influenza activity. Thus, modifications include deleting large regions of amino acid sequences from an invention antibody and substituting the region with another amino acid sequence, whether the sequence is greater or shorter in length than the deleted region.

Additional modifications of M2 antibodies included in the invention are antibody derivatives i.e., the covalent attachment of any type of molecule to the antibody. Specific examples of antibody derivatives include antibodies that have been glycosylated, acetylated, phosphorylated, amidated, formylated, ubiquitinated, and derivatization by protecting/blocking groups and any of numerous chemical modifications.

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc.

Modifications include an activity or function of a reference composition (e.g., specific binding to M2). A modified protein can have an amino acid substitution, addition or deletion (e.g., 1-3, 3-5, 5-10 or more residues). In a particular non-limiting example, the substitution is a conservative amino acid substitution, e.g., within or outside of a CDR.

Amino acid substitutions can be conservative or non-conservative and may be in the constant or variable region of the antibody. One or a few conservative amino acid substitutions in constant or variable regions (within or outside of a CDR) are likely to be tolerated. Non-conservative substitution of multiple amino acids in hypervariable (CDR) regions is likely to affect binding activity, specificity or antibody function or activity. The effect of a particular substitution can be assayed in order to identify antibodies retaining at least a part of the binding activity, specificity or antibody function or activity of unsubstituted antibody. For example, an amino acid substitution in a hypervariable region may be assayed for binding activity or specificity. Such antibodies having amino acid substitutions are included so long as at least a part of binding specificity, binding affinity, or an anti-influenza activity of unmodified human M2 antibody is retained by the substituted antibody.

A "conservative substitution" means the replacement of one amino acid by a biologically, chemically or structurally similar residue. Biologically similar means that the substitution is compatible with biological activity, e.g., specifically binds to M2. Structurally similar means that the amino acids have side chains with similar length, such as alanine, glycine and serine, or similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Modified antibodies include amino acid sequence with 50%, 60%, 70%, 75%, 80%, 85%, 90%, 95%, 96%, 97%, 98%, or more identity to a sequence of a monoclonal antibody denoted as no. 2074, C40, L17, L30, L40, L66, N547, S212, S80, S900, F1, and F2. The identity can be over a defined area of the protein, e.g., within or outside of a variable region such as a CDR.

The term "identity" and grammatical variations thereof, mean that two or more referenced entities are the same. Thus, where two antibody sequences are identical, they have the same amino acid sequence. "Areas of identity" means that a portion of two or more referenced entities are the same. Thus, where two antibody sequences are identical over one or more sequence regions they share identity in these regions. The term "substantial identity" means that the identity is structurally or functionally significant. That is, the identity is such that the molecules are structurally identical or have at least one of the same functions (e.g., specific binding to M2) even though the molecules are different.

Due to variation in the amount of sequence conservation between structurally and functionally related proteins, the amount of sequence identity for substantial identity will depend upon the protein, the region and any function of that region. Although there can be as little as 30% sequence identity for proteins to have substantial identity, typically there is more, e.g., 50%, 60%, 75%, 85%, 90%, 95%, 96%, 97%, 98%, identity to a reference sequence. For nucleic acid sequences, 50% sequence identity or more typically constitutes substantial homology, but again can vary depending on the comparison region and its function, if any.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al. (1990) *J. Mol. Biol.* 215:403-10, publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, or BLOSUM 62.

Monoclonal M2 antibodies of the invention include subsequences (e.g., fragments) and modified forms (e.g., sequence variants) as set forth herein. In particular embodiments, M2 antibody subsequences include an Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody $((V_L-V_H)_2$ or $(V_H-V_L)_2)$, triabody (trivalent), tetrabody (tetravalent), minibody $((scF_v-C_H3)_2)$, bispecific single-chain Fv (Bis-scFv), IgGdeltaCH2, scFv-Fc or (scFv)-2-Fc, fragments. In particular aspects, an Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody $((V_L-V_H)_2$ or $(V_H-V_L)_2)$, triabody (trivalent), tetrabody (tetravalent), minibody $((scFv-C_H3)_2)$, bispecific single-chain Fv (Bis-scFv), IgGdeltaCH2, scFv-Fc or (scFv)-2-Fc subsequence has the same binding affinity, substantially the same binding affinity, the same binding specificity, or one or more anti-influenza activities, e.g., efficacy in inhibiting influenza infection of a cell in vitro or in vivo as the reference M2 antibody (e.g., the full length or unmodified M2 antibody). M2-binding antibody subsequences, including single-chain antibodies, include variable region(s) alone or in combination with all or a portion of one or more of the following: hinge region, CH1, CH2, and CH3 domains. Also included are antigen-binding subsequences of any combination of variable region(s) with a hinge region, CH1, CH2, and CH3 domains.

M2 antibody subsequences (e.g., Fab, Fab', $F(ab')_2$, Fv, Fd, single-chain Fv (scFv), disulfide-linked Fvs (sdFv), $V_L$, $V_H$, trispecific ($Fab_3$), bispecific ($Fab_2$), diabody $((V_L-V_H)_2$ or $(V_H-V_L)_2)$, triabody (trivalent), tetrabody (tetravalent), minibody $((scFv-C_H3)_2)$, bispecific single-chain Fv (Bis-scFv), IgGdeltaCH2, scFv-Fc or (scFv)-2-Fc) of the invention can be prepared by proteolytic hydrolysis of the antibody, for example, by pepsin or papain digestion of whole antibodies. The terms "functional subsequence" and "functional fragment" when referring to an antibody of the invention refers to a portion of an antibody that retains at least a part of one or more functions or activities as the intact reference antibody.

Antibody fragments can be produced by enzymatic cleavage with pepsin provide a 5S fragment denoted $F(ab')_2$. This fragment can be further cleaved using a thiol reducing agent to produce 3.5S Fab' monovalent fragments. Alternatively, an enzymatic cleavage using pepsin produces two monovalent Fab' fragments and the Fc fragment directly (see, e.g., Goldenberg, U.S. Pat. Nos. 4,036,945 and 4,331,647; and Edelman et al. *Methods in Enymology* 1:422 (1967)). Other methods of cleaving antibodies, such as separation of heavy chains to form monovalent light-heavy chain fragments, further cleavage of fragments, or other enzymatic or chemical may also be used. Genetic techniques include expression of all or a part of the M2 antibody gene into a host cell such as Cos cells or *E. coli*. The recombinant host cells synthesize intact or single antibody chain, such as a scFv (see, e.g., Whitlow et al., In: *Methods: A Companion to Methods in Enzymology* 2:97 (1991), Bird et al., *Science* 242:423 (1988); and U.S. Pat. No. 4,946,778). Single-chain Fvs and antibodies can be produced as described in U.S. Pat. Nos. 4,946,778 and 5,258,498; Huston et al., *Methods Enzynol.* 203:46 (1991); Shu et al., *Proc. Natl. Acad. Sci. USA* 90:7995 (1993); and Skerra et al., *Science* 240:1038 (1988).

Additional modifications of M2 antibodies included in the invention are antibody additions. For example, an addition can be the covalent or non-covalent attachment of any type of molecule to the antibody. Specific examples of antibody additions include glycosylation, acetylation, phosphorylation, amidation, formylation, ubiquitinatation, and derivatization by protecting/blocking groups and any of numerous chemical modifications.

Additions further include fusion (chimeric) polypeptide sequences, which is an amino acid sequence having one or more molecules not normally present in a reference native (wild type) sequence covalently attached to the sequence. A particular example is an amino acid sequence of another antibody to produce a multispecific antibody.

Another particular example of a modified M2 antibody having an amino acid addition is one in which a second heterologous sequence, i.e., heterologous functional domain is attached that confers a distinct or complementary function upon the antibody. For example, an amino acid tag such as T7 or polyhistidine can be attached to M2 antibody in order to facilitate purification or detection of M2 or influenza virus(es). Yet another example is an antiviral attached to an M2 antibody in order to target cells infected with influenza for virus killing, proliferation inhibition, replication inhibition, etc. Thus, in other embodiments the invention provides M2 antibodies and a heterologous domain, wherein the domain confers a distinct function, i.e. a heterologous functional domain, on the antibody.

Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral).

Linker sequences may be inserted between the antibody sequence and the heterologous functional domain so that the two entities maintain, at least in part, a distinct function or activity. Linker sequences may have one or more properties that include a flexible conformation, an inability to form an ordered secondary structure or a hydrophobic or charged character which could promote or interact with either domain. Amino acids typically found in flexible protein regions include Gly, Asn and Ser. Other near neutral amino acids, such as Thr and Ala, may also be used in the linker sequence. The length of the linker sequence may vary without significantly affecting a function or activity of the fusion protein (see, e.g., U.S. Pat. No. 6,087,329).

Additional examples of heterologous functional domains are detectable labels. Thus, in another embodiment, the invention provides human M2 antibodies that are detectably labeled.

Specific examples of detectable labels include fluorophores, chromophores, radioactive isotopes (e.g., $S^{35}$, $P^{32}$, $I^{125}$), electron-dense reagents, enzymes, ligands and receptors. Enzymes are typically detected by their activity. For example, horseradish peroxidase is usually detected by its ability to convert a substrate such as 3,3-',5,5-'-tetramethylbenzidine (TMB) to a blue pigment, which can be quantified. Ligands may bind other molecules such as biotin, which may bind avidin or streptavidin, and IgG, which can bind protein A.

It is understood that a M2 antibody may have two or more variations, modifications or labels. For example, a monoclonal antibody may be coupled to biotin to detect its presence with avidin as well as labeled with $I^{125}$ so that it provides a detectable signal. Other permutations and possibilities will be readily apparent to those of ordinary skill in the art, and are considered to be within the scope of the invention.

The invention further provides nucleic acids encoding M2 antibodies of the invention, including modified forms, fragments, chimeras, etc. In particular embodiments, a nucleic acid encodes intact or single chain M2 antibody denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA). In additional embodiments, a nucleic acid encodes intact or single chain as set forth in any of SEQ ID NO:26 and SEQ ID NO:27; SEQ ID NO:28 and SEQ ID NO:29; and SEQ ID NO:30 and SEQ ID NO:31.

The terms "nucleic acid" or "polynucleotide" are used interchangeably to refer to all forms of nucleic acid, including deoxyribonucleic acid (DNA) and ribonucleic acid (RNA). The nucleic acids can be double, single strand, or triplex, linear or circular. Nucleic acids include genomic DNA, cDNA, and antisense. RNA nucleic acid can be spliced or unspliced mRNA, rRNA, tRNA or antisense. Nucleic acids of the invention include naturally occurring, synthetic, as well as nucleotide analogues and derivatives. Such altered or modified polynucleotides include analogues that provide nuclease resistance, for example.

Nucleic acid can be of any length. For example, a nucleic acid can encode a heavy or light chain sequence of an antibody produced by a hybridoma or CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA) that encodes a protein having one or more anti-influenza activities. In a particular embodiment, a nucleic acid includes a heavy-chain variable sequence and light-chain variable sequence as set forth in any of SEQ ID NO:32 and SEQ ID NO:33; SEQ ID NO:34 and SEQ ID NO:35; and SEQ ID NO:36 and SEQ ID NO:37. In another particular embodiment, a nucleic acid encodes a heavy-chain variable sequence and light-chain variable sequence as set forth in any of SEQ ID NO:26 and SEQ ID NO:27; SEQ ID NO:28 and SEQ ID NO:29; and SEQ ID NO:30 and SEQ ID NO:31.

As a result of the degeneracy of the genetic code, nucleic acids include sequences that are degenerate with respect to sequences encoding no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA), L17 (ATCC Deposit No.; American Type Culture Collection, Manassas, Va., USA), and C40, L30, L40, S212, S80, S900 (ATCC Deposit Nos., respectively; American Type Culture Collection, Manassas, Va., USA) subsequences thereof and modified forms as set forth herein.

Nucleic acid can be produced using any of a variety of well known standard cloning and chemical synthesis methods and can be altered intentionally by site-directed mutagenesis or other recombinant techniques known to those skilled in the art. Purity of polynucleotides can be determined through sequencing, gel electrophoresis and the like.

Nucleic acids of the invention may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

The nucleic acids of the invention may be inserted into a plasmid for propagation into a host cell and for subsequent genetic manipulation if desired. A plasmid is a nucleic acid that can be stably propagated in a host cell, plasmids may optionally contain expression control elements in order to drive expression of the nucleic acid encoding M2 antibody in the host cell. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of M2 antibody encoding nucleic acids, producing M2 antibodies or antisense, and expressing the M2 antibodies in host cells or organisms, for example.

Nucleic acids encoding variable regions of the antibody heavy and light chains, or encoding full length antibody heavy and light chains can be isolated from a hybridoma. Isolated nucleic acids may be inserted into a suitable expression vector, and introduced into suitable host cells such as yeast or CHO cells which can be cultured for the production of recombinant M2 antibodies.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a M2 antibody in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology,* 153: 516 (1987), eds. Wu & Grossman; Bitter *Methods in Enzymology,* 152:673 (1987), eds. Berger & Kimmel, Acad. Press, N.Y.; and, Strathem et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 kb).

Host cells including nucleic acids encoding M2 antibodies are also provided. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded M2 antibody expressed. The term also includes any progeny or subclones of the host cell. Progeny cells and subclones need not be identical to the parental cell since there may be mutations that occur during replication and proliferation. Nevertheless, such cells are considered to be host cells of the invention.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression, are provided.

Expression vectors also can contain a selectable marker conferring resistance to a selective pressure or identifiable marker (e.g., β-galactosidase), thereby allowing cells having the vector to be selected for, grown and expanded. Alternatively, a selectable marker can be on a second vector that is cotransfected into a host cell with a first vector containing an invention polynucleotide.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk−, hgprt$^-$ or aprt$^-$ cells respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomnycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology*, Cold Spring Harbor Laboratory).

Methods for treating influenza virus infection of a subject include administering to the subject an amount of a human, humanized or chimeric antibody that specifically binds influenza M2 protein effective to treat influenza virus infection of the subject. The antibody can be administered prior to infection, i.e., prophylaxis, substantially contemporaneously with infection, or following infection of the subject, i.e., therapeutic treatment.

Methods of the invention include providing a therapeutic benefit to a subject, for example, reducing or decreasing one or more symptoms or complications associated with influenza virus infection, reducing or inhibiting increases in virus titer, virus replication, virus proliferation, or an amount of a viral protein of one or more influenza virus strains or isolates. Symptoms or complications associated with influenza virus infection that can be reduced or decreased include, for example, chills, fever, cough, sore throat, nasal congestion, sinus congestion, nasal infection, sinus infection, body ache, head ache, fatigue, pneumonia, bronchitis, ear infection or ear ache. A therapeutic benefit can also include reducing susceptibility of a subject to influenza virus infection or hastening a subject's recovery from influenza virus infection.

In one embodiment, a method includes administering to the subject an amount of a human, humanized or chimeric antibody that specifically binds influenza virus M2 effective to inhibit virus infection of the subject or reduce susceptibility of the subject to virus infection by one or more influenza virus strains or isolates. In various aspects, the antibody is administered prior to (prophylaxis), substantially contemporaneously with or following infection of the subject (therapeutic). The antibody can provide a therapeutic benefit which includes, for example, reducing or decreasing the severity or duration of one or more symptoms or complications of influenza virus infection (e.g., chills, fever, cough, sore throat, nasal congestion, sinus congestion, nasal infection, sinus infection, body ache, head ache, fatigue, pneumonia, bronchitis, ear infection or ear ache), virus titer or an amount of a viral protein of one or more influenza virus strains or isolates, or susceptibility of a subject to infection by one or more influenza virus strains or isolates.

Therapeutic benefits and therefore methods for preventing or inhibiting an increase in influenza virus titer, virus replication, virus proliferation or an amount of an influenza viral protein in a subject are further provided. In one embodiment, a method includes administering to the subject an amount of a human, humanized or chimeric antibody that specifically binds influenza M2 effective to prevent an increase in influenza virus titer, virus replication or an amount of an influenza viral protein of one or more influenza strains or isolates in the subject.

Methods for protecting a subject from infection, decreasing susceptibility of a subject to infection and hastening a subject's recovery from infection by one or more influenza strains or isolates are additionally provided. In one embodiment, a method includes administering to the subject an amount of a human, humanized or chimeric antibody that specifically binds influenza M2 effective to protect the subject from virus infection, effective to decrease susceptibility of the subject to virus infection or hastening a subject's recovery from virus infection, by one or more influenza virus strains or isolates.

Methods of the invention, including therapeutic and diagnostic methods, and purification/isolation methods, can be practiced with any antibody set forth herein. In particular non-limiting embodiments, a method includes an antibody that specifically binds to a sequence (or two or more sequences) that includes or consists of SLLTEVETPIRNEWGCRCNDSSD (M2, SEQ ID NO:1), a subsequence thereof or an amino acid variant thereof (e.g., an amino acid substitution, insertion, deletion or addition), such as

```
SLLTEVETPIRNEWECRCNGSSD; (M2EG, SEQ ID NO: 2)

SLLTEVETPIRNEWGCKCNDSSD; (M2K, SEQ ID NO: 3)

SLLTEVETPIRNEWGCRCNGSSD; (M2G, SEQ ID NO: 4)

SFLTEVETPIRNEWGCRCNGSSD; (M2FG, SEQ ID NO: 5)

SLLTEVDTLTRNGWGCRCSDSSD; (M2DLTGS, SEQ ID NO: 6)

SLLTEVETLTKNGWGCRCSDSSD; (M2LTKGS, SEQ ID NO: 7)

SLLTEVETLTRNGWGCRCSDSSD; (M2LTGS; SEQ ID NO: 8)

SLLTEVETLTRNGWECKCSDSSD; (M2LTGEKS, SEQ ID NO: 9)

SLLTEVETPTRNGWECKCSDSSD; (M2TGEKS; SEQ ID NO: 10)

SLLTEVETPTRNEWECRCSDSSD; (M2TES, SEQ ID NO: 11)
```

-continued

```
SLLTEVETPTRNGWGCRCSDSSD; (M2TGS, SEQ ID NO: 12)

SLLTEVETPTRNGWECKCNDSSD; (M2TGEK, SEQ ID NO: 13)

SLLTEVKTPTRNGWECKCSDSSD; (M2KTGEKS, SEQ ID NO: 14)

SLLTEVETPTRDGWECKCSDSSD; (M2TDGEKS, SEQ ID NO: 15)

SLLTEVETHTRNGWECKCSDSSD; (M2HTGEKS, SEQ ID NO: 16)

SLPTEVETPIRNEWGCRCNDSSD; (M2P, SEQ ID NO: 17)

SLLTEVETPIRSEWGCRCNDSGD; (M2SG, SEQ ID NO: 18)

SLLTEVETPTRNGWECRCNDSSD; (M2TGE, SEQ ID NO: 19)

SLLTEVETPIRKGWECNCSDSSD; (M2KGENS, SEQ ID NO: 20)

SLLTGVETHTRNGWGCKCSDSSD; (M2GHTGKS, SEQ ID NO: 21)
and

SLLPEVETHTRNGWGCRCSDSSD. (M2PHTGS; SEQ ID NO: 22)
```

In additional particular non-limiting embodiments, a method includes an antibody having the same or substantially the same binding specificity or binding affinity of an antibody produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA); antibodies produced by a cell line (e.g., a hybridoma or a CHO cell line) denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA). In further particular non-limiting embodiments, a method includes an antibody that specifically binds to one or more of M2TGEKS (SEQ ID NO:10), M2TDGEKS (SEQ ID NO:15), M2LTGEKS (SEQ ID NO:9) or M2TGE (SEQ ID NO:19), as determined under certain assay conditions; an antibody that specifically binds to a minimal binding sequence, such as a sequence that is the same or substantially the same as LLTEVETPIRNEWGC (SEQ ID NO:25); SLLTEVETPIRNEWGC (SEQ ID NO:23); or TPIRNE (SEQ ID NO:24), or the same or substantially the same as the minimal binding sequence to which antibody produced by the hybridoma or a CHO cell line denoted as no. 2074 (ATCC Deposit No. PTA-4025; American Type Culture Collection, Manassas, Va., USA), 161 (ATCC Deposit No. PTA-4026; American Type Culture Collection, Manassas, Va., USA), N547 (ATCC Deposit No. PTA-5049; American Type Culture Collection, Manassas, Va., USA,), L66 (ATCC Deposit No. PTA-5048; American Type Culture Collection, Manassas, Va., USA), C40G1 (ATCC Deposit No. PTA-5050; American Type Culture Collection, Manassas, Va., USA) or L17 (ATCC Deposit No.; American Type Culture Collection, Manassas, Va., USA) binds. In additional particular non-limiting embodiments, a method includes an antibody that does not specially bind to a sequence LTEVETPIRNEW (SEQ ID NO:71) or a sequence EVETPIRN (SEQ ID NO:72).

Methods of the invention, including therapeutic, diagnostic and purification/isolation methods are applicable to any influenza strain/isolate or combination of strains/isolates. Particular non-limiting examples of influenza strains are A/PR/8/34 or A/HK/8/68, or other strains selected from H1N1, H2N2, H3N2, H5N1, H9N2, H2N1, H4N6, H6N2, H7N2, H7N3, H4N8, H5N2, H2N3, H11N9, H3N8, H1N2, H11N2, H11N9, H7N7, H2N3, H6N1, H13N6, H7N1, H11N1, H7N2 and H5N3.

Human, humanized and chimeric M2 antibodies of the invention may be used alone or in combination with therapeutic agents having anti-influenza activity, e.g., that inhibit influenza virus infection, replication, proliferation, or reduce the severity or duration of one or more symptoms or complications associated with influenza virus infection. Examples of such combinations include pooled monoclonal antibodies containing two or more different M2 antibodies with different binding specificity, binding affinity, or efficacy in inhibiting influenza virus infection of a cell in vitro or in vivo. Accordingly, combination compositions including M2 antibodies are provided, as well as methods of using such combinations in accordance with the methods of the invention.

The methods of the invention, including treating influenza or a disorder or complication associated with influenza virus infection, likely results in an improvement in the subjects' condition, a reduction of the severity or duration of one or more symptoms or complications associated with influenza virus infection, or decreasing the subject's risk for developing symptoms or contracting the infection, e.g., susceptibility to influenza virus infection. An improvement therefore includes one or more decreased or reduced virus proliferation, replication, or titre, or symptoms or complications associated with influenza virus infection. An improvement also includes reducing the dosage frequency or amount of an antiviral drug or other agent used for treating a subject having or at risk of having an influenza virus infection, or a symptom or complication associated with influenza virus infection.

An improvement need not be complete ablation of any or all symptoms or complications associated with influenza virus infection. Rather, treatment may be any measurable or detectable anti-influenza virus effect or improvement as set forth herein. Thus, a satisfactory clinical endpoint is achieved when there is an incremental improvement or a partial reduction in the subjects condition or associated symptoms or complications, or an inhibition of worsening of the condition, over a short or long duration.

Subjects appropriate for treatment include those having or at risk of having influenza virus infection. Target subjects also include those at risk of developing an influenza associated symptom or complication. The invention methods are therefore applicable to treating a subject who is at risk of influenza virus infection or a complication associated with influenza virus infection. Prophylactic methods are therefore included.

At risk subjects appropriate for treatment include subjects exposed to other subjects having influenza virus, or where the risk of influenza virus infection is increased due to changes in virus infectivity or cell tropism, immunological susceptibility (e.g., an immunocompromised subject), or environmental factors.

M2 antibodies can be administered as a single or multiple dose e.g., one time per week for between about 1 to 10 weeks, or for as long as appropriate, for example, to achieve a reduction in the severity of one or more symptoms or complications associated with influenza virus infection. Doses can vary depending upon whether the treatment is prophylactic or therapeutic, the severity of the associated disorder or complication being treated, the clinical endpoint desired, previous or simultaneous treatments, the general health, age, sex or race of the subject and other factors that will be appreciated by the skilled artisan. The skilled artisan will appreciate the factors that may influence the dosage and timing required to provide an amount sufficient for therapeutic benefit. Doses can be empirically determined or determined using animal disease models or optionally in human clinical trials.

The term "subject" refers to animals, typically mammalian animals, such as a non human primate (apes, gibbons, chimpanzees, orangutans, macaques), a domestic animal (dogs and cats), a farm animal (horses, cows, goats, sheep, pigs), experimental animal (mouse, rat, rabbit, guinea pig) and humans. Subjects include animal disease models, for example, the mouse model of influenza infection exemplified herein.

M2 antibodies of the invention, including modified forms, variants and subsequences thereof, and nucleic acids encoding M2 antibodies, can be incorporated into pharmaceutical compositions. Such pharmaceutical compositions are useful for administration to a subject in vivo or ex vivo.

Antibodies can be included in a pharmaceutically acceptable carrier or excipient prior to administration to a subject. As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. Such formulations can be contained in a tablet (coated or uncoated), capsule (hard or soft), microbead, emulsion, powder, granule, crystal, suspension, syrup or elixir. Supplementary active compounds (e.g., preservatives, antibacterial, antiviral and antifungal agents) can also be incorporated into the compositions.

Pharmaceutical compositions can be formulated to be compatible with a particular route of administration. Thus, pharmaceutical compositions include carriers, diluents, or excipients suitable for administration by various routes.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. For transdermal administration, the active compounds are formulated into aerosols, sprays, ointments, salves, gels, or creams as generally known in the art.

Pharmaceutical formulations and delivery systems appropriate for the compositions and methods of the invention are known in the art (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky et al., *Drug Delivery Systems*, R. L. Juliano, ed., Oxford, N.Y. (1980), pp. 253-315)

The pharmaceutical formulations can be packaged in unit dosage form for ease of administration and uniformity of dosage. Unit dosage form as used herein refers to physically discrete units suited as unitary dosages for the subject to be treated; each unit containing a predetermined quantity of active compound calculated to produce a desired therapeutic effect in association with the pharmaceutical carrier or excipient.

The invention provides kits comprising M2 antibodies, nucleic acids encoding M2 antibodies and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more human M2 antibodies alone or in combination with an antiviral agent or drug.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions.

Kits of the invention therefore can additionally include labels or instructions for using the kit components in a method of the invention. Instructions can include instructions for practicing any of the methods of the invention described herein including treatment, detection, monitoring or diagnostic methods. Thus, for example, a kit can include a human M2 antibody that has one or more anti-influenza activities as set forth herein, together with instructions for administering the antibody in a treatment method of the invention.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Invention kits can additionally include a growth medium (e.g., for an M2 antibody producing cell line), buffering agent, or a preservative or a stabilizing agent in a pharmaceutical formulation containing an M2 antibody. Each component of the kit can be enclosed within an individual container and all of the various containers can be within a single package. Invention kits can be designed for cold storage. Invention kits can further be designed to contain human M2 antibody producing hybridoma or other host cells (e.g., CHO cells). The cells in the kit can be maintained under appropriate storage conditions until the cells are ready to be used. For example, a kit including one or more hybridoma or other cells can contain appropriate cell storage medium (e.g., 10-20% DMSO in tissue culture growth medium such as DMEM, α-MEM, etc.) so that the cells can be thawed and grown.

M2 antibodies of the invention are useful for isolating, detecting or purifying M2 polypeptides. Such methods include contacting a sample suspected of containing M2 (in solution, in solid phase, in vitro or in vivo, or in an intact cell or organism) with an M2 antibody under conditions allowing binding, and detecting the presence of M2, or purifying the bound M2 protein.

The invention therefore also provides methods for detecting M2 or influenza virus in a test sample. In one embodiment, a method includes contacting a sample having or suspected of having M2 or influenza virus with a human M2 antibody under conditions allowing detection of M2 in the sample and determining whether M2 is present in the test sample. Detection of M2 or influenza virus can be performed by conventional methods such as immunoprecipitation, western blotting, immunohistochemical staining or flow cytometry and ELISA.

M2 and influenza virus detection methods are useful in diagnostic protocols for detecting M2 and influenza virus. For example, where increased or decreased levels of influenza virus are associated with development or regression of influenza infection, invention antibodies can be used to detect any increase or decrease in M2 or influenza virus. In addition, where it is desired to monitor levels of M2 or influenza virus following a treatment therapy that decreases M2 or influenza virus levels, invention antibodies can be used to detect such an increase or decrease in M2 or influenza virus levels before, during or following the treatment, over a long or short period of time.

The invention therefore also provides methods for detecting the presence of M2 or influenza virus in a test sample of a subject (containing biological fluid, cells, or a tissue or organ sample such as a biopsy). In one embodiment, a method includes contacting a sample having or suspected of having M2 or influenza virus obtained from a subject with a human M2 or influenza virus antibody under conditions allowing detection of M2 or influenza virus and determining whether M2 or influenza virus is present in the test sample from the subject.

M2 antibodies may also be utilized to monitor the presence of M2 or influenza virus for diagnosis or following treatment of a subject, or to measure in vivo levels of M2 in subjects. For example, sputum suspected of containing M2 or influenza virus is incubated with an M2 antibody, as described above, under conditions allowing binding to occur, which detects the presence of M2 or influenza virus Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "an M2 antibody" includes a plurality of such antibodies and reference to "an anti influenza activity or function" can include reference to one or more activities or functions, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes any numerical value or range within or encompassing such values, such as 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and any numerical range within such a range, such as 90-92%, 90-95%, 95-98%, 96-98%, 99-100%, etc. In an additional example, reference to a range, for example, 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a range, such as 1-2, 5-10, 10-50, 50-100, 100-500, 100-1000, 500-1000, 1000-2000, 1000-5000, etc. In a further example, reference to a range of KD $10^{-5}$ M to about KD $10^{-13}$ M includes any numerical value or range within or encompassing such values.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Peptide synthesis and peptide-KLH conjugates: M2 peptides were synthesized by Multiple Peptide Systems (San Diego, Calif.). Peptide purity was >95% after HPLC. The M2 peptide was then conjugated to KLH (M2-KLH) and BSA (M2-BSA) by the same company. The sequence of the extra-cellular 23-amino-acid M2 peptide is: SLLTEVET-PIRNEWGCRCNDSSD (SEQ ID NO:1).

Mice: Human trans-chromosomic mice (WO 02/43478, WO 02/092812, Ishida and Lonberg, IBC's $11^{th}$ Antibody Engineering Meeting. Abstract (2000); and Kataoka, S. IBC's $13^{th}$ Antibody Engineering Meeting. Abstract (2002)) harboring human chromosome fragments containing the human immunoglobulin region were obtained from Kirin Brewery Co., Ltd. (Japan). C57BL/6J mice were purchased from Jackson Laboratories at Bar Harbor, Me. and were housed in the animal facility at the La Jolla Institute for Allergy and Immunology.

Immunization: M2-KLH or M2-BSA in PBS (GIBCO BRL, Rockville, Md.) was mixed with an equal volume of complete Freund's adjuvant (CFA) (Sigma, St. Louis, Mo.) and an emulsion was prepared. Mice were immunized with 20 μg of M2-KLH or M2-BSA in CFA subcutaneously and were boosted either subcutaneously with 20 μg of M2-KLH or M2-BSA in incomplete Freund's adjuvant (WFA) (Sigma, St. Louis, Mo.) or intraperitoneal injection with RIBI (Corixa, Hamilton Mont.) after 21 days and repeated once more following another 21 days. A final intraperitoneal and intravenous injection of 10 μg of M2 peptide without adjuvant was given 3 days before fusion.

ELISA: Antibody titers and antibody specificity as well as antibody production by hybridomas were determined by ELISA. In brief, 50 μl of M2-BSA or M2 peptide were coated on a 96-well flat bottom plate (Nunc, Denmark) at a concentration of 1 μg/ml with carbonate buffer (pH 9.6) overnight at 4° C. or at 37° C. for 1 hr. After washing twice with PBS/0.1% Tween 20, plates were blocked with PBS/1% BSA (Sigma, St. Louis, Mo.) at 37° C. for 30 min., the antibody or serum was added to the wells and the plates were incubated at 37° C. for 1 hr. After washing four times, diluted HRP conjugated goat anti-human Immunoglobulin gamma chain specific antibody (Jackson Immunoresearch Laboratory, West Grove, Pa.) was added to the wells and incubated for 1 hr at 37° C. After washing four times, TMB substrate solution (DAKO, CA) was added and incubated for 30 min at room temperature. The optical density at 450 nm was measured by a microplate reader.

Isotype ELISA: The isotype of the antibody produced by the hybridomas was determined by ELISA. In brief, 50 μl of M2-BSA or M2 peptide were coated on a 96-well flat bottom plate (Nunc, Denmark) at a concentration of 1 μg/ml with carbonate buffer (pH 9.6) overnight at 4° C. or at 37° C. for 1 hr. After washing twice with PBS/0.1% Tween 20, plates were blocked with PBS/1% BSA (Sigma, St. Louis, Mo.) at room temperature for 1 hr, the antibody was added to the wells and the plates were incubated at room temperature for 1 hr. After washing three times, either of diluted HRP-conjugated mouse anti-human IgG1, IgG2, IgG3 and IgG4 heavy chain detection antibodies (Zymed, San Francisco, Calif.) was added to the wells and incubated for 1 hr at room temperature. After washing three times, TMB substrate solution (DAKO, CA) was added and incubated for 30 min at room temperature. The optical density at 450 nm was measured by a microplate reader.

Influenza A virus-infected cell-based ELISA: MDCK cells (Madin-Darby Canine Kidney epithelial cells; ATCC, Rockville, Md.) were plated in a 96-well flat bottom plate (Falcon®) at $1.5 \times 10^5$ cells per mL and 150 μl per well and cultured for 48 hr at 7% $CO_2$. After 48 hr the plate was washed twice with PBS and infected at room temperature for 30 minutes with 30 μl of 100-fold $TCID_{50}$ influenza A virus (A/PR/8/34 or A/HK/8/68; ATCC, Rockville, Md.) with periodically swirling. After infection, the plate was washed once with PBS and 150 μl of 1 μg/mL trypsin (TPCK-treated, Worthington, Biochem. Corp.) in Minimal Essential Media (Invitrogen Corp, CA) was added and the plate incubated for 27 hr. After infection, the cell monolayer was washed with PBS/1% FCS (GIBCO BRL, Rockville, Md.) three times and blocked with PBS/1% BSA/5% FCS at room temperature for 30 min. The antibodies were diluted and 50 μl added to each well and incubated at room temperature for 45 min. After washing 4 times, the HRP conjugated Rabbit anti-human immunoglobulin gamma chain antibody (DAKO, Denmark) was diluted 1:3000 and 50 μl added to each well and the plate was incubated at room temperature for 30 min. After washing 5 times, 100 μl of TMB substrate (DAKO, Denmark) containing 1 mM Levamisole solution (Vector Laboratories Inc. Burlingame, Calif.) was added and the plates were incubated at room temperature for 15 min. 50 μl of supernatant were transferred to a new 96-well plate (Nunc, Denmark) containing 100 μl stop solution (1N $H_2SO_4$) and the optical density (OD) at 450 nm was measured by a microplate reader. $EC_{50}$ of each antibody was calculated as previously described (Sette et al. *Nature* 328:395 (1987)). The OD data of no. 2074 antibody at 10 μg/ml was set as 100% as an internal control.

Peptide competition in Influenza A virus-infected cell-based ELISA: Virus-infected MDCK cells were prepared as described above. The M2 peptide and the anti M2 antibodies were mixed and incubated at room temperature for 30 min. After incubation, 50 μl (10 μg/ml) of the mixture of peptide and antibodies were added to blocked cells and incubated at room temperature for 30 minutes After washing 4 times, the HRP conjugated Rabbit anti-human immunoglobulin gamma chain antibody (DAKO, Denmark) was diluted 1:3000 and 50 μl added to each well and the plate was incubated at room temperature for 30 min. After washing for 5 times, 100 μl of TMB substrate (DAKO, Denmark) containing 1 mM Levamisole solution (Vector Laboratories Inc. Burlingame, Calif.) was added and the plates were incubated at room temperature for 15 min. Fifty μl of supernatant was transferred to a new 96-well plate (Nunc, Denmark) containing 100 μl stop solution (1N $H_2SO_4$) and the optical density at 450 nm was measured by a microplate reader.

Hybridoma production. The mouse having the highest antibody titer was selected for production of monoclonal antibodies. The spleen was harvested and single cell suspension was fused to a myeloma cell line (SP2/O-Ag14) (ATCC, Rockville, Md.) at a 3:1 ratio with 50% PEG (Boehringer Mannheim, Indianapolis, Ind.). The fusions were plated onto 96-well plate at an optimal density and cultured in complete RPMI-10 medium (RPMI 1640 with 10% FCS, 1% nonessential amino acids, 2 mM L-glutamine, 50 μM 2-ME, 100 U/ml penicillin and 100 μg/ml streptomycin sulfate) in a 5% $CO_2$, 37° C. incubator. Approximately 2000 hybridoma growing wells of each fusion were screened by ELISA. Cells positive for binding to the M2 peptide were transferred to 24 well plates and 4 rounds of limiting dilutions were performed to obtain monoclonal antibodies. Anti-M2 monoclonal antibodies were further confirmed by an Influenza A virus infected cell based ELISA.

Antibody purification: For antibody purification, hybridomas were cultured in an Integra system (INTEGRA Bioscience, Inc. Ijamsville, Md.) with hybridoma-SFM (GIBCO BRL, Rockville, Md.). Human monoclonal antibodies were purified from culture media using Protein A-Sepharose Fast Flow gel (Amersham Pharmacia Cat#17-0618-02, Uppsala, Sweden). Briefly, conditioned medium, containing an appropriate amount of the antibody for the column capacity, was filtered with a 0.22 μm disk filter (Minisarto-plus, Sartorius Cat#17822, Gettingen, Germany) and loaded onto a 2.0 ml Protein A-Sepharose Fast Flow column equilibrated with phosphate buffered saline (PBS). The column was washed with more than 40 ml of PBS and the antibody was eluted with 0.1 M Gly-HCl, pH3.6, 0.15 M NaCl. After the initial 1.0 ml of the elution buffer had passed through, 3 separate elution fractions were collected at a volume of 5.0 ml/tube, and neutralized immediately with 250 μl of 1 M Tris-HCl, pH8.0. This purification procedure was repeated until all conditioned media were processed. Antibody concentration was determined with a human IgG-specific ELISA and all fractions containing the antibody were pooled and concentrated with a centrifugal concentrator (Vivaspin 20, 30,000MWCO: Sartorius Cat#VS2022, Gettingen, Germany).

In order to remove pyrogen, the concentrated sample was buffer-exchanged into 20 mM sodium phosphate, pH6.6, and loaded onto a 0.5 ml SP-Sepharose HP column (Amersham Pharmacia, Cat#17-1087-01, Uppsala, Sweden) equilibrated with the same buffer. The pyrogen was removed by first passing the sample through a 2 ml Q-Sepharose Fast Flow column (Amersham Pharmacia, Cat#17-0510-01, Uppsala, Sweden) that was connected in series to a SP-Sepharose HP column. After application, the Q-Sepharose Fast Flow column was removed and the antibody was eluted with a linear gradient ranging from 0 to 0.5 M sodium chloride. The antibody was detected at 280 nm and the antibody containing fractions pooled. The sample was concentrated with a centrifugal concentrator and buffer-exchanged into PBS by using NAP25 desalting columns (Amersham Pharmacia, Cat#17-0852-02, Uppsala, Sweden). Antibody concentration was quantitated by a human IgG specific ELISA. Pyrogen levels of samples were determined to be less than 0.13 EU/mg of protein according to a *Limulus Amebocyte* Lysate (LAL) assay (Associates of Cape Cod, Inc., Falmouth, Mass.).

Isolation of Human Anti-M2 Antibody (C40) Genes:

Cultured hybridoma cells (113C-40-H-22), which produce C40 antibody (isotype: IgG4) were collected by centrifugation. 240 microgram of total RNA was purified from these cells using ISOGEN (NIPPONGENE, Co., Ltd.), and subsequently 3 microgram of polyA$^+$ RNA was purified from 120 microgram of total RNA using Oligotex™-dT30<Super> (Takara Shuzo, CO., Ltd., Japan). SMART RACE cDNA Amplification Kit (Clontech, Co., Ltd., CA) was used for cloning of cDNA of variable region of immunoglobulin genes from polyA$^+$ RNA of hybridoma cells as a source. Briefly, first strand cDNA was prepared by reverse transcriptase from 2 microgram of polyA$^+$ RNA. This cDNA was used as a template for polymerase chain reaction (PCR) to amplify variable regions of both heavy chain and light chain which included leader sequences (HV and LV, respectively). The reaction was as follows: 2.5 U TaKaRa LA Taq™ DNA polymerase (Takara Shuzo, Co.); 0.2 μM Primer for one side (for Heavy chain: IgG1p, for Light chain: hk-2, see Table 1); 0.2 μM Primer for the other side (UMP primer attached to SMART RACE Kit); 400 μM each dNTP mix; LA PCR Buffer II (Mg2+ plus) (final concentration is 1×); and cDNA template.

The thermocycling program was 94° C. for 5 min, and then 30 cycles at 94° C. for 10 sec and 68° C. for 1 min with an extension at 72° C. for 7 min. Amplified DNA fragments were collected after ethanol precipitation and subsequent agarose gel electrophoresis, and purified by QIAquick Gel Extraction Kit (Qiagen Co., Ltd., Germany). Nucleotide sequences of both PCR-amplified products (HV and LV) were confirmed with specific primers (HV: hh-4, LV: hk-5 and hk-6, see Table 1 for sequences of primers). Purified DNA fragments of HV and LV was integrated into pGEM®-T Easy Vector System (Promega Co.), and each construct plasmid was electroporated in *E. coli*, and then cloned. Nucleotide sequences of each insert (HV and LV) in construct plasmids were analysed using specific primers (SP6 and T7, see Table 1). Nucleotide sequences of both HV and LV from construct plasmids were completely coincided with those from PCR products. Nucleotide sequences of HV and LV and these amino acid sequences are shown below.

```
Nucleotide sequence of cDNA of C40 heavy chain variable region
(HV) (from initiation codon (ATG) to the end of variable region)-
                                                   (SEQ ID NO: 32)
ATGAAGCACC TGTGGTTCTT CCTCCTGCTG GTGGCGGCTC CCAGATGGGT CCTGTCCCAG   60

CTGCAGCTGC AGGAGTCGGG CCCAGGACTG GTGAAGCCTT CGGAGACCCT GTCCCTCACC  120

TGCACTGTCT CTGGTGGTTC CATCAGCAGT AGTTTTTACT ACTGTGGCTG GATCCGCCAG  180

CCCCCAGGGA AGGGGCTGGA GTGGATTGGG AGTATCTATT ATCGTGGGAG CACCTACTAC  240

AACCCGTCCC TCAAGAGTCG AGTCACCATA TCCGTAGACA CGTCCAAGAA CCAGTTCTCC  300

CTGAAGCTGA GCTCTGTGAC CGCCGCAGAC ACGGCTGTGT ATTACTGTGC GAGACGGGTT  360

ACTATGGTTC GGGGAGTTAA GGGGGACTAC TTTGACTACT GGGGCCAGGG AACCCTGGTC  420

ACCGTCTCCT CA                                                       432
```

-continued

Nucleotide sequence of cDNA of C40 light chain variable region (LV) (from initiation codon (ATG) to the end of variable region)-

(SEQ ID NO: 33)

```
ATGAGGGTCC TCGCTCAGCT CCTGGGGCTC CTGCTGCTCT GTTTCCCAGG TGCCAGATGT   60

GACATCCAGA TGACCCAGTC TCCATCCTCA CTGTCTGCAT CTGTAGGAGA CAGAGTCACC  120

ATCACTTGTC GGGCGAGTCA GGGTATTAGC AGCTGGTTAG CCTGGTATCA GCAGAAACCA  180

GAGAAAGTCC CTAAGTCCCT GATCTATGCT GCATCCAGTT TGCAAAGTGG GGTCCCATCA  240

AGGTTCAGCG GCAGTGGATC TGGGACAGAT TTCACTCTCA CCATCAGCAG CCTGCAGCCT  300

GAAGATTTTG CAACTTATTA CTGCCAACAG TATAATTATT ACCCGCTCAC TTTCGGCGGA  360

GGGACCAAGG TGGAGATCAA ACGA                                         384
```

Amino acid sequence of cDNA of C40 heavy chain variable region (HV) (leader sequence (underlined) and variable region)-

(SEQ ID NO: 26)

```
MKHLWFFLLL VAAPRWVLSQ LQLQESGPGL VKPSETLSLT CTVSGGSISS SFYYCGWIRQ   60

PPGKGLEWIG SIYYRGSTYY NPSLKSRVTI SVDTSKNQFS LKLSSVTAAD TAVYYCARRV  120

TMVRGVKGDY FDYWGQGTLV TVSS                                         144
```

Amino acid sequence of cDNA of C40 light chain variable region (LV) (leader sequence (underlined) and variable region)

(SEQ ID NO: 27)

```
MRVLAQLLGL LLLCFPGARC DIQMTQSPSS LSASVGDRVT ITCRASQGIS SWLAWYQQKP   60

EKVPKSLIYA ASSLQSGVPS RFSGSGSGTD FTLTISSLQP EDFATYYCQQ YNYYPLTFGG  120

GTKVEIKR                                                           128
```

Generation of Expression Vector of Isotype-Changed Human Anti-M2 Antibody (C40-IgG1 Type):

For making IgG1 type isotype-switched C40 antibody (the original isotype was IgG4), a new DNA vector was constructed. Briefly, the primer set for PCR of LV was designed to have sensitive region to restriction enzymes in the both sides of LV. The primer set used is M240L5BGL and M240L3BSI (Table 1), and construct plasmid of LV was used as a template. Purified PCR-amplified product of LV was subcloned into pGEM®-T Easy Vector System (Promega, Co., Ltd.). Nucleotide sequence of the insert was confirmed. The plasmid DNA was digested by two restriction enzymes, BglII and BsiWI, and 0.4 kilobases DNA insert (fragment A, see FIG. 1) was isolated and purified by the agarose gel electrophoresis.

Plasmid vector (IDEC Pharmaceuticals, CA, N5KG1-Val Lark (a modified vector of N5KG1 in U.S. Pat. No. 6,001,358)) was used as an expression vector for IgG1 production, which contains constant regions of both IgG1 light and heavy chains. The vector DNA was digested by the two enzymes, BglII and BsiWI, and subsequently treated with alkaline phosphatase (Takara Shuzo, Co., Ltd., Japan) for dephosphorylation of the end of the DNA. 8.9 kilobases DNA fragment (fragment B) was isolated by agarose gel electrophoresis and DNA purification kit.

Two DNA fragments, A and B were ligated with T4 DNA ligase (Takara Shuzo, Co., Ltd., Japan), and ligated construct (N5KG1_C40Lv) was electroporated into *E. coli* DH5α strain to generate transformants. Positive *E. coli* transformants were selected.

As the second step, HV was inserted into N5KG1_C40Lv DNA vector as follows: the DNA vector was digested by two DNA restriction enzymes, NheI and SalI, and subsequently dephosphorylated. 9.2 kilobases DNA fragment (fragment C) was isolated. Similarly to light chain construct, the primer set for PCR of HV was designed to have the sensitive region to restriction enzymes in the both sides of HV. The primer set used is M240H5SAL and M240H3NHE (Table 1), and construct plasmid of HV was used as a template. Purified PCR-amplified product of HV was subcloned into pGEM®-T Easy Vector System. Nucleotide sequence of the insert in the subcloned constrict was confirmed. The plasmid DNA was digested by two restriction enzymes, NheI and SalI, and 0.44 kilobases DNA insert (fragment D, see FIG. 1) was isolated and purified after agarose gel electrophoresis.

Two DNA fragments, C and D were ligated with T4 DNA ligase, and ligated construct (N5KG1_M2C40) was electroporated into *E. coli* DH5α strain to generate transformant. Positive *E. coli* transformants were selected. This expression vector was purified, and nucleotide sequence of both LV and HV regions were confirmed. No mutations were introduced during the process.

TABLE 1

Synthesized DNA primers (SEQ ID NOS:38 - 55)

| No | Name | Sequence 5' to 3' | Length |
|---|---|---|---|
| 38 | IgG1 | TCTTGTCCACCTTGGTGTTGCTGGGCTTGTG | 31-mer |
| 39 | hk-2 | GTTGAAGCTCTTGTGACGGGCGAGC | 26-mer |
| 40 | hh-4 | GGTGCCAGGGGGAAGACCGATGG | 23-mer |
| 41 | hk-5 | AGGCACACAACAGAGGCAGTTCCAGATTTC | 30-mer |
| 42 | hh-6 | GGTCCGGGAGATCATGAGGGTGTCCTT | 27-mer |
| 43 | SP6 | GATTTAGGTGACACTATAG | 19-mer |
| 44 | T7 | TAATACGACTCACTATAGGG | 20-mer |
| 45 | M240L5BGL | AGAGAGAGAGATCTCTCACCATGAGGGTCCT CGCTCAGCTCCTG | 44-mer |
| 46 | M240L3BSI | CTCTCTCTCGTACGTTTGATCTCCACCTTGG TCC | 34-mer |

TABLE 1-continued

Synthesized DNA primers (SEQ ID NOS:38 - 55)

| No | Name | Sequence 5' to 3' | Length |
|---|---|---|---|
| 47 | M240H5SAL | AGAGAGAGGTCGACACCATGAAGCACCTGTG GTTCTTCCT | 40-mer |
| 48 | M240H3NHE | CTCTCTCTGCTAGCTGAGGAGACGGTGACCA GG | 33-mer |
| 49 | SEQU1783 | GGTACGTGAACCGTCAGATCGCCTGGA | 27-mer |
| 50 | SEQU4618 | TCTATATAAGCAGAGCTGGGTACGTCC | 27-mer |
| 51 | hh-1 | CCAAGGGCCCATCGGTCTTCCCCCTGGCAC | 30-mer |
| 52 | CMVH903F | GACACCCTCATGATCTCCCGGACC | 24-mer |
| 53 | CMVHF1283 | CGACATCGCCGTGGAGTGGGAGAG | 24-mer |
| 54 | CMVHR1303 | TGTTCTCCGGCTGCCCATTGCTCT | 24-mer |
| 55 | hk-1 | TGGCTGCACCATCTGTCTTCATCTTC | 26-mer |

Generation of Expression Vector of Isotype-Changed Human Anti-M2 Antibody (IgG4-Type C40):

For generation of DNA construct of IgG4 type C40, N5KG4PE DNA vector was used instead of N5KG1-Val Lark vector. This DNA vector contains constant regions of both light chain and heavy chains of IgG4. Procedure of generation of IgG4 vector of C40 was the same as that of IgG1-type C40.

Production of Recombinant Human Anti-M2 Antibody from CHO Cells:

For the production of recombinant antibody, generated DNA vector was transfected into host cells, and recombinant antibody was isolated from the supernatant of the transfected cells. Briefly, DNA vector was transfected into host cell dhfr-defective strain of Chinese Hamster Ovary cell (CHO cells, ATCC #CRL-9096) by electroporation. Twenty microgram of purified DNA expression vector, N5KG1_M2C40, was linearized by a DNA restriction enzyme, AscI, and the DNA was transfected into $4\times10^6$ cells of CHO cells using Bio Rad electroporator (350V, 500 μF). The transfected cells were seeded in 96-well culture plate, and cells were cultured in the culture medium with Geneticin (Gibco-BRL) for selecting CHO cells containing the DNA vector. After the selection of several stable transfectant strains, high human IgG producers were screened by ELISA, and used for production of recombinant antibody.

Isolation and Purification of Recombinant Antibody Protein:

CHO cells expressing recombinant antibody were cultured with EX-CELL medium 325-PE (JRH Bioscience, Co., Ltd.). Ten liters of spent culture supernatant was used for purification of antibody protein as follows: The supernatant was applied to MabSelect Protein A column (Amersham Pharmacia Biotech, Co., Ltd.). For adsorption of antibody to protein A, phosphate-buffered saline (PBS) was used, and for elution 20 mM sodium citrate buffer and 50 mM sodium chloride (pH 2.7) was used. The pH of elution fraction was adjusted to 5.5 by addition of 50 mM sodium phosphate buffer (pH 7.0). Further purification of antibody was performed using SP Sepharose column (Amersham Pharmacia Biotech, Co., Ltd.), and PBS was used as an elution buffer.

Purified antibody was sterilized by filtering with Super Cup 100 Capsule membrane filter (0.22 μm diameter pore size). The concentration of the purified antibody was measured by spectrophotometry at 280 nm, in which 1 mg/ml of protein shows 1.4 OD at 280 nm. 17 mg of recombinant C40-IgG1 antibody was purified from 10 liters of CHO cell culture supernatant.

Example 2

This example describes production and characterization of human and chimeric M2 monoclonal antibodies.

KM mice or HAC mice were immunized with synthetic M2 peptide based on the sequence derived from the M2 extracellular domain conjugated to KLH or BSA as a carrier. Most of the mice responded to M2 antigen with high titer as detected by ELISA with M2 peptide as coating antigen. Several anti-M2 human monoclonal antibodies were generated by fusion of splenocytes from 6 high responders with myeloma cells. Twelve monoclonal antibodies were obtained (denoted nos. 2074, C40, L17, L30, L40, L66, N547, S212, S80, S900, F1, and F2), that reacted to M2 peptide and/or M2-BSA conjugates, but did not respond to BSA, KLH (carriers for immunization), mGAD (a synthetic irrelevant peptide derived from mouse Glutamic Acid Decarboxylase (GAD), amino acids 246 to 266) as shown in Table 2. The coding sequences of variable regions of immunoglobulin heavy and light chains were cloned from the original C40 gene, and isotype-changed recombinant antibodies, C40G1 (IgG1) and C40G4 (IgG4), were obtained using a CHO cell expression system (Example 1).

The coding sequences of variable regions of immunoglobulin heavy and light chains of antibodies L66 and N547 are illustrated below. Leader sequences (underlined) are followed by the variable region.

N547_HV_DNA (SEQ ID NO: 34)
ATGGAGTTTGGGCTGAGCTGGATTTTCCTTACTGCTATTTTAAAAGGTGT

CCAGTGTGAGGTGCAACTGGTGGAGTCTGGGGGAGGCTTGGTAAAGCCTG

GGGGGTCCCTTAGACTCTCCTGTGCAGCCTCTGGATTCACTTTCAGTAAC

GCCTTGATGAGCTGGGTCCGCCAGGCTCCAGGGAAGGGACTGGAGTGGGT

TGGCCGTATTAAAAGCAAAACTAATGGTGGGACAACAGACTACGCTGCAC

CCGTGAAAGGCAGATTCACCATCTCAAGAGATGATTCAAAAAACACGCTG

TATCTGCAAATGAACAGCCTGAAAACCGAGGACACAGCCGTGTATTACTG

TACCACCCATCTACGATATTTTGACTGGTTATCTGACTACTGGGGCCAGG

GAACCCTGGTCACCGTCTCCTCA

N547_HV_protein (SEQ ID NO: 28)
MEFGLSWIFLTAILKGVQCEVQLVESGGGLVKPGGSLRLSCAASGFTFSN

ALMSWVRQAPGKGLEWVGRIKSKTNGGTTDYAAPVKGRFTISRDDSKNTL

YLQMNSLKTEDTAVYYCTTHLRYFDWLSDYWGQGTLVTVSS

N547_LV_DNA (SEQ ID NO: 35)
ATGACCTGCTCCCCTCTCCTCCTCACCCTTCTCATTCACTGCACAGGGTC

CTGGGCCCAGTCTGTGTTGACGCAGCCGCCCTCAATGTCTGCGGCCCCAG

GACAGAAGGTCACCATCTCCTGCTCTGGAAGCAGCTCCAACATTGGGAAT

AATTATATATCCTGGTACCAGCAGCTCCCAGGAACAGCCCCCAAAGTCCT

CATTTATGACAATAATAAGCGACCCTCAGGGATTCCTGACCGATTCTCTG

GCTCCAAGTCTGGCACGTCAGCCACCCTGGGCATCACCGGACTCCAGACT

-continued

GGGGACGAGGCCGATTATTACTGCGGATCATGGGATAGCAGCCTGAGTGC

TGGTGTCTTCGGAACTGGGACCAAGGTCACCGTCCTAGGT

N54V_LV_protein (SEQ ID NO: 29)
MTCSPLLLTLLIHCTGSWAQSVLTQPPSMSAPGQKVTISCSGSSSNIGYI

SWYQQLPGTAPLIYDNNKRPSGIPDRFSGSKSGTSATLGITGLQTGDEAY

YCGSWDSSLSAGVFGTGTKVTVLG

L66_HV_DNA (SEQ ID NO: 36)
ATGGAGTTTGGGCTGAGCTGGGTTTTCCTTGTTGCTATTTTAAAAGGTGT

CCAGTGTGAGGTGCAGCTGGTGGAGTCTGGGGGAGGTGTGGTACGGCCTG

GGGGGTCCCTGAGACTCTCCTGTGCAGCCTCTGGATTCACCTTTGATGAT

TATGGCATGAGCTGGGTCCGCCAAGCTCCAGGGAAGGGGCTGGAGTGGGT

CTCTGGTATTAATTGGAATGGTGGTAGCACAGGTTATGCAGACTCTGTGA

AGGGCCGATTCACCATCTCCAGAGACAACGCCAAGAACTCCCTGTATCTG

CAAATGAACAGTCTGAGAGCCGAGGACACGGCCTTGTATTACTGTGCGAG

AGATCGAGTTACTATGGTTCGGGGAGTTATTATGGACTACTACGGTATGG

ACGTCTGGGGCCAAGGGACCACGGTCACCGTCTCCTCA

L66_HV_protein (SEQ ID NO: 30)
MEFGLSWVFLVAILKGVQCEVQLVESGGGVVRPGGSLRLSCAASGFTFDD

YGMSWVRQAPGKGLEWVSGINWNGGSTGYADSVKGRFTISRDNAKNSLYL

QMNSLRAEDTALYYCARDRVTMVRGVIMDYYGMDVWGQGTTVTVSS

L66_LV_DNA (SEQ ID NO: 37)
ATGGCCTGGACTCCTCTCTTTCTGTTCCTCCTCACTTGCTGCCCAGGGTC

CAATTCTCAGACTGTGGTGACTCAGGAGCCCTCTCTGACTGTGTCCCCAA

GAGGGACAGTCACTCTCACCTGTTCTTCCAGCACTGGAGCAGTCACCAGT

GGTTACTATCCAGGCTGGTTCCAGCTGAAACCTGGACAAGCACCCATGTC

ACTGATTTATAGTGCAAGGAAAAAACACTCCTGGACCCCTGCCCGGTTCT

CAGGCTCCCTCCTTGGGGGCAAAGCTGCCCTGACACTGTCAGGTGTGCAG

CCTGAGGACGAGGCTGAGTATTACTGCCTGCTCTACTATGGTGGTGCTTA

TGTCTTCGGAACTGGGACCAAGGTCACCGTCCTAGGT

L66_LV_protein (SEQ ID NO: 31)
MAWTPLFLFLLTCCPGSNSQTVVTQEPSLTVSPRGTVTLTCSSSTGAVTS

GYYPGWFQLKPGQAPMSLIYSARKKHSWTPARFSGSLLGGKAALTLSGVQ

PEDEAEYYCLLYYGGAYVFGTGTKVTVLG

The human/mouse chimera monoclonal antibody no. 2074 and fully human antibodies C40G1, S212, S80, S900, N547, L66, F1, and F2 are $IgG_1$ isotype. C40 is $IgG_4$ isotype, L40 is $IgG_3$ isotype and antibodies L17 and L30 are $IgG_2$ isotypes (Table 2).

TABLE 2

Characteristics of anti-M2 human monoclonal antibodies.

| mAbs | isotype | Light chain | M2 peptide* | M2 on infected cells** | BAS | OVA | KLH | mGAD*** |
|---|---|---|---|---|---|---|---|---|
| C40 | IgG4 | Kappa | +[1] | + | –[2] | – | – | – |
| C40G1 | IgG1 | Kappa | + | + | – | – | – | – |
| L17 | IgG2 | Lambda | + | + | – | – | – | – |
| L30 | IgG2 | Lambda | + | + | – | – | – | – |
| L40 | IgG3 | Lambda | + | + | – | – | – | – |
| L66 | IgG1 | Lambda | + | + | – | – | – | – |
| N547 | IgG1 | Lambda | + | + | – | – | – | – |
| S212 | IgG1 | Lambda | + | + | – | – | – | – |
| S80 | IgG1 | Lambda | + | + | – | – | – | – |
| S900 | IgG1 | Lambda | + | + | – | – | – | – |
| F1 | IgG1 | Kappa | + | + | – | – | – | – |
| F2 | IgG1 | Kappa | + | + | – | – | – | – |

*Most common extracellular portion of M2 protein; the sequence is: SLLTEVETPIRNEWGCRCNDSSD (SEQ ID NO: 1)

**Binding to M2 expressed on A/PR/8/34 and A/HK/8/68 infected MDCK cells at 10 μg/ml

***A synthetic peptide derived from mouse Glutamic Acid Decarboxylase (mGAD), at position from 246 to 266

[1]positive was defined as 2-fold higher than negative control at $OD_{450nm}$

[2]negative was below 0.1 at $OD_{450nm}$

All antibodies recognized M2 expressed on MDCK cells infected with either influenza A/PR/8/34 or A/HK/8/68 strains indicating that the antibodies recognize the native form of M2 expressed by the two different strains even though the sequences of the extracellular domains are slightly different. (FIG. 2). Moreover, antibodies binding to the infected cells were specifically inhibited when M2 peptide was presented (representative data shown in Table 3).

The extracellular portion of the M2 sequence between these two virus strains differs by a single amino acid: a substitution of an aspartic acid to glycine at position 20 in the extracellular portion of M2 in the A/PR/8/34 strain. The sequence derived from A/HK/8/68, so-called universal M2 extracellular portion, is shared among most influenza strains (Neirynck et al., *Nature Med.* 5:1157 (1999)). However, this one mutation abolished binding by a different mouse anti-M2 monoclonal antibody, 14C2 (Gerhard et. al. *Immunological Rev.* 159:95 (1997)).

The reactivity of antibody nos. 2074, N547, L66, L17, C40G1, was comparable and approximately 3 to 5-fold greater than those of antibodies C40G4, S212, and S80, and more than 100-fold greater than F1 and F2 towards A/PR/8/34 virus strain (FIG. 2 and Table 4).

Regarding response to M2 on A/HK/8/68 infected cells, S212, S80, S900, F1 and F2 was approximately 100-fold less than the other antibodies (Table 4). As expected, isotype matched irrelevant human anti-HSA antibody (anti-human serum albumin) did not show any reactivity.

TABLE 3

Specific inhibition of monoclonal antibody binding to M2 on viral infected MDCK cells by 20 μg/ml M2 peptide.

| MAbs* | A/PR/8/34 | M2 | $OD_{450}$ |
|---|---|---|---|
| 2074 | − | − | 0.051 |
| | + | − | 0.904 |
| | + | + | 0.142 |
| N547 | − | − | 0.065 |
| | + | − | 0.504 |
| | + | + | 0.062 |
| L66 | − | − | 0.051 |
| | + | − | 0.931 |
| | + | + | 0.113 |
| C40G1 | − | − | 0.051 |
| | + | − | 0.799 |
| | + | + | 0.195 |

*All antibodies were used at 1 μg/ml concentration.

TABLE 4

Binding capability of anti-M2 antibody to native M2 on MDCK cells infected with two influenza A virus strains.

| | $EC_{50}$ (μg/ml) of Abs* to M2 on MDCK cells infected by | |
|---|---|---|
| mAbs | A/PR/8/34 | A/HK/8/68 |
| 2074 | 0.0891 | 0.1873 |
| C40G1 | 0.1826 | 0.0971 |
| C40G4 | 0.3007 | 0.8414 |
| S212 | 0.5001 | >10** |
| S80 | 0.2176 | >10** |
| S900 | 0.2063 | >10** |
| N547 | 0.1042 | 0.4661 |
| L17 | 0.1511 | 0.5968 |
| L30 | 0.1747 | 3.4914 |
| L66 | 0.1169 | 0.2289 |
| F1 | >10** | >10** |
| F2 | >10** | >10** |

*$OD_{450}$ of no. 2074 at 10 μg/ml dose was set as 100% for $EC_{50}$ calculation. The background is below 0.1.
**These Abs are very weak binder, and the $OD_{450}$ at 10 μg/ml is even less than half of the $OD_{450}$ of no. 2074 antibody at the same concentration.

Binding activity of anti-M2 antibodies to M2 and mutant M2 peptides was analyzed with two types of ELISA assay, M2 peptide based ELISA assay and an M2-BSA conjugate based ELISA assay. Twenty two different M2 peptides (SEQ ID NOs:1-22, Table 5) that have been reported in influenza A virus strains were analyzed for anti-M2 antibody binding. The sequences of M2 variant peptides used in this study were found in Genbank from at least one viral isolate. M2: A/Hong Kong/1/68 (H3N2), M2EG: A/New York/687/1995 (H3N2), M2K: A/Wisconsin/3523/88 (H1N1), M2G: A/Puerto Rico/8/34 (H1N1), M2FG: A/X-31 (H3N2), M2DLTGS: A/Hong Kong/485/97 (H5N1), M2LTKGS: A/Hong Kong/542/97 (H5N1), M2LTGS: A/Hong Kong/156/97 (H5N1), M2LTGEKS: A/Hong Kong/1074/99 (H9N2), M2TGEKS: A/Canada/rv504/2004 (H7N3), M2TES: A/Viet Nam/1203/2004 (H5N1), M2TGS: A/chicken/Shanghai/F/98 (H9N2), M2TGEK: A/Netherlands/33/03 (H7N7), M2KTGEKS: A/Quail/Arkansas/16309-7/94 (H7N3NSA), M2TDGEKS: A/chicken/Pennsylvania/13552-1/98 (H7N2NSB), M2HTGEKS: A/chicken/California/1002a/00 (H6N2), M2P: A/swine/Quebec/192/81 (H1N1), M2SG: A/swine/Tennessee/25/77 (H1N1), M2TGE: A/DK/ST/5048/2001 (H3N8), M2KGENS: A/Turkey/VA/158512/02 (H7N2), M2 GHTGKS: A/chicken/HongKong/SF1/03 (H9N2), M2PHTGS: A/chicken/HongKong/YU427/03 (H9N2). Among these 22 M2 peptides, the following ten types of M2 mutations were reported in both human and avian virus strains: M2, M2EG, M2K, M2DLTGS, M2LTKGS, M2LTGS, M2LTGEKS, M2TGEKS, M2TES and M2TGS. M2G and M2FG mutations were reported only in human virus strains. The remaining ten M2 mutations were reported in influenza A virus strains in species other than human.

TABLE 5

Sequence of M2 mutant peptides.

| Variant | Amino Acid Sequence | SEQ ID NO |
|---|---|---|
| M2 | SLLTEVETPIRNEWGCRCNDSSD | (SEQ ID No.1) |
| M2EG | SLLTEVETPIRNEW**E**CRCN**G**SSD | (SEQ ID No.2) |
| M2K | SLLTEVETPIRNEWGC**K**CNDSSD | (SEQ ID No.3) |
| M2G | SLLTEVETPIRNEWGCRCN**G**SSD | (SEQ ID No.4) |
| M2FG | S**F**LTEVETPIRNEWGCRCN**G**SSD | (SEQ ID No.5) |
| M2DLTGS | SLLTEV**D**T**LT**RN**G**WGCRC**S**DSSD | (SEQ ID No.6) |
| M2LTKGS | SLLTEVET**LTK**N**G**WGCRC**S**DSSD | (SEQ ID No.7) |
| M2LTGS | SLLTEVET**LT**RN**G**WGCRC**S**DSSD | (SEQ ID No.8) |
| M2LTGEKS | SLLTEVET**LT**RN**G**W**E**C**K**C**S**DSSD | (SEQ ID No.9) |
| M2TGEKS | SLLTEVETP**T**RN**G**W**E**C**K**C**S**DSSD | (SEQ ID No.10) |
| M2TES | SLLTEVETP**T**RNEW**E**CRC**S**DSSD | (SEQ ID No.11) |
| M2TGS | SLLTEVETP**T**RN**G**WGCRC**S**DSSD | (SEQ ID No.12) |
| M2TGEK | SLLTEVETP**T**RN**G**W**E**C**K**CNDSSD | (SEQ ID No.13) |
| M2KTGEKS | SLLTEVKTP**T**RN**G**W**E**C**K**C**S**DSSD | (SEQ ID No.14) |
| M2TDGEKS | SLLTEVETP**T**R**DG**W**E**C**K**C**S**DSSD | (SEQ ID No.15) |
| M2HTGEKS | SLLTEVET**HT**RN**G**W**E**C**K**C**S**DSSD | (SEQ ID No.16) |
| M2P | SL**P**TEVETPIRNEWGCRCNDSSD | (SEQ ID No.17) |
| M2SG | SLLTEVETPIR**S**EWGCRCNDS**G**D | (SEQ ID No.18) |
| M2TGE | SLLTEVETP**T**RN**G**W**E**CRCNDSSD | (SEQ ID No.19) |
| M2KGENS | SLLTEVETPIR**KG**W**E**C**N**C**S**DSSD | (SEQ ID No.20) |
| M2GHTGKS | SLLT**G**VET**HT**RN**G**WGC**K**C**S**DSSD | (SEQ ID No.21) |
| M2PHTGS | SLL**P**EVET**HT**RN**G**WGCRC**S**DSSD | (SEQ ID No.22) |

Underlined bold letters are the mutated residues compared to M2 sequence of SEQ ID NO: 1.

Human anti-M2 antibody nos. L66, N547 and C40G1 were used in this study. A mouse anti-M2 antibody, 14C2 (Affinity Bioreagents, Golden, Colo.), was used as a reference control.

For the M2 peptide based ELISA assay, M2 peptide and M2 mutant peptides were diluted in carbonate-bicarbonate buffer (pH 9.3-9.5) and coated on Nunc MaxiSorp 96 well flat bottom plates (Fisher, Calif.) at 5 μg/mL overnight at 4° C. After washing twice with wash buffer (0.05% Tween 20 in PBS), plates were blocked with blocking buffer (1% BSA and 5% FCS in PBS) for 1 hr at room temperature, followed by the incubation with 50 μl of 10 μg/ml of M2 monoclonal antibody for 1 hr at room temperature. The plates were then washed 3 times with wash buffer, and incubated with HRP-conjugated goat anti-human IgG (1:20,000) for 1 hr at room temperature, followed by the development with TMB substrate. The absorbance (O.D.) was read at 450 nm within 30 min. The O.D. was compared to the O.D. of the wild-type M2 peptide (i.e. "M2", SEQ ID NO:1) in each antibody, and the percentage of binding as compared with the binding to the wild-type M2 peptide (SEQ ID NO:1) was calculated in each mutant M2 peptide.

Binding activity was categorized into three categories based upon the percentage calculated: +(more than 50%), W (10%~50%) and −(less than 10%). The results are shown in Table 6.

In general, L66 and N547 showed a similar binding profile to these 22 M2 peptides in the peptide-based ELISA assay at 10 μg/ml. In particular, L66 and N547 bound to M2EG, M2K, M2G, M2DLTGS, M2LTKGS, M2LTGS, M2LTGEKS, M2TGEKS, M2TES, M2TGS, M2TGEK, M2KTGEKS, M2TDGEKS, M2HTGEKS, M2SG, M2TGE, M2KGENS, M2 GHTGKS, and M2PHTGS to a level comparable to their binding to M2. No (less than 10%) or weak (10%~50%) binding activity was shown to M2FG and M2P (Table 6). L66 and N547 significantly tolerated more M2 mutations than the 14C2 murine antibody under the assay conditions. Compared to L66 and N547, C40G1 exhibited somewhat less tolerance to M2 mutations. For example, C40G1 did not bind to M2LTKGS, M2LTGS, M2KTGEKS, M2HTGEKS, M2KGENS, M2 GHTGKS or M2PHTGS, and bound weakly to M2LTGEKS, M2TGS, M2TGEK and M2TGE. Nevertheless, C40G1 antibody tolerated M2 mutations such as M2DLTGS, M2TGEKS and M2TDGEKS as compared to the 14C2 murine antibody under the assay conditions.

TABLE 6

Binding activity of anti-M2 antibodies (at 10 μg/ml) to M2 and M2 mutant peptides in a peptide-based ELISA assay.

| Variant | L66 | N547 | C40G1 | 14C2 |
|---|---|---|---|---|
| M2 | + | + | + | + |
| M2EG | + | + | + | + |
| M2K | + | + | + | + |
| M2G | + | + | + | + |
| M2FG | W | W | + | + |
| M2DLTGS | + | + | + | W |
| M2LTKGS | + | + | − | − |
| M2LTGS | + | + | − | − |
| M2LTGEKS | + | + | W | − |
| M2TGEKS | + | + | + | − |
| M2TES | + | + | + | + |
| M2TGS | + | + | W | + |
| M2TGEK | + | + | W | + |
| M2KTGEKS | + | + | − | − |
| M2TDGEKS | + | + | + | − |
| M2HTGEKS | + | + | − | − |
| M2P | W | − | + | + |
| M2SG | + | + | + | + |
| M2TGE | + | + | W | − |
| M2KGENS | + | + | − | + |
| M2GHTGKS | + | + | − | − |
| M2PHTGS | + | + | − | − |

Percentage of O.D. compared to O.D. of M2 sequence of SEQ ID NO: 1. >50%: + 10~50%: W <10%: −

For the M2-BSA conjugate based ELISA assay, peptide conjugates (M2-BSA) were prepared using the EDC conjugation kit (PIERCE Biotechnology, Inc., Rockford, Ill.) according to the manufacturer's instructions. M2 peptide and M2 mutant peptides conjugated with BSA diluted in carbonate-bicarbonate buffer (pH 9.3-9.5) were coated on Nunc MaxiSorp 96 well flat bottom plates (Fisher, Calif.) at 5 μg/mL overnight at 4° C. After washing twice with wash buffer (0.05% Tween 20 in PBS), plates were blocked with blocking buffer (1% BSA and 5% FCS in PBS) for 1 hr at room temperature, followed by the incubation with 50 μl of 2-fold serial dilutions of M2 monoclonal antibody for 1 hr at room temperature. The plates were then washed 3 times with wash buffer, and incubated with HRP-conjugated goat anti-human IgG (1:20,000) for 1 hr at room temperature, followed by the development with TMB substrate. The absorbance was read at 450 nm within 30 min. EC50 was calculated using Prism4 software. Binding activity was categorized into the three categories based upon the EC50 value: "++" (EC50 is less than $10^{-9}$M); "+" (EC50 is between $10^{-9}$M and $10^{-8}$M); and "−" (EC50 is higher than $10^{-8}$M). The results are shown in Table 7.

In general, L66 and N547 showed a similar binding profile to these 22 M2 peptides as in the M2-BSA ELISA. In particular, L66 and N547 bound to M2, M2K, M2LTGEKS, M2TES, M2TGEK, M2KGENS and M2 GHTGKS, and weakly bound to M2EG (Table 7). Interestingly, L66 and N547 bound to M2LTGEKS, M2TGEK and M2 GHTGKS, to which 14C2 murine antibody did not bind. On the other hand, C40G1 and 14C2 antibodies bound to M2, M2EG, M2K, M2G, M2FG, M2TES, M2P and M2SG, and weakly bound to M2DLTGS.

TABLE 7

Binding activity of anti-M2 antibodies to M2 an dM2 mutant peptides in an M2-BSA-based ELISA assay.

| Variant | L66 | N547 | C40G1 | 14C2 |
|---|---|---|---|---|
| M2 | ++ | ++ | ++ | ++ |
| M2EG | + | + | ++ | ++ |
| M2K | ++ | ++ | ++ | ++ |
| M2G | − | − | ++ | ++ |
| M2FG | − | − | ++ | ++ |
| M2DLTGS | − | − | + | + |
| M2LTKGS | − | − | − | − |
| M2LTGS | − | − | − | − |
| M2LTGEKS | ++ | ++ | − | − |
| M2TGEKS | − | − | − | + |
| M2TES | ++ | ++ | ++ | ++ |
| M2TGS | − | − | − | ++ |
| M2TGEK | ++ | ++ | − | − |
| M2KTGEKS | − | − | − | − |
| M2TDGEKS | − | − | − | − |
| M2HTGEKS | − | − | − | − |
| M2P | − | − | ++ | ++ |
| M2SG | − | + | ++ | ++ |
| M2TGE | − | − | − | ++ |
| M2KGENS | ++ | ++ | − | ++ |
| M2GHTGKS | ++ | ++ | − | − |
| M2PHTGS | ++ | − | − | − |

Binding activity was categorized as follows based on the EC50 value. EC50 < $10^{-9}$M: ++ $10^{-9}$M < EC50 < $10^{-8}$M: + EC50 > $10^{-8}$M: −

Example 3

This example describes the identification of minimal binding sequences of several exemplary invention M2 monoclonal antibodies.

Minimal binding sequences of antibodies were mapped using various peptides having truncations of the M2 N-terminus and C-terminus (Table 8 and 9). The epitope of each antibody is within the minimal binding sequence.

N547 binds well to the M2 peptide with one amino acid deleted from the N-terminus (M16, SEQ ID NO:56), but did not bind to M2 peptide with two amino acids deleted (M15, SEQ ID NO:57). N547 binds well to M2 peptide with seven amino acids deleted from C-terminus (NM16, SEQ ID NO:23), but did not bind to M2 peptide with eight amino acids deleted (NM15, SEQ ID NO:66). This data indicates that the antigenic determinant (i.e. epitope) of N547 is within an amino acid sequence, LLTEVETPIRNEWGC (SEQ ID NO:25).

L66 did not tolerate any amino acid deletions from N-terminus, but binds well to M2 peptides with up to seven amino acids deleted from the C-terminus. This data indicates that the epitope recognized by L66 is within an amino acid sequence SLLTEVETPIRNEWGC (SEQ ID NO:23).

C40G1 tolerated up to seven amino acids deleted from the N-terminus and up to 10 amino acids deleted from the C-terminus. This data indicates that the epitope recognized by C40G1 is within an amino acid sequence, TPIRNE (SEQ ID NO:23).

Mouse anti-M2 antibody 14C2 tolerated up to two amino acids deleted from the N-terminus and up to nine amino acids deleted from the C-terminus. This data indicates that the epitope recognized by 14C2 is within an amino acid sequence, LTEVETPIRNEW (SEQ ID NO:71).

TABLE 8

Binding activity of anti-M2 monoclonal antibodies to M2 peptides.

| Name | SEQ ID NO | Amino acid sequence | ELISA(OD450)* L66 | C40G1 | N547 | 14C2 |
|---|---|---|---|---|---|---|
| M2 | 1 | SLLTEVETPIRNEWGCRCNDSSD | 0.51 | 2.56 | 0.51 | 1.97 |
| M16 | 56 | LLTEVETPIRNEWGCR | 0.24 | 2.64 | 0.68 | 1.78 |
| M15 | 57 | LTEVETPIRNEWGCR | 0.21 | 2.73 | 0.07 | 1.81 |
| M12 | 58 | VETPIRNEWGCR | 0.19 | 2.71 | 0.07 | 0.04 |
| CM17 | 59 | ETPIRNEWGCRCNDSSD | 0.12 | 2.78 | 0.08 | 0.04 |
| CM16 | 60 | TPIRNEWGCRCNDSSD | 0.09 | 0.76 | 0.08 | 0.04 |
| CM15 | 61 | PIRNEWGCRCNDSSD | 0.09 | 0.11 | 0.08 | 0.04 |
| CM14 | 62 | IRNEWGCRCNDSSD | 0.08 | 0.10 | 0.08 | 0.05 |
| CM13 | 63 | RNEWGCRCNDSSD | 0.08 | 0.11 | 0.08 | 0.05 |
| CM12 | 64 | NEWGCRCNDSSD | 0.08 | 0.10 | 0.07 | 0.04 |
| NM17 | 65 | SLLTEVETPIRNEWGCR | 0.99 | 2.41 | 1.04 | 1.55 |
| NM16 | 23 | SLLTEVETPIRNEWGC | 1.04 | 2.37 | 1.13 | 1.80 |
| NM15 | 66 | SLLTEVETPIRNEWG | 0.20 | 2.51 | 0.09 | 1.48 |
| NM14 | 67 | SLLTEVETPIRNEW | 0.22 | 2.49 | 0.16 | 1.75 |
| NM13 | 68 | SLLTEVETPIRNE | 0.13 | 2.41 | 0.06 | 0.04 |
| NM12 | 69 | SLLTEVETPIRN | 0.12 | 0.12 | 0.16 | 0.05 |
| NM11 | 70 | SLLTEVETPIR | 0.09 | 0.31 | 0.07 | 0.04 |

*All antibodies were used at 10 μg/ml.

TABLE 9

Minimal binding sequences of anti-M2 antibodies

| Antibody | Minimal binding sequence | SEQ ID NO |
|---|---|---|
| L66 | SLLTEVETPIRNEWGC | 23 |
| C40G1 | TPIRNE | 24 |
| N547 | LLTEVETPIRNEWGC | 25 |
| 14C2 | LTEVETPIRNEW | 71 |

Example 4

This example describes animal model studies indicating that administering an M2 monoclonal antibody of the invention before or after the animal is infected with influenza virus protects against a lethal challenge of virus.

Figure 5:
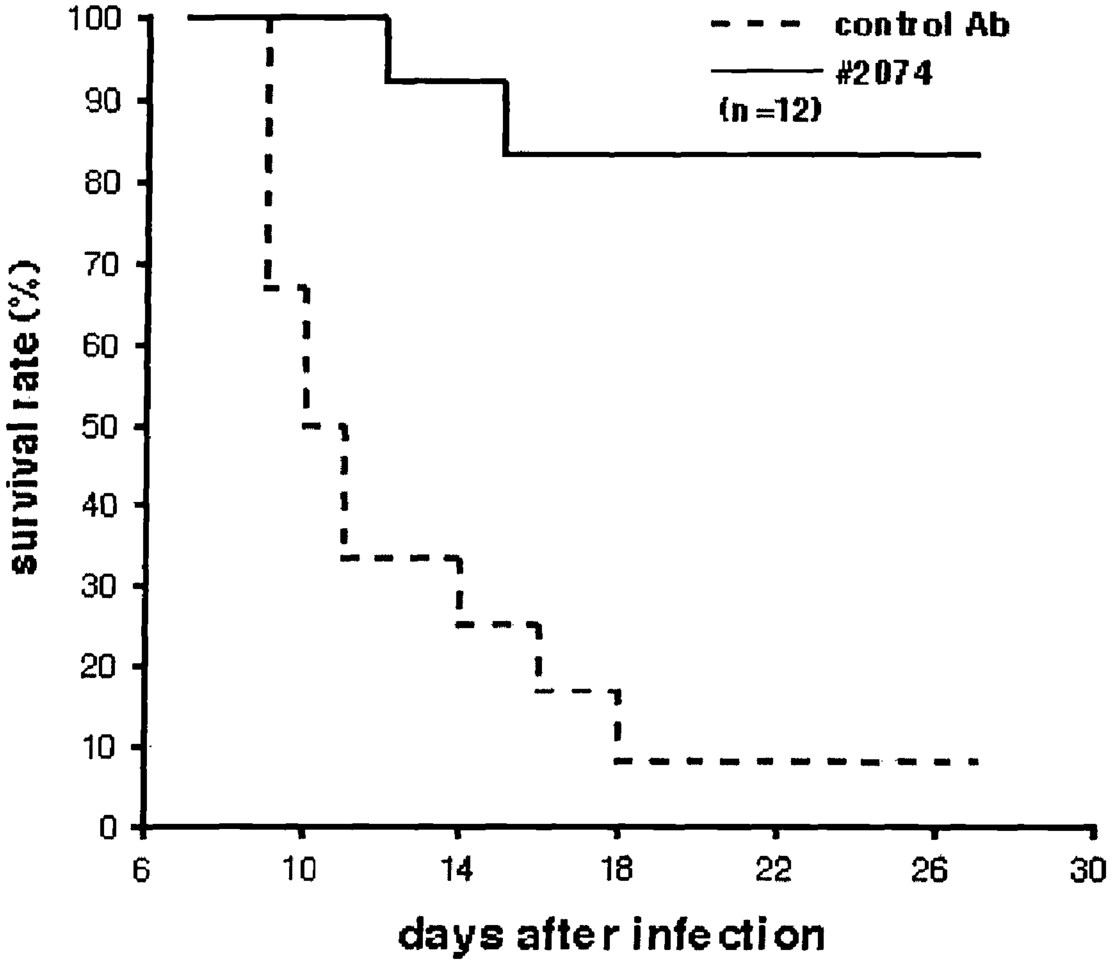
FIG. 5 shows prophylactic protection of animals administered M2 antibody no. 2074.

In Vivo Efficacy of Anti-M2 Monoclonal Antibody for Prophylaxis Treatment (Prior to Virus Infection) in a Mouse Influenza A Virus Model:

To evaluate the efficacy of anti-M2 human/mouse chimera monoclonal antibody in an animal, antibody no. 2074 was administered at a dose of 200 μg/mouse intraperitoneally to female C57BL/6J mice (8~10 weeks old). One day after initiation of treatment, anesthetized mice (15 μl/g of Avertin (1:1 w/v of 2,2,2 tribromoethanol:tert-amyl-OH, Sigma, St. Louis, Mo.)) were infected with 30 μl (3.2-fold of $MLD_{50}$) of a lethal dose of influenza A/PR/8/34 (ATCC) intranasally. Two days after infection, the mice received another dose of no. 2074 antibody (200 μg/mouse) intraperitoneally. As a control, an isotype matched human monoclonal anti-HSA IgG1 antibody generated from a KM Mouse™ was used (Kirin, Japan). Mice were observed daily for 27 days for survival. The surviving mice were sacrificed after that time and the lungs were removed for detection of virus and histological analysis. The survival results are shown in FIG. 5. The results of lung virus titer analysis are illustrated in Table 10.

Anti-M2 antibody no. 2074 treated mice were significantly protected. Ten of 12 mice were still alive over the 27-day period of observation. In contrast, in the control group, 11 of 12 mice died within 18 days post infection.

The surviving mice (10 from the anti-M2 treated group and one from the control group) were sacrificed at day 27 after infection and the lungs were removed for viral titer and tissue analysis. No detectable virus from the lungs of the mice from either group was found by a viral plaque assay, while for the positive control, the titer of A/HK/8/68 virus was $5.95\times10^3$ pfU/ml (Table 10). This data indicates that administration of anti-M2 antibody can prevent an increase in viral titer in the lung in mice, and facilitate viral clearance in the mouse.

TABLE 10

Viral titer of lungs from mice at day 27 after A/PR/8/34 infection.

| Samples | Dilution | No of plaques | pfu/ml |
|---|---|---|---|
| 1-L1* | $10^{-1}$ | 0 | <50** |
| 1-I2 | $10^{-1}$ | 0 | <50 |
| 1-L3 | $10^{-1}$ | 0 | <50 |
| 1-L4 | $10^{-1}$ | 0 | <50 |
| 1-L5 | $10^{-1}$ | 0 | <50 |
| 1-L11 | $10^{-1}$ | 0 | <50 |
| A/HK/8/68*** | $10^{-3}$ | 59.5 | $5.95\times10^3$ |

*Lung homogenates from A/PR/8/34 infected mice. L1 to L5: samples from anti-M2 antibody treated group. L11: sample from isotype matched antibody treated group. (control)
**Threshold of virus detection is 50 pfu/ml.
***Virus used as positive control for the assay.

In another study, mice administered anti-M2 antibodies (30 μg/mouse) nos. L66 or C40G1 or anti-M2 antibody no. N547 (10 μg/mouse) intraperitoneally were challenged with a lethal dose of A/HK/1/68 intranasally one day after the administration of the antibody. As an isotype control, anti-HSA specific human IgG1 antibody was used. Each group consisted of 8 to 10 mice.

Figure 6:
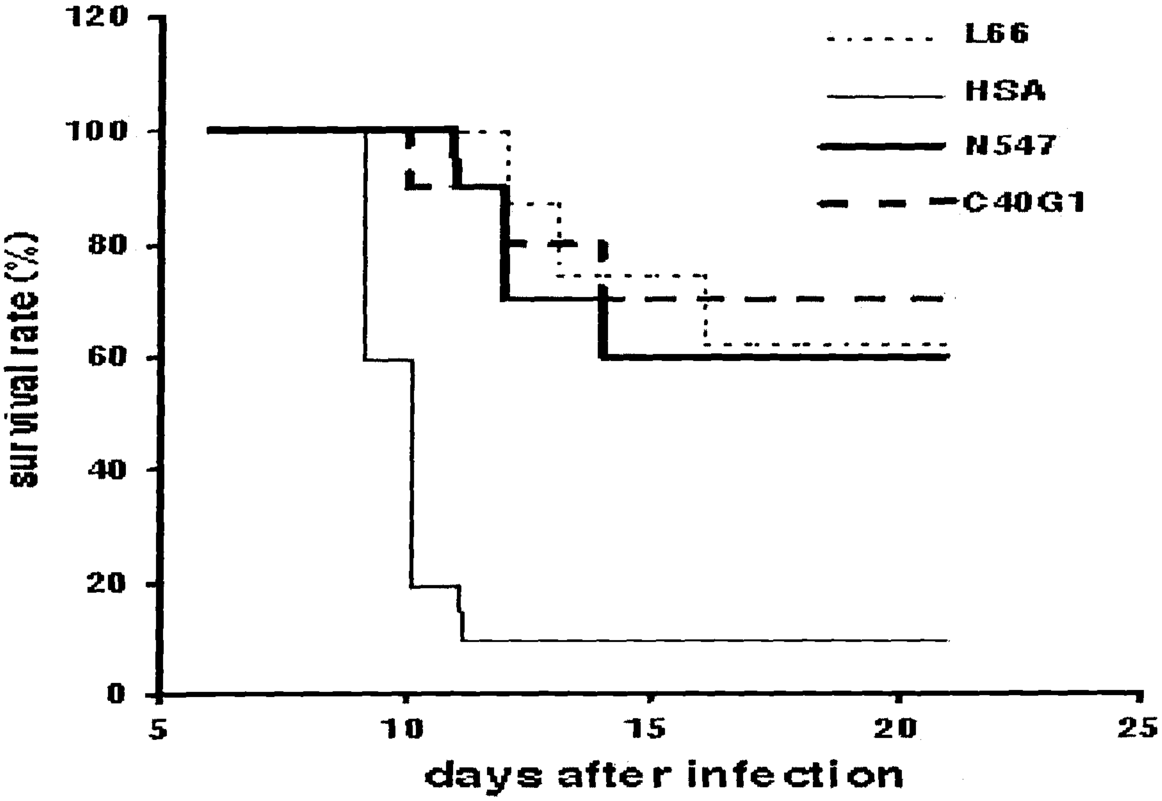
FIG. 6 shows prophylactic protection of animals administered M2 antibody nos. L66, N547 and C40G1.

Compared to the survival rate of anti-HAS antibody treated group significant protection from virus infection induced death was observed in the groups treated with L66, N547 or C40G1 antibodies (FIG. 6).

In Vivo Efficacy of Anti-M2 mAb for Therapeutic Treatment (after Virus Infection) in a Mouse Influenza A Virus Model.

Anesthetized female C57BL/6J mice (8~10 weeks old) were infected with 30 μl of a lethal dose of influenza A/PR/8/34 (ATCC) or A/HK/1/68 (CDC, Atlanta, Ga.) intranasally. Anesthetization was performed using Avertin as previously described. Mice were observed daily for 24 days for survival.

To determine efficacy of the anti-M2 monoclonal antibodies for therapeutic treatment of influenza virus, various anti-M2 antibodies were administered after virus infection. Antibodies studied were no. 2074, C40G1, C40G4, L30, F1, F2, L66 and N547.

In a first study, two and four days after a lethal dose virus challenge of influenza A/PR/8/34 was given to C57BL/6J mice, anti-M2 antibody no. 2074 (200 μg/mouse) was administered by intraperitoneal injection (12 mice in total). The control group (total 12 mice) received isotype matched irrelevant human monoclonal antibody (anti-HSA (IgG1) from Kirin Brewery Co., Ltd., Japan).

Figure 7:
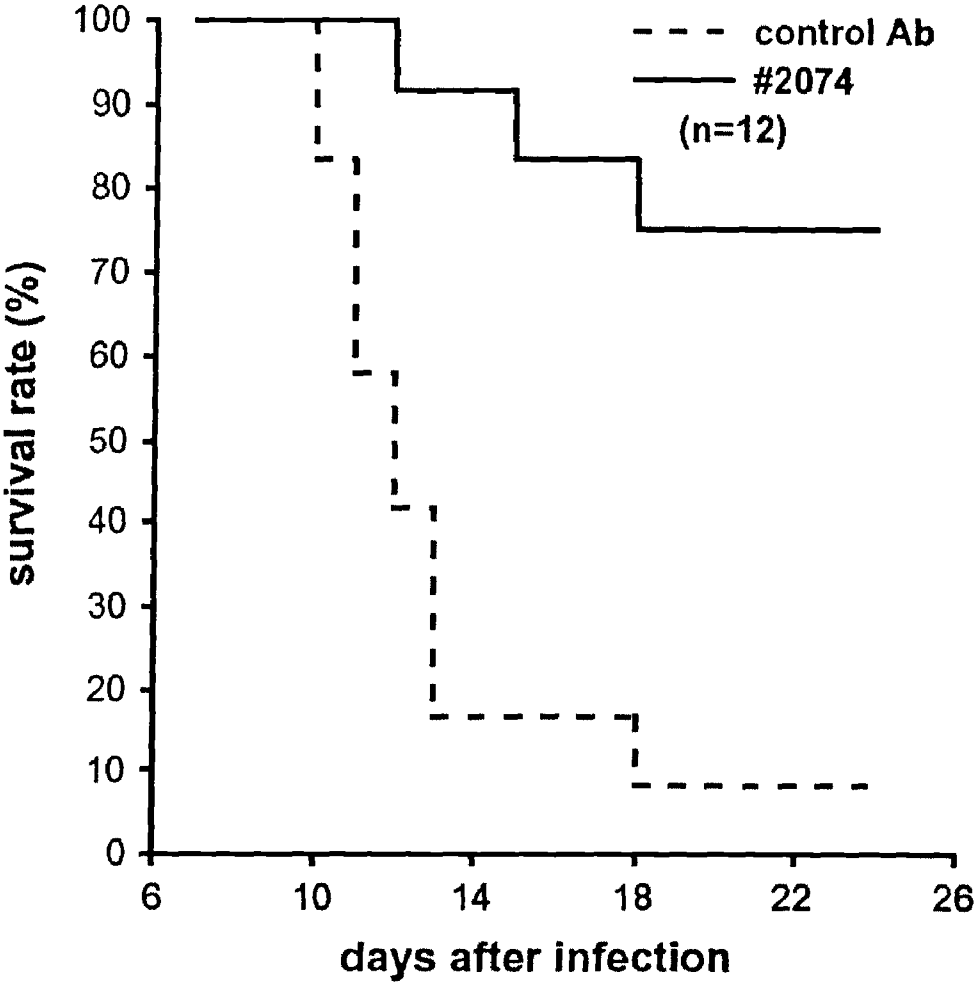
FIG. 7 shows therapeutic protection of animals administered M2 antibody no. 2074.

In the control group, 11 of 12 mice died within 18 days post infection (FIG. 7). In the antibody no. 2074 group, nine of 12 mice survived virus challenge at day 24. Thus, anti-M2 human/mouse chimera monoclonal antibody no. 2074 significantly increased survival of mice infected with A/PR/8/34 virus.

In a second study, a lethal dose virus challenge of influenza A/PR/8/34 was given to C57BL/6J mice, and one, two and three days later, anti-M2 antibodies C40G1, C40G4, L30, F1, F2 and no. 2074 (as a positive control) were administered at 200 μg/mouse in each time by intraperitoneal injection (n=8 or 12 mice in each group). The control group (total of 8 or 12 mice) received anti-HSA specific human IgG1 antibody injection.

Figure 3:
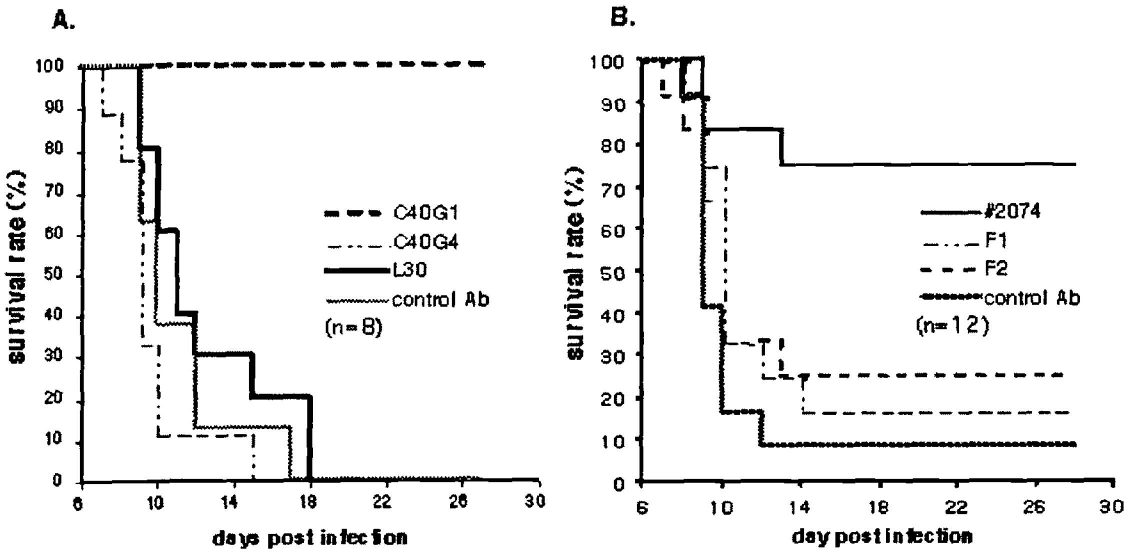
FIG. 3 shows a comparison of protective efficacy of A) C40G1, C40G4 and L30; and B) no. 2074, F1 and F2 antibodies, and that IgG1 isotype M2 antibodies provide greater protection of animals from a lethal virus challenge than antibodies with weak binding affinity to M2 on viral infected MDCK cells (i.e. F1 and F2) or other subclass of IgG (i.e., L30 ($IgG_2$), C40G4 ($IgG_4$)).

L30, C40G4, F1 and F2 antibodies did not detectably prolong survival of virus infected mice (FIGS. 3A, B). In contrast, C40G1 antibody showed clear protection from the viral challenge, and all mice in this group were alive even after 30 days post infection (FIG. 3A).

Binding affinity of C40G1, L30 and C40G4 antibodies to either M2 expressed on A/PR/8/34 infected cells (FIG. 4B, Table 4) or M2-BSA conjugate (FIG. 4A) were not significantly different among each other. C40G1 is an $IgG_1$ and C40G4 is an $IgG_4$ and each have the same antigen binding site, since both of them came from C40 antibody. Since L30 (IgG2) and C40G4 (IgG4) did not show protection from virus challenge whereas C40G1 did significantly protect, IgG1 type antibody appears to be a better candidate for in vivo use.

Figure 4:
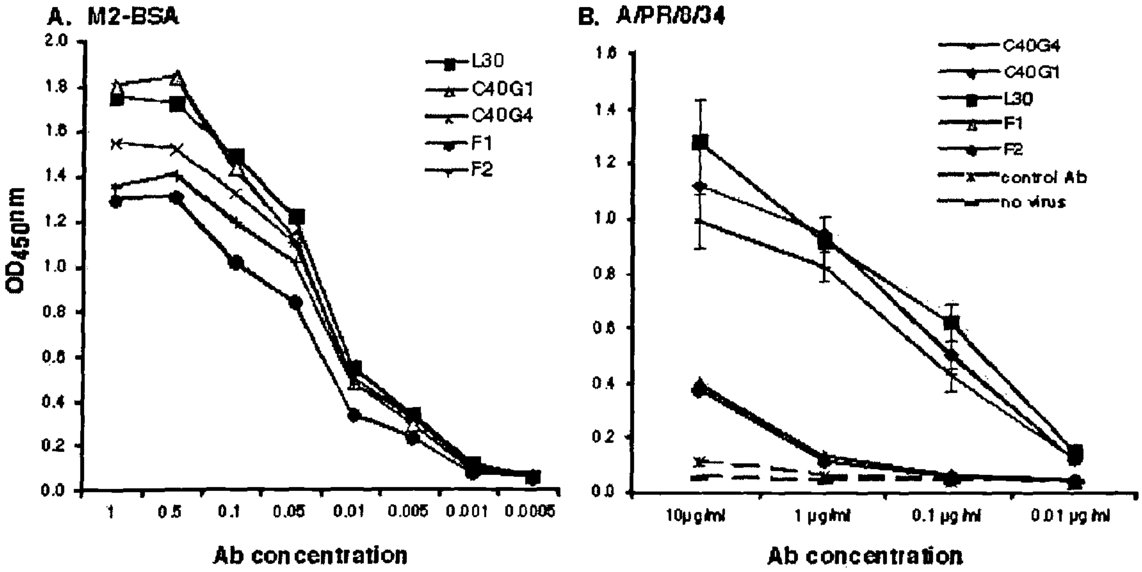
FIG. 4 illustrates a comparison of M2 antibody binding to A) M2 peptide/BSA and B) M2 expressed on influenza virus infected cells.

F1 and F2 antibodies bound poorly to M2 on viral infected cells although these antibodies bind to M2-BSA conjugate well (FIGS. 4A, B, Table 4). The poor binding of F1 and F2 antibodies to M2 on viral infected cells may account for the lack of detectable protective effect in vivo.

A third in vivo study was performed to evaluate the efficacy of anti-M2 antibody nos. L66 and N547. Mice were challenged with a lethal dose of A/HK/1/68 intranasally and were administered with 100 μg/mouse of L66 or N547 antibodies intraperitoneally one day after infection. As an isotype control, anti-HSA specific human IgG1 antibody was administered. Each group consisted of 10 mice.

Figure 8:
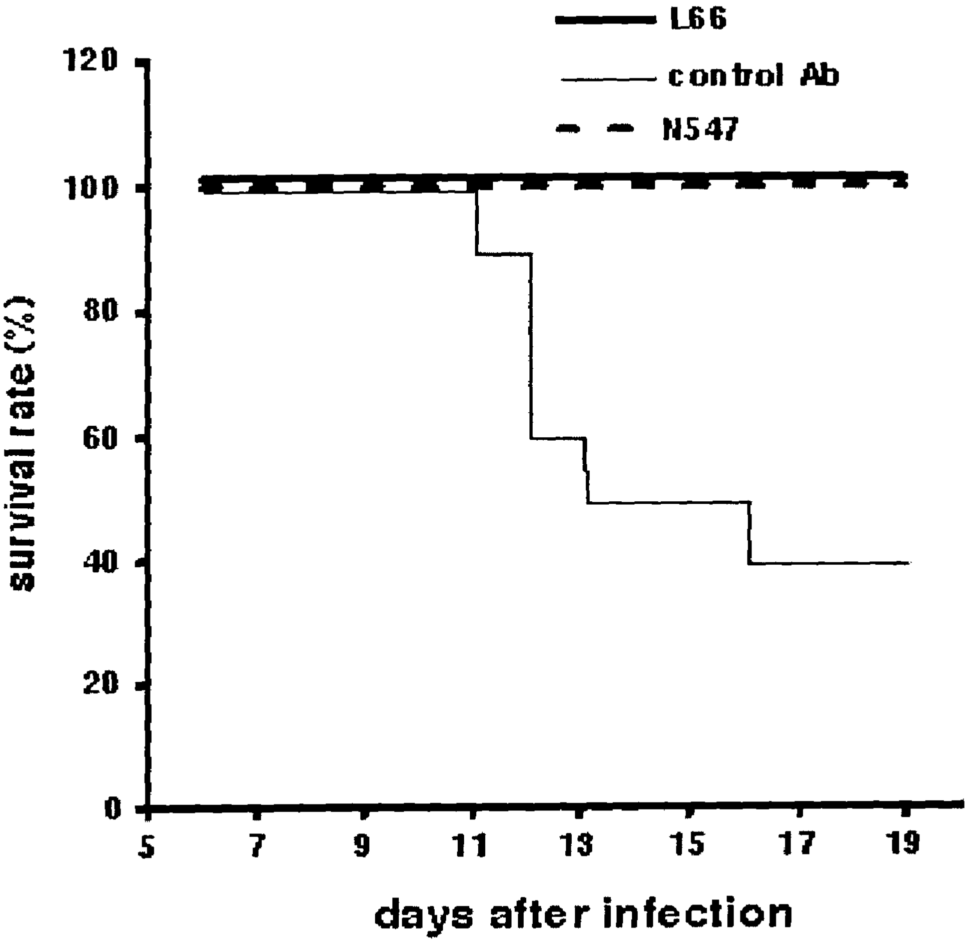
FIG. 8 shows therapeutic protection of animals administered M2 antibody nos. L66 and N547.

Survival rate of anti-HSA antibody treated group was 40% on day 19 after virus infection (FIG. 8). In contrast, 100% protection from virus infection induced death was observed in L66 and N547 antibodies treated groups (FIG. 8).

The data indicates that anti-M2 antibodies are effective in animals if administered even after virus infection. The antibodies can therefore be used for influenza A prophylaxis as well as therapeutically.

What is claimed:

1. An isolated antibody that specifically binds to an influenza protein M2 extracellular domain, wherein the antibody binds to at least two peptides selected from M2TGEKS (SEQ ID NO:10), M2TDGEKS (SEQ ID NO:15), M2LTGEKS (SEQ ID NO:9) and M2TGE (SEQ ID NO:19), as determined by a peptide based ELISA assay.

2. An isolated antibody that specifically binds to an influenza protein M2 extracellular domain, wherein the antibody has a binding activity (EC50) of less than $10^{-8}$ M for M2LTGEKS (SEQ ID NO:9) and M2TGEK (SEQ ID NO:13), as determined by an ELISA assay of binding between the antibody and an M2LTGEKS-BSA or M2TGEK-BSA conjugate.

3. An isolated antibody that specifically binds to an influenza protein M2 extracellular domain, wherein the antibody has a binding activity (EC50) of less than $10^{-9}$M for M2LTGEKS (SEQ ID NO:9) and M2TGEK (SEQ ID NO:13), as determined by an ELISA assay of binding between the antibody and an M2LTGEKS-BSA or M2TGEK-BSA conjugate.

4. The isolated antibody of claim 2 or 3, wherein the antibody has a binding activity (EC50) of less than $10^{-8}$ M for one or more of M2TGS (SEQ ID NO:12) or M2TGE (SEQ ID NO:19).

5. An isolated antibody that specifically binds to a minimal binding sequence that is SLLTEVETPIRNEWGC (SEQ ID NO:23), wherein the minimal binding sequence for antibody binding is neither LTEVETPIRNEW (SEQ ID NO:71) nor EVETPIRN (SEQ ID NO:72).

6. The antibody of any of claims 1 to 3, wherein the antibody does not bind to LTEVETPIRNEW (SEQ ID NO:71) and EVETPIRN (SEQ ID NO:72).

7. The antibody of claim 5, wherein the antibody comprises the heavy and light chain variable region sequence of the antibody produced by the hybridoma L66 (ATCC PTA-5048).

8. The antibody of claim 5, wherein the antibody comprises the mature portion of heavy chain variable region sequence as shown in SEQ ID NO:30 and the mature portion of light chain variable region sequence as shown in SEQ ID NO:31.

9. An isolated antibody that specifically binds to a minimal binding sequence that is TPIRNE (SEQ ID NO:24), wherein the minimal binding sequence for antibody binding is neither LTEVETPIRNEW (SEQ ID NO:71) nor EVETPIRN (SEQ ID NO:72).

10. The antibody of claim 9, wherein the antibody comprises the heavy and light chain variable region sequence of the antibody produced by the CHO cell C40G1 (ATCC PTA-5050).

11. The antibody of claim 9, wherein the antibody comprises the mature portion of heavy chain variable region sequence as shown in SEQ ID NO:26 and the mature portion of light chain variable region sequence as shown in SEQ ID NO:27.

12. The antibody of any of claims 1 to 3, wherein the antibody is a subclass selected from human IgG1, human IgG2, human IgG3 and human IgG4.

13. The antibody of any of claims 1 to 3, wherein the subclass of the antibody is human IgG1.

14. The antibody of any of claims 1 to 3, wherein the antibody is selected from IgG, IgA, IgM, IgE, and IgD isotypes.

15. The antibody of claim 14, wherein the IgG isotype is selected from $IgG_1$, $IgG_2$, $IgG_3$ and $IgG_4$.

16. The antibody of any of claims 1 to 3, wherein the antibody inhibits influenza virus infection of a cell, influenza virus proliferation or influenza virus replication in vitro or in vivo.

17. The antibody of any of claims 1 to 3, wherein the antibody inhibits influenza binding of a cell in vitro or in vivo.

18. The antibody of any of claims 1 to 3, wherein the antibody inhibits increases in influenza virus titer, decreases influenza virus titre, decreases influenza virus replication or proliferation, or decreases one or more symptoms or complications associated with influenza virus infection in a subject.

19. The antibody of claim 18, wherein the symptom or complication is selected from chills, fever, cough, sore throat, nasal congestion, sinus congestion, nasal infection, sinus infection, body ache, head ache, fatigue, pneumonia, bronchitis, ear infection, ear ache and death.

20. The antibody of any of claims 1 to 3, wherein the antibody has an $EC_{50}$ less than 2.0 to 3.0, 1.0 to 2.0, 0.5 to 1.0, 0.1 to 0.5 or less than 0.1 μg/ml for inhibiting influenza A virus infection of MDCK cells, as determined by a cell based-ELISA assay.

21. The antibody of claim 20, wherein the influenza virus comprises A/PR/8/34, A/HK8/68, A/HK/1/68, H1N1, H3N2, H5N1, H9N2, H6N2, H7N2, or H7N3.

22. The antibody of any of claims 1 to 3, wherein the antibody has an $EC_{50}$ less than 0.05 to 0.1 μg/ml for inhibiting influenza A virus infection of MDCK cells.

23. The antibody of claim 22, wherein the influenza virus comprises A/PR/8/34, A/HK8/68, A/HK/1/68, H1N1, H3N2, H5N1, H9N2, H6N2, H7N2, or H7N3.

24. The antibody of any of claims 1 to 3, wherein the antibody has an $EC_{50}$ less than 2.0 to 3.0, 1.0 to 2.0, 0.5 to 1.0, 0.1 to 0.5 or less than 0.1 ug/ml for inhibiting M2 binding to MDCK cells.

25. The antibody of any of claims 1 to 3, wherein the antibody comprises a human, humanized or chimeric monoclonal antibody.

26. An amino acid subsequence of the antibody of claim 1, wherein the subsequence is selected from heavy and light chain variable regions ($V_H$ and $V_L$), Fab, Fab', F(ab')$_2$, Fv, Fd, single-chain Fv (scFv), disulfide-linked Fvs (sdFv), trispecific ($Fab_3$), bispecific ($Fab_2$), diabody $((V_L\text{-}V_H)_2$ or $(V_H\text{-}V_L)_2)$, triabody (trivalent), tetrabody (tetravalent), minibody $((scF_v\text{-}C_H3)_2)$, bispecific single-chain Fv (Bis-scFv), IgGdeltaCH2, scFv-Fc or (scFv)$_2$-Fc.

27. The antibody of any of claims 1 to 3, wherein the antibody comprises an antibody multimer.

28. The antibody of any of claims 1 to 3 or a subsequence thereof, further comprising one or more heterologous domains.

29. The antibody or the subsequence of claim 28, wherein the heterologous domain comprises an amino acid sequence.

30. The antibody or the subsequence of claim 28, wherein the heterologous domain comprises a binding protein, an enzyme activity, a drug, an antiviral, a toxin, an immune-modulator, a detectable moiety or a tag.

31. The antibody of any of claims 1 to 3, wherein the antibody is a bispecific or bifunctional antibody.

32. An isolated host cell that expresses an antibody of any of claims 1 to 3.

33. The host cell of claim 32, wherein the cell is bacteria, yeast, plant or animal.

34. An isolated nucleic acid encoding an antibody produced by a hybridoma or a CHO cell line denoted as N547 (ATCC Deposit No. PTA-5049; American Type Culture Collection, Manassas, Va., USA), L66 (ATCC Deposit No. PTA-5048; American Type Culture Collection, Manassas, Va., USA), or C40G1 (ATCC Deposit No. PTA-5050; American Type Culture Collection, Manassas, Va., USA).

35. The nucleic acid of claim 34, further comprising a vector.

36. A composition comprising the antibody of any of claims 1 to 3, and an antiviral agent.

37. A composition comprising the antibody of any of claims 1 to 3, and an agent that inhibits or reduces one or more symptoms or complications associated with influenza virus infection.

38. The composition of claim 37, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

39. A pharmaceutical composition comprising the antibody of any of claims 1 to 3, and a pharmaceutically acceptable carrier or excipient.

40. A kit comprising the antibody of any of claims 1 to 3, and instructions for treating, inhibiting or decreasing susceptibility of infection of a subject by one or more influenza virus strains or isolates.

41. The kit of claim 40, further comprising an article of manufacture for delivery of the antibody into a mucosal tissue.

42. The kit of claim 41, wherein the article of manufacture comprises an inhaler, aerosol, spray or squeeze bottle suitable for inhalation or nasal administration to a subject.

43. The kit of claim 41, wherein the mucosal tissue comprises nasal passages, sinuses, mouth, throat, larynx or lungs.

44. The kit of claim 40, further comprising an antiviral agent.

45. A method for treating influenza virus infection of a subject, comprising administering to the subject an amount of an antibody of any of claims 1 to 3 effective to treat influenza virus infection of the subject.

46. The method of claim 45, wherein the antibody is administered prior to, substantially contemporaneously with or following infection of the subject.

47. The method of claim 45, wherein the antibody is administered substantially contemporaneously with or following infection of the subject.

48. The method of claim 45, wherein the administration provides a therapeutic benefit.

49. The method of claim 48, wherein the therapeutic benefit comprises inhibiting increases in virus titer, decreasing virus titer, inhibiting increases in virus replication, decreasing virus replication, inhibiting increases in virus proliferation or decreasing virus proliferation, or decreasing one or more symptoms or complications associated with virus infection in a subject.

50. The method of claim 49, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

51. The method of claim 45, wherein the antibody is produced by a hybridoma or a CHO cell line denoted as N547 (ATCC Deposit No. PTA-5049; American Type Culture Collection, Manassas, Va., USA), L66 (ATCC Deposit No. PTA-5048; American Type Culture Collection, Manassas, Va., USA), or C40G1 (ATCC Deposit No. PTA-5050; American Type Culture Collection, Manassas, Va., USA).

52. The method of claim 45, wherein the influenza strain comprises A/PR/8/34, A/HK8/68, A/HK/1/68, H1N1, H3N2, H5N1, H9N2, H6N2, H7N2, or H7N3.

53. An antibody comprising a heavy-chain variable sequence or a light-chain variable sequence encoded by the nucleic acid sequences of SEQ ID NO:36 and SEQ ID NO:37.

54. An antibody comprising a heavy-chain variable sequence and a light-chain variable sequence as set forth in SEQ ID NO:30 and SEQ ID NO:31.

55. An isolated antibody that specifically binds to a minimal binding sequence that is LLTEVETPIRNEWGC (SEQ ID NO:25), wherein the minimal binding sequence for antibody binding is neither LTEVETPIRNEW (SEQ ID NO:71) nor EVETPIRN (SEQ ID NO:72).

56. The antibody of claim 55, wherein the antibody comprises the heavy and light chain variable region sequence of the antibody produced by the hybridoma N547 (ATCC PTA-5049).

57. The antibody of claim 55, wherein the antibody comprises the mature portion of heavy chain variable region sequence as shown in SEQ ID NO:28 and the mature portion of light chain variable region sequence as shown in SEQ ID NO:29.

58. A method of producing an influenza protein M2 antibody, comprising:

a) providing a hybridoma or a CHO cell line denoted as no. N547 (ATCC Deposit No. PTA-5049; American Type Culture Collection, Manassas, Va., USA), L66 (ATCC Deposit No. PTA-5048; American Type Culture Collection, Manassas, Va., USA), or C40G1 (ATCC Deposit No. PTA-5050; American Type Culture Collection, Manassas, Va., USA) that produces a human M2 antibody; and b) isolating an antibody produced by one of the hybridoma or the CHO cell lines.

* * * * *

SEQUENCE LISTING

```
<160> NUMBER OF SEQ ID NOS: 72

<210> SEQ ID NO 1
<211> LENGTH: 23
<212> TYPE: PRT
<213> ORGANISM: Influenza A Virus

<400> SEQUENCE: 1

Ser Leu Leu Thr Glu Val Glu Thr Pro Ile Arg Asn Glu Trp Gly Cys
1               5                   10                  15

Arg Cys Asn Asp Ser Ser Asp
```

20

<210> SEQ ID NO 2
<211> LENGTH: 23
<212> TYPE: PRT
<213> ORGANISM: Influenza A Virus

<400> SEQUENCE: 2

Ser Leu Leu Thr Glu Val Glu Thr Pro Ile Arg Asn Glu Trp Glu Cys
1 5 10 15

Arg Cys Asn Gly Ser Ser Asp
20

<210> SEQ ID NO 3
<211> LENGTH: 23
<212> TYPE: PRT
<213> ORGANISM: Influenza A Virus

<400> SEQUENCE: 3

Ser Leu Leu Thr Glu Val Glu Thr Pro Ile Arg Asn Glu Trp Gly Cys
1 5 10 15

Lys Cys Asn Asp Ser Ser Asp
20

<210> SEQ ID NO 4
<211> LENGTH: 23
<212> TYPE: PRT
<213> ORGANISM: Influenza A Virus

<400> SEQUENCE: 4

Ser Leu Leu Thr Glu Val Glu Thr Pro Ile Arg Asn Glu Trp Gly Cys
1 5 10 15

Arg Cys Asn Gly Ser Ser Asp
20

<210> SEQ ID NO 5
<211> LENGTH: 23
<212> TYPE: PRT
<213> ORGANISM: Influenza A Virus

<400> SEQUENCE: 5

Ser Phe Leu Thr Glu Val Glu Thr Pro Ile Arg Asn Glu Trp Gly Cys
1 5 10 15

Arg Cys Asn Gly Ser Ser Asp
20

<210> SEQ ID NO 6
<211> LENGTH: 23
<212> TYPE: PRT
<213> ORGANISM: Influenza A Virus

<400> SEQUENCE: 6

Ser Leu Leu Thr Glu Val Asp Thr Leu Thr Arg Asn Gly Trp Gly Cys
1 5 10 15

Arg Cys Ser Asp Ser Ser Asp
20

<210> SEQ ID NO 7
<211> LENGTH: 23
<212> TYPE: PRT
<213> ORGANISM: Influenza A Virus

<400> SEQUENCE: 7

-continued

Ser Leu Leu Thr Glu Val Glu Thr Leu Thr Lys Asn Gly Trp Gly Cys
1 5 10 15

Arg Cys Ser Asp Ser Ser Asp
20

<210> SEQ ID NO 8
<211> LENGTH: 23
<212> TYPE: PRT
<213> ORGANISM: Influenza A Virus

<400> SEQUENCE: 8

Ser Leu Leu Thr Glu Val Glu Thr Leu Thr Arg Asn Gly Trp Gly Cys
1 5 10 15

Arg Cys Ser Asp Ser Ser Asp
20

<210> SEQ ID NO 9
<211> LENGTH: 23
<212> TYPE: PRT
<213> ORGANISM: Influenza A Virus

<400> SEQUENCE: 9

Ser Leu Leu Thr Glu Val Glu Thr Leu Thr Arg Asn Gly Trp Glu Cys
1 5 10 15

Lys Cys Ser Asp Ser Ser Asp
20

<210> SEQ ID NO 10
<211> LENGTH: 23
<212> TYPE: PRT
<213> ORGANISM: Influenza A Virus

<400> SEQUENCE: 10

Ser Leu Leu Thr Glu Val Glu Thr Pro Thr Arg Asn Gly Trp Glu Cys
1 5 10 15

Lys Cys Ser Asp Ser Ser Asp
20

<210> SEQ ID NO 11
<211> LENGTH: 23
<212> TYPE: PRT
<213> ORGANISM: Influenza A Virus

<400> SEQUENCE: 11

Ser Leu Leu Thr Glu Val Glu Thr Pro Thr Arg Asn Glu Trp Glu Cys
1 5 10 15

Arg Cys Ser Asp Ser Ser Asp
20

<210> SEQ ID NO 12
<211> LENGTH: 23
<212> TYPE: PRT
<213> ORGANISM: Influenza A Virus

<400> SEQUENCE: 12

Ser Leu Leu Thr Glu Val Glu Thr Pro Thr Arg Asn Gly Trp Gly Cys
1 5 10 15

Arg Cys Ser Asp Ser Ser Asp
20

<210> SEQ ID NO 13
<211> LENGTH: 23
<212> TYPE: PRT

<213> ORGANISM: Influenza A Virus

<400> SEQUENCE: 13

```
Ser Leu Leu Thr Glu Val Glu Thr Pro Thr Arg Asn Gly Trp Glu Cys
1               5                   10                  15

Lys Cys Asn Asp Ser Ser Asp
            20
```

<210> SEQ ID NO 14
<211> LENGTH: 23
<212> TYPE: PRT
<213> ORGANISM: Influenza A Virus

<400> SEQUENCE: 14

```
Ser Leu Leu Thr Glu Val Lys Thr Pro Thr Arg Asn Gly Trp Glu Cys
1               5                   10                  15

Lys Cys Ser Asp Ser Ser Asp
            20
```

<210> SEQ ID NO 15
<211> LENGTH: 23
<212> TYPE: PRT
<213> ORGANISM: Influenza A Virus

<400> SEQUENCE: 15

```
Ser Leu Leu Thr Glu Val Glu Thr Pro Thr Arg Asp Gly Trp Glu Cys
1               5                   10                  15

Lys Cys Ser Asp Ser Ser Asp
            20
```

<210> SEQ ID NO 16
<211> LENGTH: 23
<212> TYPE: PRT
<213> ORGANISM: Influenza A Virus

<400> SEQUENCE: 16

```
Ser Leu Leu Thr Glu Val Glu Thr His Thr Arg Asn Gly Trp Glu Cys
1               5                   10                  15

Lys Cys Ser Asp Ser Ser Asp
            20
```

<210> SEQ ID NO 17
<211> LENGTH: 23
<212> TYPE: PRT
<213> ORGANISM: Influenza A Virus

<400> SEQUENCE: 17

```
Ser Leu Pro Thr Glu Val Glu Thr Pro Ile Arg Asn Glu Trp Gly Cys
1               5                   10                  15

Arg Cys Asn Asp Ser Ser Asp
            20
```

<210> SEQ ID NO 18
<211> LENGTH: 23
<212> TYPE: PRT
<213> ORGANISM: Influenza A Virus

<400> SEQUENCE: 18

```
Ser Leu Leu Thr Glu Val Glu Thr Pro Ile Arg Ser Glu Trp Gly Cys
1               5                   10                  15

Arg Cys Asn Asp Ser Gly Asp
            20
```

<210> SEQ ID NO 19
<211> LENGTH: 23
<212> TYPE: PRT
<213> ORGANISM: Influenza A Virus

<400> SEQUENCE: 19

```
Ser Leu Leu Thr Glu Val Glu Thr Pro Thr Arg Asn Gly Trp Glu Cys
1               5                   10                  15

Arg Cys Asn Asp Ser Ser Asp
            20
```

<210> SEQ ID NO 20
<211> LENGTH: 29
<212> TYPE: PRT
<213> ORGANISM: Influenza A Virus

<400> SEQUENCE: 20

```
Ser Leu Leu Thr Glu Val Glu Thr Pro Ile Arg Lys Gly Trp Glu Cys
1               5                   10                  15

Asn Cys Ser Asp Ser Ser Asp Met Lys Gly Glu Asn Ser
            20                  25
```

<210> SEQ ID NO 21
<211> LENGTH: 23
<212> TYPE: PRT
<213> ORGANISM: Influenza A Virus

<400> SEQUENCE: 21

```
Ser Leu Leu Thr Gly Val Glu Thr His Thr Arg Asn Gly Trp Gly Cys
1               5                   10                  15

Lys Cys Ser Asp Ser Ser Asp
            20
```

<210> SEQ ID NO 22
<211> LENGTH: 23
<212> TYPE: PRT
<213> ORGANISM: Influenza A Virus

<400> SEQUENCE: 22

```
Ser Leu Leu Pro Glu Val Glu Thr His Thr Arg Asn Gly Trp Gly Cys
1               5                   10                  15

Arg Cys Ser Asp Ser Ser Asp
            20
```

<210> SEQ ID NO 23
<211> LENGTH: 16
<212> TYPE: PRT
<213> ORGANISM: Influenza A Virus

<400> SEQUENCE: 23

```
Ser Leu Leu Thr Glu Val Glu Thr Pro Ile Arg Asn Glu Trp Gly Cys
1               5                   10                  15
```

<210> SEQ ID NO 24
<211> LENGTH: 6
<212> TYPE: PRT
<213> ORGANISM: Influenza A Virus

<400> SEQUENCE: 24

```
Thr Pro Ile Arg Asn Glu
1               5
```

<210> SEQ ID NO 25

-continued

```
<211> LENGTH: 15
<212> TYPE: PRT
<213> ORGANISM: Influenza A Virus

<400> SEQUENCE: 25

Leu Leu Thr Glu Val Glu Thr Pro Ile Arg Asn Glu Trp Gly Cys
1               5                   10                  15


<210> SEQ ID NO 26
<211> LENGTH: 144
<212> TYPE: PRT
<213> ORGANISM: Homo sapiens

<400> SEQUENCE: 26

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Phe Tyr Tyr Cys Gly Trp Ile Arg Gln Pro Pro Gly Lys
    50                  55                  60

Gly Leu Glu Trp Ile Gly Ser Ile Tyr Tyr Arg Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Arg Val Thr Met Val Arg Gly Val Lys Gly
        115                 120                 125

Asp Tyr Phe Asp Tyr Trp Gly Gln Gly Thr Leu Val Thr Val Ser Ser
    130                 135                 140


<210> SEQ ID NO 27
<211> LENGTH: 128
<212> TYPE: PRT
<213> ORGANISM: Homo sapiens

<400> SEQUENCE: 27

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Val Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Tyr Tyr Pro Leu Thr Phe Gly Gly Gly Thr Lys Val Glu Ile Lys Arg
        115                 120                 125


<210> SEQ ID NO 28
<211> LENGTH: 141
<212> TYPE: PRT
```

<213> ORGANISM: Homo sapiens

<400> SEQUENCE: 28

```
Met Glu Phe Gly Leu Ser Trp Ile Phe Leu Thr Ala Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asn Ala Leu Met Ser Trp Val Arg Gln Ala Pro Gly Lys Gly Leu
    50                  55                  60

Glu Trp Val Gly Arg Ile Lys Ser Lys Thr Asn Gly Gly Thr Thr Asp
65                  70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Tyr Cys Thr Thr His Leu Arg Tyr Phe Asp Trp Leu Ser
        115                 120                 125

Asp Tyr Trp Gly Gln Gly Thr Leu Val Thr Val Ser Ser
    130                 135                 140
```

<210> SEQ ID NO 29
<211> LENGTH: 130
<212> TYPE: PRT
<213> ORGANISM: Homo sapiens

<400> SEQUENCE: 29

```
Met Thr Cys Ser Pro Leu Leu Leu Thr Leu Leu Ile His Cys Thr Gly
1               5                   10                  15

Ser Trp Ala Gln Ser Val Leu Thr Gln Pro Pro Ser Met Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Ile Ser Trp Tyr Gln Gln Leu Pro Gly Thr Ala Pro
    50                  55                  60

Lys Val Leu Ile Tyr Asp Asn Asn Lys Arg Pro Ser Gly Ile Pro Asp
65                  70                  75                  80

Arg Phe Ser Gly Ser Lys Ser Gly Thr Ser Ala Thr Leu Gly Ile Thr
                85                  90                  95

Gly Leu Gln Thr Gly Asp Glu Ala Asp Tyr Tyr Cys Gly Ser Trp Asp
            100                 105                 110

Ser Ser Leu Ser Ala Gly Val Phe Gly Thr Gly Thr Lys Val Thr Val
        115                 120                 125

Leu Gly
    130
```

<210> SEQ ID NO 30
<211> LENGTH: 146
<212> TYPE: PRT
<213> ORGANISM: Homo sapiens

<400> SEQUENCE: 30

```
Met Glu Phe Gly Leu Ser Trp Val Phe Leu Val Ala Ile Leu Lys Gly
1               5                   10                  15

Val Gln Cys Glu Val Gln Leu Val Glu Ser Gly Gly Gly Val Val Arg
            20                  25                  30
```

-continued

```
Pro Gly Gly Ser Leu Arg Leu Ser Cys Ala Ala Ser Gly Phe Thr Phe
        35                  40                  45

Asp Asp Tyr Gly Met Ser Trp Val Arg Gln Ala Pro Gly Lys Gly Leu
    50                  55                  60

Glu Trp Val Ser Gly Ile Asn Trp Asn Gly Gly Ser Thr Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Arg Asp Arg Val Thr Met Val Arg Gly Val Ile Met
        115                 120                 125

Asp Tyr Tyr Gly Met Asp Val Trp Gly Gln Gly Thr Thr Val Thr Val
    130                 135                 140

Ser Ser
145
```

<210> SEQ ID NO 31
<211> LENGTH: 129
<212> TYPE: PRT
<213> ORGANISM: Homo sapiens

<400> SEQUENCE: 31

```
Met Ala Trp Thr Pro Leu Phe Leu Phe Leu Leu Thr Cys Cys Pro Gly
1               5                   10                  15

Ser Asn Ser Gln Thr Val Val Thr Gln Glu Pro Ser Leu Thr Val Ser
            20                  25                  30

Pro Arg Gly Thr Val Thr Leu Thr Cys Ser Ser Ser Thr Gly Ala Val
        35                  40                  45

Thr Ser Gly Tyr Tyr Pro Gly Trp Phe Gln Leu Lys Pro Gly Gln Ala
    50                  55                  60

Pro Met Ser Leu Ile Tyr Ser Ala Arg Lys Lys His Ser Trp Thr Pro
65                  70                  75                  80

Ala Arg Phe Ser Gly Ser Leu Leu Gly Gly Lys Ala Ala Leu Thr Leu
                85                  90                  95

Ser Gly Val Gln Pro Glu Asp Glu Ala Glu Tyr Tyr Cys Leu Leu Tyr
            100                 105                 110

Tyr Gly Gly Ala Tyr Val Phe Gly Thr Gly Thr Lys Val Thr Val Leu
        115                 120                 125

Gly
```

<210> SEQ ID NO 32
<211> LENGTH: 432
<212> TYPE: DNA
<213> ORGANISM: Homo sapiens

<400> SEQUENCE: 32

```
atgaagcacc tgtggttctt cctcctgctg gtggcggctc ccagatgggt cctgtcccag     60

ctgcagctgc aggagtcggg cccaggactg gtgaagcctt cggagaccct gtccctcacc    120

tgcactgtct ctggtggttc catcagcagt agtttttact actgtggctg gatccgccag    180

cccccaggga aggggctgga gtggattggg agtatctatt atcgtgggag cacctactac    240

aacccgtccc tcaagagtcg agtcaccata tccgtagaca cgtccaagaa ccagttctcc    300

ctgaagctga gctctgtgac cgccgcagac acggctgtgt attactgtgc gagacgggtt    360

actatggttc ggggagttaa gggggactac tttgactact ggggccaggg aaccctggtc    420
```

accgtctcct ca 432

<210> SEQ ID NO 33
<211> LENGTH: 384
<212> TYPE: DNA
<213> ORGANISM: Homo sapiens

<400> SEQUENCE: 33
atgagggtcc tcgctcagct cctggggctc ctgctgctct gtttcccagg tgccagatgt 60
gacatccaga tgacccagtc tccatcctca ctgtctgcat ctgtaggaga cagagtcacc 120
atcacttgtc gggcgagtca gggtattagc agctggttag cctggtatca gcagaaacca 180
gagaaagtcc ctaagtccct gatctatgct gcatccagtt tgcaaagtgg ggtcccatca 240
aggttcagcg gcagtggatc tgggacagat ttcactctca ccatcagcag cctgcagcct 300
gaagattttg caacttatta ctgccaacag tataattatt acccgctcac tttcggcgga 360
gggaccaagg tggagatcaa acga 384

<210> SEQ ID NO 34
<211> LENGTH: 423
<212> TYPE: DNA
<213> ORGANISM: Homo sapiens

<400> SEQUENCE: 34
atggagtttg ggctgagctg gattttcctt actgctattt taaaaggtgt ccagtgtgag 60
gtgcaactgg tggagtctgg gggaggcttg gtaaagcctg gggggtccct tagactctcc 120
tgtgcagcct ctggattcac tttcagtaac gccttgatga gctgggtccg ccaggctcca 180
gggaagggac tggagtgggt tggccgtatt aaaagcaaaa ctaatggtgg gacaacagac 240
tacgctgcac ccgtgaaagg cagattcacc atctcaagag atgattcaaa aaacacgctg 300
tatctgcaaa tgaacagcct gaaaaccgag gacacagccg tgtattactg taccacccat 360
ctacgatatt ttgactggtt atctgactac tggggccagg gaaccctggt caccgtctcc 420
tca 423

<210> SEQ ID NO 35
<211> LENGTH: 390
<212> TYPE: DNA
<213> ORGANISM: Homo sapiens

<400> SEQUENCE: 35
atgacctgct cccctctcct cctcaccctt ctcattcact gcacagggtc ctgggcccag 60
tctgtgttga cgcagccgcc ctcaatgtct gcggccccag gacagaaggt caccatctcc 120
tgctctggaa gcagctccaa cattgggaat aattatatat cctggtacca gcagctccca 180
ggaacagccc ccaaagtcct catttatgac aataataagc gaccctcagg gattcctgac 240
cgattctctg gctccaagtc tggcacgtca gccaccctgg gcatcaccgg actccagact 300
ggggacgagg ccgattatta ctgcggatca tgggatagca gcctgagtgc tggtgtcttc 360
ggaactggga ccaaggtcac cgtcctaggt 390

<210> SEQ ID NO 36
<211> LENGTH: 438
<212> TYPE: DNA
<213> ORGANISM: Homo sapiens

<400> SEQUENCE: 36
atggagtttg ggctgagctg ggttttcctt gttgctattt taaaaggtgt ccagtgtgag 60

-continued

```
gtgcagctgg tggagtctgg gggaggtgtg gtacggcctg gggggtccct gagactctcc    120

tgtgcagcct ctggattcac ctttgatgat tatggcatga gctgggtccg ccaagctcca    180

gggaaggggc tggagtgggt ctctggtatt aattggaatg gtggtagcac aggttatgca    240

gactctgtga agggccgatt caccatctcc agagacaacg ccaagaactc cctgtatctg    300

caaatgaaca gtctgagagc cgaggacacg gccttgtatt actgtgcgag agatcgagtt    360

actatggttc ggggagttat tatggactac tacggtatgg acgtctgggg ccaagggacc    420

acggtcaccg tctcctca                                                  438


<210> SEQ ID NO 37
<211> LENGTH: 387
<212> TYPE: DNA
<213> ORGANISM: Homo sapiens

<400> SEQUENCE: 37

atggcctgga ctcctctctt tctgttcctc ctcacttgct gcccagggtc caattctcag     60

actgtggtga ctcaggagcc ctctctgact gtgtccccaa gagggacagt cactctcacc    120

tgttcttcca gcactggagc agtcaccagt ggttactatc caggctggtt ccagctgaaa    180

cctggacaag cacccatgtc actgatttat agtgcaagga aaaaacactc ctggacccct    240

gcccggttct caggctccct ccttgggggc aaagctgccc tgacactgtc aggtgtgcag    300

cctgaggacg aggctgagta ttactgcctg ctctactatg gtggtgctta tgtcttcgga    360

actgggacca aggtcaccgt cctaggt                                        387


<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthesized
      DNA Primer

<400> SEQUENCE: 38

tcttgtccac cttggtgttg ctgggcttgt g                                    31


<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthesized
      DNA Primer

<400> SEQUENCE: 39

gttgaagctc tttgtgacgg gcgagc                                         26


<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthesized
      DNA Primer

<400> SEQUENCE: 40

ggtgccaggg ggaagaccga tgg                                            23


<210> SEQ ID NO 41
<211> LENGTH: 30
<212> TYPE: DNA
<213> ORGANISM: Artificial Sequence
```

<220> FEATURE:
<223> OTHER INFORMATION: Description of Artificial Sequence: Synthesized DNA Primer

<400> SEQUENCE: 41
aggcacacaa cagaggcagt tccagatttc 30

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 42
ggtccgggag atcatgaggg tgtcctt 27

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 43
gatttaggtg acactatag 19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 44
taatacgact cactataggg 20

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 45
agagagagag atctctcacc atgagggtcc tcgctcagct cctg 44

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 46
ctctctctcg tacgtttgat ctccaccttg gtcc 34

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 47
agagagaggt cgacaccatg aagcacctgt ggttcttcct 40

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 48
ctctctctgc tagctgagga gacggtgacc agg 33

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 49
ggtacgtgaa ccgtcagatc gcctgga 27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 50
tctatataag cagagctggg tacgtcc 27

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 51
ccaagggccc atcggtcttc cccctggcac 30

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 52
gacaccctca tgatctcccg gacc 24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 53
cgacatcgcc gtggagtggg agag 24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 54
tgttctccgg ctgcccattg ctct 24

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthesized DNA Primer

<400> SEQUENCE: 55
tggctgcacc atctgtcttc atcttc 26

<210> SEQ ID NO 56
<211> LENGTH: 16
<212> TYPE: PRT
<213> ORGANISM: Influenza A Virus

<400> SEQUENCE: 56

Leu Leu Thr Glu Val Glu Thr Pro Ile Arg Asn Glu Trp Gly Cys Arg
1 5 10 15

<210> SEQ ID NO 57
<211> LENGTH: 15
<212> TYPE: PRT
<213> ORGANISM: Influenza A Virus

<400> SEQUENCE: 57

Leu Thr Glu Val Glu Thr Pro Ile Arg Asn Glu Trp Gly Cys Arg
1 5 10 15

<210> SEQ ID NO 58
<211> LENGTH: 12
<212> TYPE: PRT
<213> ORGANISM: Influenza A Virus

<400> SEQUENCE: 58

Val Glu Thr Pro Ile Arg Asn Glu Trp Gly Cys Arg
1 5 10

<210> SEQ ID NO 59
<211> LENGTH: 17
<212> TYPE: PRT
<213> ORGANISM: Influenza A Virus

<400> SEQUENCE: 59

Glu Thr Pro Ile Arg Asn Glu Trp Gly Cys Arg Cys Asn Asp Ser Ser
1 5 10 15

Asp

<210> SEQ ID NO 60
<211> LENGTH: 16
<212> TYPE: PRT

<213> ORGANISM: Influenza A Virus

<400> SEQUENCE: 60

Thr Pro Ile Arg Asn Glu Trp Gly Cys Arg Cys Asn Asp Ser Ser Asp
1 5 10 15

<210> SEQ ID NO 61
<211> LENGTH: 15
<212> TYPE: PRT
<213> ORGANISM: Influenza A Virus

<400> SEQUENCE: 61

Pro Ile Arg Asn Glu Trp Gly Cys Arg Cys Asn Asp Ser Ser Asp
1 5 10 15

<210> SEQ ID NO 62
<211> LENGTH: 14
<212> TYPE: PRT
<213> ORGANISM: Influenza A Virus

<400> SEQUENCE: 62

Ile Arg Asn Glu Trp Gly Cys Arg Cys Asn Asp Ser Ser Asp
1 5 10

<210> SEQ ID NO 63
<211> LENGTH: 13
<212> TYPE: PRT
<213> ORGANISM: Influenza A Virus

<400> SEQUENCE: 63

Arg Asn Glu Trp Gly Cys Arg Cys Asn Asp Ser Ser Asp
1 5 10

<210> SEQ ID NO 64
<211> LENGTH: 12
<212> TYPE: PRT
<213> ORGANISM: Influenza A Virus

<400> SEQUENCE: 64

Asn Glu Trp Gly Cys Arg Cys Asn Asp Ser Ser Asp
1 5 10

<210> SEQ ID NO 65
<211> LENGTH: 17
<212> TYPE: PRT
<213> ORGANISM: Influenza A Virus

<400> SEQUENCE: 65

Ser Leu Leu Thr Glu Val Glu Thr Pro Ile Arg Asn Glu Trp Gly Cys
1 5 10 15

Arg

<210> SEQ ID NO 66
<211> LENGTH: 15
<212> TYPE: PRT
<213> ORGANISM: Influenza A Virus

<400> SEQUENCE: 66

Ser Leu Leu Thr Glu Val Glu Thr Pro Ile Arg Asn Glu Trp Gly
1 5 10 15

<210> SEQ ID NO 67
<211> LENGTH: 14
<212> TYPE: PRT
<213> ORGANISM: Influenza A Virus -continued

```
<400> SEQUENCE: 67

Ser Leu Leu Thr Glu Val Glu Thr Pro Ile Arg Asn Glu Trp
1               5                   10


<210> SEQ ID NO 68
<211> LENGTH: 13
<212> TYPE: PRT
<213> ORGANISM: Influenza A Virus

<400> SEQUENCE: 68

Ser Leu Leu Thr Glu Val Glu Thr Pro Ile Arg Asn Glu
1               5                   10


<210> SEQ ID NO 69
<211> LENGTH: 12
<212> TYPE: PRT
<213> ORGANISM: Influenza A Virus

<400> SEQUENCE: 69

Ser Leu Leu Thr Glu Val Glu Thr Pro Ile Arg Asn
1               5                   10


<210> SEQ ID NO 70
<211> LENGTH: 11
<212> TYPE: PRT
<213> ORGANISM: Influenza A Virus

<400> SEQUENCE: 70

Ser Leu Leu Thr Glu Val Glu Thr Pro Ile Arg
1               5                   10


<210> SEQ ID NO 71
<211> LENGTH: 12
<212> TYPE: PRT
<213> ORGANISM: Influenza A Virus

<400> SEQUENCE: 71

Leu Thr Glu Val Glu Thr Pro Ile Arg Asn Glu Trp
1               5                   10


<210> SEQ ID NO 72
<211> LENGTH: 8
<212> TYPE: PRT
<213> ORGANISM: Influenza A Virus

<400> SEQUENCE: 72

Glu Val Glu Thr Pro Ile Arg Asn
1               5
```